(12) United States Patent
Ahuja et al.

(10) Patent No.: US 8,428,739 B2
(45) Date of Patent: Apr. 23, 2013

(54) SYSTEM AND METHOD FOR MEASURING AND FITTING SPATIO-TEMPORAL VISION

(75) Inventors: Ashish Ahuja, Los Angeles, CA (US);
Avraham Caspi, La Jolla, CA (US);
Jessy Dorn, Los Angeles, CA (US);
Robert J. Greenberg, Los Angeles, CA (US); Kelly H. McClure, Simi Valley, CA (US); Matthew J. McMahon, Washington, DC (US); Devyani Nanduri, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 752 days.

(21) Appl. No.: 12/548,275

(22) Filed: Aug. 26, 2009

(65) Prior Publication Data

US 2010/0057166 A1   Mar. 4, 2010

Related U.S. Application Data

(60) Provisional application No. 61/092,001, filed on Aug. 26, 2008.

(51) Int. Cl.
*A61N 1/18*   (2006.01)
(52) U.S. Cl.
USPC ............................................. 607/53; 607/54
(58) Field of Classification Search ............... 607/53–54
See application file for complete search history.

(56) References Cited

U.S. PATENT DOCUMENTS

| | | | |
|---|---|---|---|
| 5,109,844 A | 5/1992 | de Juan, Jr. et al. |
| 5,935,155 A | 8/1999 | Humayun et al. |
| 6,400,989 B1 | 6/2002 | Eckmiller |
| 6,458,157 B1 | 10/2002 | Suaning |

FOREIGN PATENT DOCUMENTS

WO   WO 2007/127444 A   11/2007

OTHER PUBLICATIONS

Rizzo, J. F., et al., Perceptual Efficacy of Electrical Stimulation of Human Retina with Microelectrode Array During Short-Term Surgical Trials, Investigative Ophthalmology & Visual Science, Association for Research in Vision and Opthalmology, vol. 44, No. 129: pp. 5362-5369, Dec. 1, 2003.

*Primary Examiner* — Carl H Layno
*Assistant Examiner* — Paula J Stice
(74) *Attorney, Agent, or Firm* — Scott B. Dunbar

(57) ABSTRACT

This system gives the experimenter great flexibility to present spatio-temporal stimulation patterns to a subject. A video configuration file (VCF) editor allows the experimenter to determine the electrical stimulation parameters for each electrode. A Pattern Stimulation software program allows direct stimulation of chosen patterns of electrodes, scaled by the subject's VCF, through a Graphical User Interface. The subject then responds by drawing the outline of the phosphene he or she perceives on a touchscreen. The Pattern Stimulation program saves all of the trial parameters and the parameters of an ellipse fit to their drawing, as well as a raw data file containing the input to the touchscreen is saved. After the experiment, offline image analysis can be performed to obtain a detailed quantitative description of the subject's percepts. Image descriptors can assigned to the touchscreen data; these image descriptors can be used to make formalized comparisons between various experimental conditions. Various types of image descriptors can be used, including simple ellipse fitting, projections of the 2-D drawings onto one-dimensional axes, calculations of Hu moments, PCA, and ICA.

10 Claims, 52 Drawing Sheets

U.S. PATENT DOCUMENTS

2005/0004624 A1* 1/2005 Gliner et al. .................. 607/54
2005/0288932 A1 12/2005 Kurzweil
2006/0184062 A1* 8/2006 Greenberg et al. ........... 600/558
2008/0162389 A1 7/2008 Aboutalib

* cited by examiner

FIG. 22

| EXPERIMENTER: t1 | SUBJECT: 000-000 | VPU ☐ | IMPLANT ☐ | STIMULATION ☐ | CDLS: PC MODE: 0.35, STANDALONE: 0.35 | FRI FEB 15 00:13:52 GMT 2008 |

| DIAGNOSTICS | WAVEFORM VIEWER | PSYCHOPHYSICS | VIDEO | OPTIONS |

PTS SERVER

EXPERIMENT: DIRECT STIMULATION

*FIG. 27*

| CLASS | SUMMARY |
|---|---|
| VIDEO CONFIGURATION | VIDEO CONFIGURATION OBJECT USED BY THE CFS APPLICATION TO COMMUNICATE WITH THE VPU. |
| BRIGHTNESS MAP | BRIGHTNESS MAP OBJECT USED BY THE CFS APPLICATION |
| SPATIAL MAP | SPATIAL MAP OBJECT USED BY THE CFS APPLICATION |
| PROFILE TIMING | PROFILE TIMING OBJECT USED BY THE CFS APPLICATION |
| TIMING MAP | TIMING MAP OBJECT USED BY THE CFS APPLICATION |
| RASTERING ASSIGNMENT | RASTERING ASSIGNMENT OBJECT USED BY THE CFS APPLICATION |
| VIDEO SETTINGS Csv READER WRITER | CFS OBJECT TO READ AND WRITE VIDEO SETTINGS FROM AND TO A CSV FILE |
| IMPLANT PROPERTIES | IMPLANT RELATED PROPERTIES, SUCH AS CHARGE LIMIT, PROFILE TIMING LIMITS, ETC |
| IMPLANT GEOMETRY | IMPLANT GEOMETRY PROPERTIES, SUCH AS THE LAYOUT/POSITION OF ELECTRODES, ETC |

SYSTEM AND METHOD FOR MEASURING AND FITTING SPATIO-TEMPORAL VISION

CROSS REFERENCE TO RELATED APPLICATIONS

This application claim priority to, and incorporates by reference, U.S. provisional application 61/092,001, filed Aug. 26, 2008, for System and Method for Measuring Spatio-Temporal Vision.

FEDERALLY SPONSORED RESEARCH OR DEVELOPMENT

The present invention was made with support from the United States Government under Grant number R24EY12893-1, awarded by the National Institutes of Health. The United States Government has certain rights in the invention.

FIELD

The present disclosure relates to visual prostheses. In particular, the present disclosure relates to configuring a visual prosthesis implanted in a patient and controlling a video configuration file for visual prosthesis fitting. More particularly, it relates to a video configuration file editor for visual prosthesis fitting and related method.

BACKGROUND OF THE INVENTION

Arrays of electrodes for neural stimulation are commonly used for a variety of purposes. Some examples include: U.S. Pat. No. 3,699,970 to Brindley and "The Sensations Produced by Electrical Stimulation of the Visual Cortex" by G. Brindley and W. Lewin, J. Physiol (London) 196:479-493:1968. Brindley's paper and patent describe an array of cortical electrodes for visual stimulation. One cortical electrode is used for each light percept. Each electrode is attached to a separate inductive coil for signal and power. U.S. Pat. No. 4,573,481 to Bullara describes a helical electrode to be wrapped around an individual nerve fiber. U.S. Pat. No. 4,628,933 to Michelson describes an electrode array for retinal stimulation. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

In addition to the electrode arrays described above, there are several methods of mapping a high resolution camera image to a lower resolution electrode array. U.S. Pat. No. 6,400,989 to Eckmiller describes spatio-temporal filters for controlling patterns of stimulation in an array of electrodes. The assignee of the present applications has three related U.S. patent application Ser. No. 09/515,373, filed Feb. 29, 2000, entitled Retinal Color Prosthesis for Color Sight Restoration and Ser. No. 09/851,268, filed May 7, 2001, entitled Method, Apparatus and System for Improved Electronic Acuity and Perceived Resolution Using Eye Jitter Like Motion. Both applications are incorporated herein by reference.

Each person's response to neural stimulation differs. In the case of retinal stimulation, a person's response varies from one region of the retina to another. In general, the retina is more sensitive closer to the fovea. Any stimulation, less than the threshold of perception, is ineffective. Stimulation beyond a maximum level will be painful and possibly dangerous to the patient. It is therefore, important to map any video image to a range between the minimum and maximum for each individual electrode. With a simple retinal prosthesis, it is possible to adjust the stimulation manually by stimulating and questioning the patient. As resolution increases, it is tedious or impossible to adjust each electrode by stimulating and eliciting a patient response.

A manual method of fitting or adjusting the stimulation levels of an auditory prosthesis is described in U.S. Pat. No. 4,577,642, Hochmair et al. Hochmair adjusts the auditory prosthesis by having a user compare a received signal with a visual representation of that signal.

A more automated system of adjusting an auditory prosthesis using middle ear reflex and evoked potentials is described in U.S. Pat. No. 6,157,861, Faltys et al. An alternate method of adjusting an auditory prosthesis using the stapedius muscle is described in U.S. Pat. No. 6,205,360, Carter et al. A third alternative using myogenic evoked response is disclosed in U.S. Pat. No. 6,415,185, Maltan.

U.S. Pat. No. 6,208,894, Schulman describes a network of neural stimulators and recorders implanted throughout the body communicating wirelessly with a central control unit. U.S. Pat. No. 6,522,928, Whitehurst, describes an improvement on the system described in Schulman using function electro stimulation also know as adaptive delta modulation to communicate between the implanted devices and the central control unit.

The greatest dynamic range is achieved by setting the minimum stimulation at the threshold of perception and the maximum stimulation level approaching the pain threshold. It is unpleasant for a patient to first concentrate to detect the minimum perception and then be subjected to stimulation near the threshold of pain.

The human retina includes about four million individual photoreceptors. An effective visual prosthesis may include thousands of electrodes. An automated system is needed to adjust individual electrodes in a visual prosthesis for maximum benefit without the need for patient interaction in a long and difficult process.

SUMMARY

This system gives the experimenter great flexibility to present spatio-temporal stimulation patterns to a subject. A video configuration file (VCF) editor allows the experimenter to determine the electrical stimulation parameters for each electrode. A Pattern Stimulation software program allows direct stimulation of chosen patterns of electrodes, scaled by the subject's VCF, through a Graphical User Interface. The subject then responds by drawing the outline of the phosphene he or she perceives on a touchscreen. The Pattern Stimulation program saves all of the trial parameters and the parameters of an ellipse fit to their drawing, as well as a raw data file containing the input to the touchscreen is saved. After the experiment, offline image analysis can be performed to obtain a detailed quantitative description of the subject's percepts. Image descriptors can assigned to the touchscreen data; these image descriptors can be used to make formalized comparisons between various experimental conditions. Various types of image descriptors can be used, including simple ellipse fitting, projections of the 2-D drawings onto one-dimensional axes, calculations of Hu moments, PCA, and ICA.

Further embodiments are shown in the specification, drawings and claims of the present application.

BRIEF DESCRIPTION OF THE FIGURES

FIG. 22 shows a 'IN TRIAL: Threshold with method of adjustment' message.
FIG. 27 shows an 'EXPERIMENT: direct stimulation' message box.
FIG. 46 is a table showing some additional software classes that can be used by the VCF editor.
FIG. 53 shows a result of an algorithm for assigning a timing group.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

The present disclosure describes a method of fitting, configuring and optimizing a visual prosthesis (i.e. device) for an individual patient (i.e. subject) including creating a map of brightness to electrical stimulation levels for each electrode, and using that map for the stimulation of retinal neurons to create artificial vision. Also described is operation and use of a video configuration file (VCF) editor. A VCF specifies the method for converting the output of a video chain to the temporal pattern of stimulation values for each electrode and involves a timing map, spatial mapping and brightness mapping, as later explained in detail.

Figure 1:
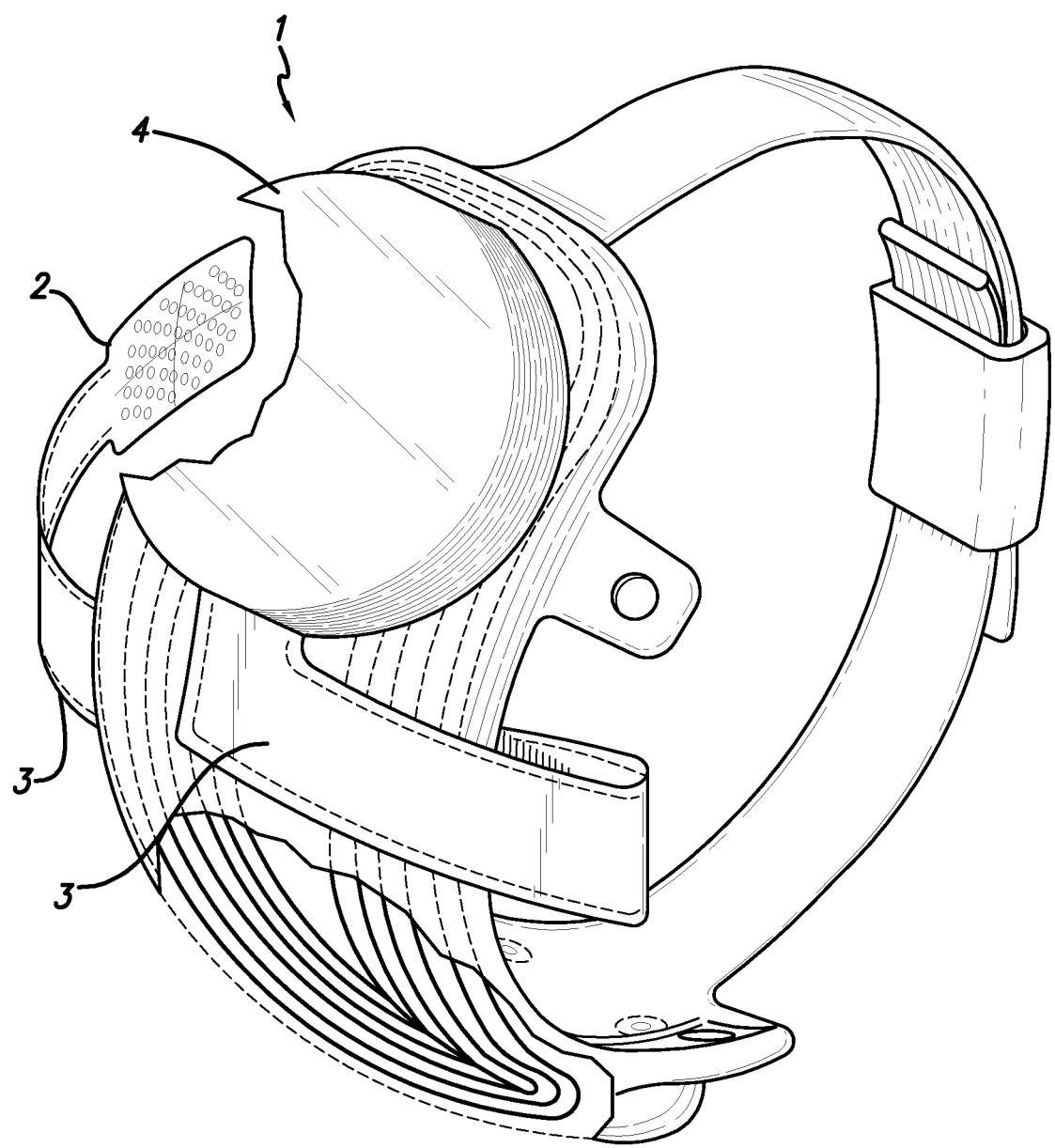
FIGS. 1 and 2 show a retinal stimulation system.
Figure 2:
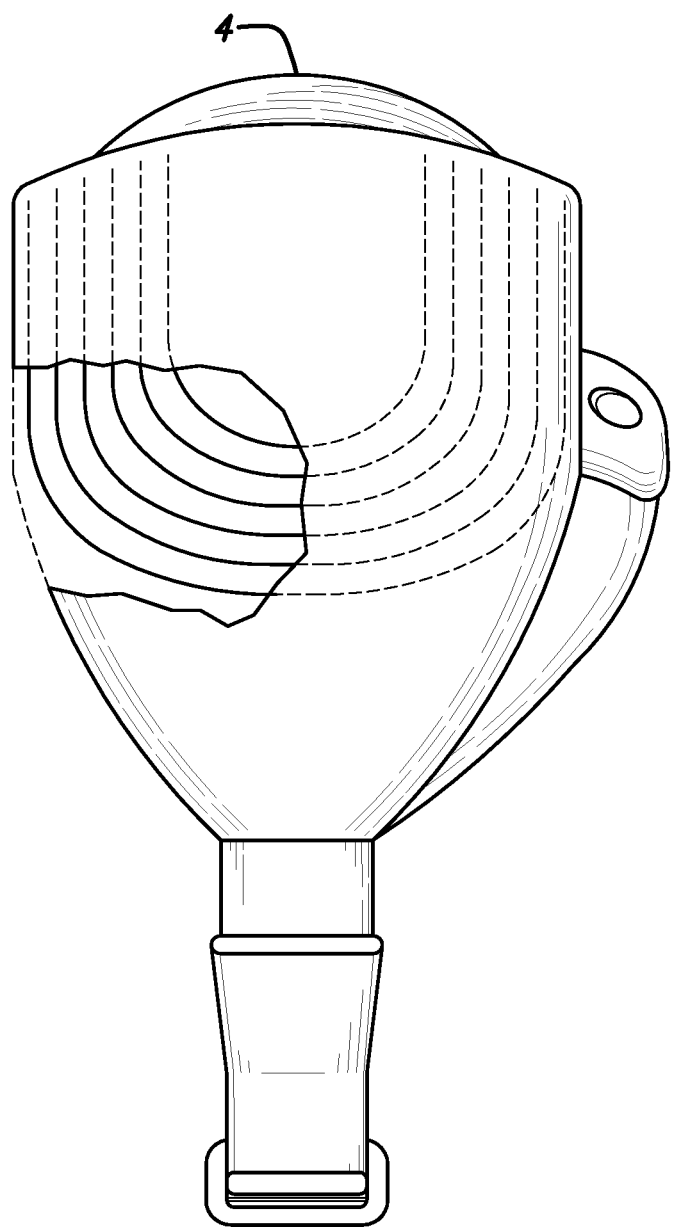

A Retinal Stimulation System, disclosed in U.S. application Ser. No. 11/207,644, filed Aug. 19, 2005 for "Flexible Circuit Electrode Array" by Robert J. Greenberg, et, al. incorporated herein by reference, is intended for use in subjects with retinitis pigmentosa. FIG. 1 and FIG. 2 show a Retinal Stimulation System (1) wherein a patient/subject is implanted with a visual prosthesis to be fitted, configured and optimized according to the present disclosure.

The Retinal Stimulation System (1) is an implantable electronic device containing electrode array (2) that is electrically coupled by a cable (3) that pierces sclera of the subject's eye and is electrically coupled to an electronics package (4), external to the sclera. The Retinal Stimulation System (1) is designed to elicit visual percepts in blind subjects with retinitis pigmentosa.

The fitting system and method according to the present disclosure may be used to establish the most effective Video Processing Unit (VPU) settings for subjects implanted with a visual prosthesis. The psychophysical testing according to the present disclosure will be used to establish the electrical pulse parameters for stimulating retinal neurons and to determine the optimal method for transforming the video input signal to a useful pattern of electrical stimulation.

Establishing a stimulation level that is just detectable to a subject (threshold) allows establishing the lowest stimulation value to be used when mapping the darkest barely visible part of the video image to a stimulation profile. A 150-750 ms train of 10-100 Hz pulses (e.g., nine or ten pulses) may be used as the standard stimulus to determine the threshold. By way of example and not of limitation, the current threshold for each individual electrode may be determined using a method of adjustment.

The procedure for converting a video camera input to a pattern of electrical stimulation can be broken down into two general parts: the video chain and the video configuration file (VCF).

The Video Chain

The image is initially captured by a video camera mounted on the frame of the glasses. This video image is sent to a Video Processing Unit (VPU), where the video input signal (e.g., NTSC video input signal) is converted to a digital image. This digital image is processed by a series of digital filters. The goal of these operations is to construct a processed video image that is to be presented to the retina by way of electrical stimulation. This includes any contrast, brightness or zoom manipulation as well as any additional filtering to convert the video image to the inferred "neural image" best suited for presentation to the retinal circuitry.

The goal of the video chain is to output an image that is to be presented to the retina. This image to be presented to the retina should have sufficient spatial resolution and a large enough field of view to accommodate any spatial transformation needed to construct the VCF (see below). The image to be presented to the retina should consist of intensity values that are scaled from black (0) to white (255) in a way that allows it to maximize the dynamic range for perceived brightness generated by the VCF (see below).

The Video Configuration File (VCF)

The VCF specifies the method for converting the output of the video chain to the temporal pattern of stimulation values for each electrode and involves the Timing Map, Spatial Mapping and Brightness Mapping.

The output of the video chain is an image that has higher resolution than the electrode array. The goal of the Spatial Mapping is to determine which parts of the image are mapped to the individual electrodes. The video image may be initially mapped to the electrodes using the retinotopic co-ordinates (measured using fluidus photograph) of the electrodes. A matrix transformation procedure may be used to sub-sample the image down to the resolution of the electrode array.

The above described basic retinotopic organization may be checked using two-point discrimination. In particular, pairs of electrodes may be presented in close temporal sequence and subjects may be asked about the relative position of the pair, e.g. did the dot pair move Left-Right or Right-Left.

Another method for determining the spatial mapping is to determine the map of the locations of the phosphenes generated by every electrode in the array and use this map to determine which sections of the image each electrode is mapped to. The phosphene locations can be obtained by stimulating an electrode and asking the subject to place a reflective ball in the 3D location of the phosphene. The 3D location of the ball can be measured with an infrared stereo camera system. The advantage of this technique is that it directly takes into account any spatial distortions in the perceived locations of the electrodes or phosphenes. The disadvantage is that it requires the experimenter to obtain a map of the phosphenes generated by every electrode. Interpolation techniques may be used to determine the spatial map of the phosphene locations without making a measurement for every electrode. If the mapping is orderly, it may be possible to sample fewer electrodes and still be able to map the distortions in the perceived locations of the electrodes or phosphenes.

Once it has been determined which parts of the image are mapped to which electrode, a single number will be determined to represent the brightness of that section of pixels in the image through Brightness Mapping. Various methods could be used to determine this value. This selection determines the single intensity value that is to be transmitted to the retina, through an electrical stimulation protocol.

The method of fitting Retinal Stimulation System (1) according to the present disclosure may include a technique for mapping the position in the visual field of the phosphenes produced by stimulating each electrode in the electrode array (2) of FIG. 1. These phosphene locations may then be overlayed on the video image to determine the spatial regions of the video image that are mapped to each electrode.

The results of these mappings may then be used to construct a lookup table that specifies which sections of the video image are used to determine the stimulation level sent to a given electrode. For instance, if a phosphene produces a large circle in the upper-left part of the video image, then the stimulation sent to this electrode is determined by analyzing that part of the video image in real-time.

This method of mapping the video image to the spatial pattern of stimulation accurately corrects any spatial distortions of the retinotopic map. It can rapidly and easily be done and results in a spatial map that is customized for each individual subject.

The goal of the Brightness Mapping procedure is to produce a perceptual brightness level that corresponds to this intensity value. This can be accomplished in a number of different ways. For instance, by varying the pulse amplitude to control brightness (amplitude coding), the pulse frequency (frequency coding), the pulse width, or directly modulating the ganglion cell output with short electrical pulses of varying frequency (temporal coding). The VCF needs to ensure that equally bright image values are transformed into stimulation patterns that give as a result equally bright phosphenes. This mapping is established by determining the pulse parameter value to be mapped to the minimum image value (0) for each electrode, determining the pulse parameter value to be mapped for the maximum image value (255), and determining the mapping for the intermediate values.

For amplitude coding, the 0 intensity value may be set to be equal to the threshold pulse amplitude for every electrode. For the electrode with the median threshold, the 255 intensity value may be set to the maximum safe current level. The more sensitive electrodes will have the 255 intensity value mapped to the current amplitude that matches the brightness of the median electrode at its maximum current level. When the less sensitive electrodes are set to their maximum amplitude, they will be perceptually dimmer than the median electrode at its maximum amplitude. Every electrode will linearly map the intensity values to the amplitude range between the specified min and max values.

Figure 3:
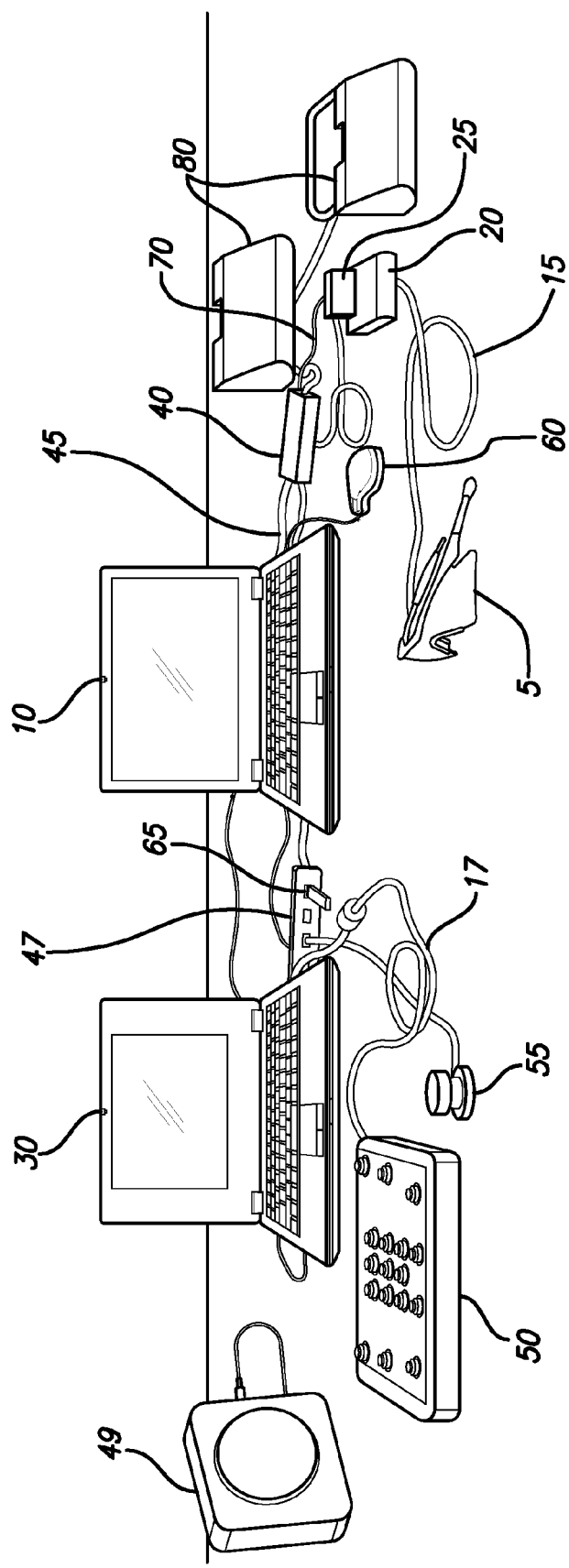
FIG. 3 shows components of a fitting system.

Referring to FIG. 3, a Fitting System (FS) according to the present disclosure may be used to configure and optimize the visual prosthesis (3) of the Retinal Stimulation System (1).

The Fitting System may comprise custom software with a graphical user interface (GUI) running on a dedicated laptop computer (10). Within the Fitting System are modules for performing diagnostic checks of the implant, loading and executing video configuration files, viewing electrode voltage waveforms, and aiding in conducting psychophysical experiments. A video module can be used to download a video configuration file to a Video Processing Unit (VPU) (20) and store it in non-volatile memory to control various aspects of video configuration, e.g. the spatial relationship between the video input and the electrodes. The software can also load a previously used video configuration file from the VPU (20) for adjustment.

The Fitting System can be connected to the Psychophysical Test System (PTS), located for example on a dedicated laptop (30), in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Any time stimulation is sent to the VPU (20), the stimulation parameters are checked to ensure that maximum charge per phase limits, charge balance, and power limitations are met before the test stimuli are sent to the VPU (20) to make certain that stimulation is safe.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the retinal prosthesis for each subject.

The Fitting System laptop (10) is connected to the VPU (20) using an optically isolated serial connection adapter (40). Because it is optically isolated, the serial connection adapter (40) assures that no electric leakage current can flow from the Fitting System laptop (10).

As shown in FIG. 3, the following components may be used with the Fitting System according to the present disclosure. A Video Processing Unit (VPU) (20) for the subject being tested, a Charged Battery (25) for VPU (20), Glasses (5), a Fitting System (FS) Laptop (10), a Psychophysical Test System (PTS) Laptop (30), a PTS CD (not shown), a Communication Adapter (CA) (40), a USB Drive (Security) (not shown), a USB Drive (Transfer) (not shown), a USB Drive (Video Settings) (not shown), a Patient Input Device (RF Tablet) (50), a further Patient Input Device (Jog Dial) (55), Glasses Cable (15), CA-VPU Cable (70), CFS-CA Cable (45), CFS-PTS Cable (46), Four (4) Port USB Hub (47), Mouse (60), LED Test Array (80), Archival USB Drive (49), an Isolation Transformer (not shown), adapter cables (not shown), and an External Monitor (not shown).

The external components of the Fitting System according to the present disclosure may be configured as follows. The battery (25) is connected with the VPU (20). The PTS Laptop (30) is connected to FS Laptop (10) using the CFS-PTS Cable (46). The PTS Laptop (30) and FS Laptop (10) are plugged into the Isolation Transformer (not shown) using the Adapter Cables (not shown). The Isolation Transformer is plugged into the wall outlet. The four (4) Port USB Hub (47) is connected to the FS laptop (10) at the USB port. The mouse (60) and the two Patient Input Devices (50) and (55) are connected to four (4) Port USB Hubs (47). The FS laptop (10) is connected to the Communication Adapter (CA) (40) using the CFS-CA Cable (45). The CA (40) is connected to the VPU (20) using the CA-VPU Cable (70). The Glasses (5) are connected to the VPU (20) using the Glasses Cable (15).

Figure 4:
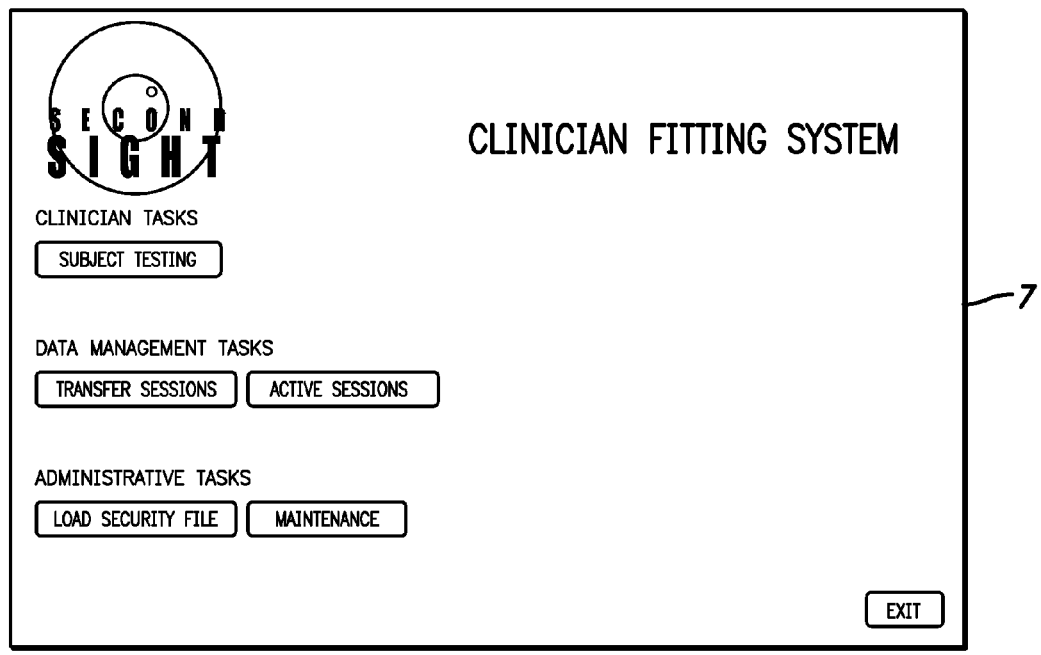
FIG. 4 shows a Main Menu computer screen.

The graphical user interface of the Fitting System may have six options on the FS Main Menu (7) as shown in FIG. 4. For example, Subject Testing, Transfer Session, Archive Sessions, Load Security File, Maintenance, and Exit.

The Subject Testing option may be selected when performing: diagnostic check (i.e. impedance and waveforms) on the status of the implant, viewing waveforms for selected electrodes, loading a video configuration file to the VPU and stimulating the subject using the downloaded video stimulation parameters, executing psychophysical experiments. The Transfer Session option may be selected when copying file(s) to a thumb drive. The Archive Sessions option may be selected when archiving all data files on the FS laptop (10) to the external drive (49). The Load Security File option may be selected to enable use of the Fitting System. The Load Security File option may be chosen at the initial clinical testing session. The Maintenance option may be selected to perform maintenance on one or more components of the system. The Maintenance option may be set up to only be accessed by an authorized person. The Exit option may be selected to close out the main menu.

The Subject Testing option is more fully described in the following paragraphs.

Prior to using a VPU (20) with a new subject for the first time, the following steps may be performed by an authorized person to configure the VPU (20): 1) Confirm that the VPU (20) is configured for use, 2) Match the VPU (20) to an implant, 3) Program the VPU (20) with the Subject's ID, and 4) Label the VPU (20) with the Subject's ID.

Prior using the Subject Testing option, the VPU (20) should be on, the subject should put on the Glasses (5), the Glasses (5) should be adjusted until a link is obtained with the implant, and the VPU (20) should confirm that the implant is working by running start-up tests.

Figure 5:
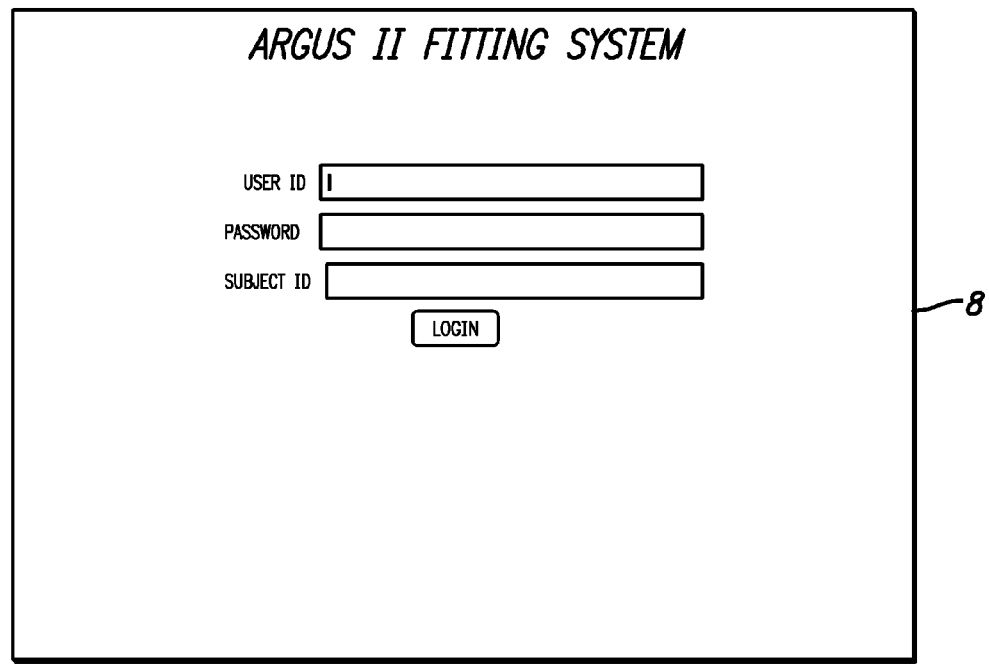
FIG. 5 shows a Login computer screen.

Once the Subject Testing option is selected from window (7), a login screen (8) shown in FIG. 5 may be displayed with fields for User ID, Password and Subject ID.

After the login, a diagnostic application may be initiated to display the status of the implant. Through the diagnostic application, an electrode integrity check may be performed and the electrode status may be displayed and the impedance and waveforms for each of the electrodes can be measured.

Figure 6:
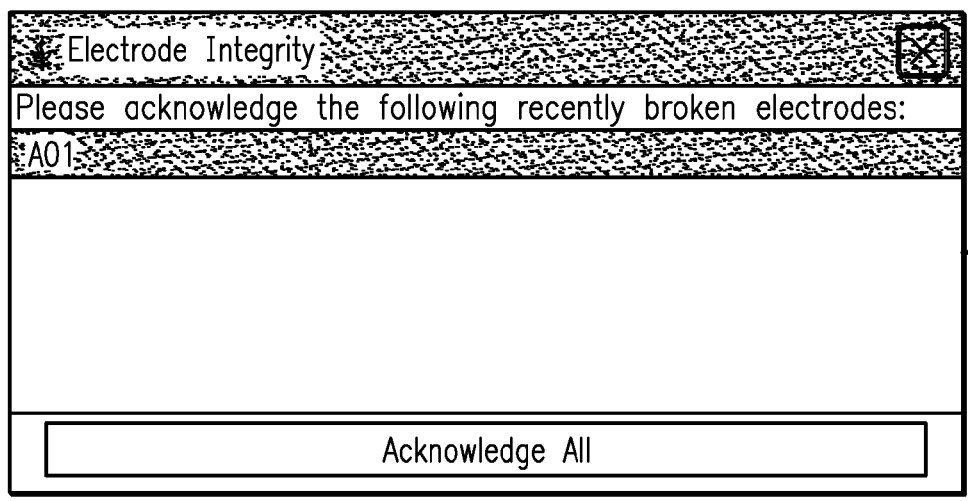
FIG. 6 shows an 'Electrode Integrity' message box.

An "Electrode Integrity' message box (6), shown in FIG. 6, may be displayed in the event that any newly broken/shorted electrodes are detected or broken/shorted electrodes are present. If no newly detected broken/shorted electrodes are detected, this message box will not appear and the diagnostics screen (109) shown in FIG. 7 may be displayed.

Figure 7:
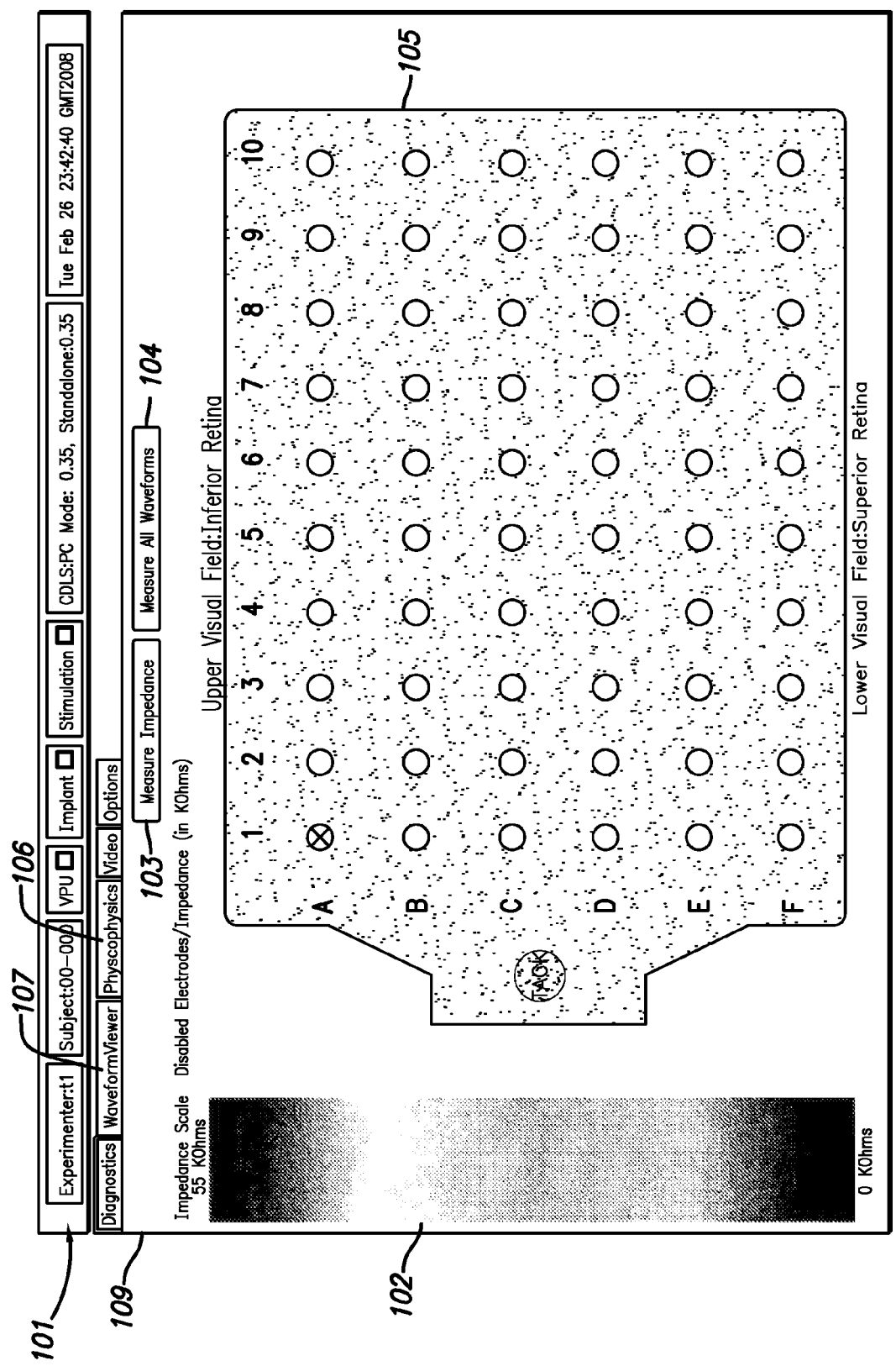
FIG. 7 shows a diagnostics computer screen.

The Diagnostic Module Screen (109) shown in FIG. 7 may contain: 1) Session Information (101) displaying (a) Experimenter (User) ID, (b) Subject ID, (c) VPU Connection identifying the status of the connection of the VPU to the FS, (d) Implant Connection identifying the status of the connection of the implant to the FS, (e) Stimulation identifying the status of stimulation (i.e., whether or not stimulation is occurring); (f) Charge Density Limit (CDL) in $mC/cm^2$ for both the PC and the stand alone modes; and (g) Date and Time 2) Measure Impedance (103) for measuring impedance for the electrodes;

3) Measure All Waveforms (104) for measuring waveforms for the electrodes; 4) Disabled Electrodes/Impedance (in kOhms)-6×10 Electrode Grid (105) representing each of the implant electrodes. The view of the electrodes is from the perspective of the subject. The electrodes shown as "⊗" are designated as broken/shorted. When measuring impedance, the values will appear directly under each represented electrode. Stimulation should not occur on electrodes designated as broken; and 5) Impedance Scale (102) for impedance that ranges from 0 to 55 kOhms.

Figure 8:
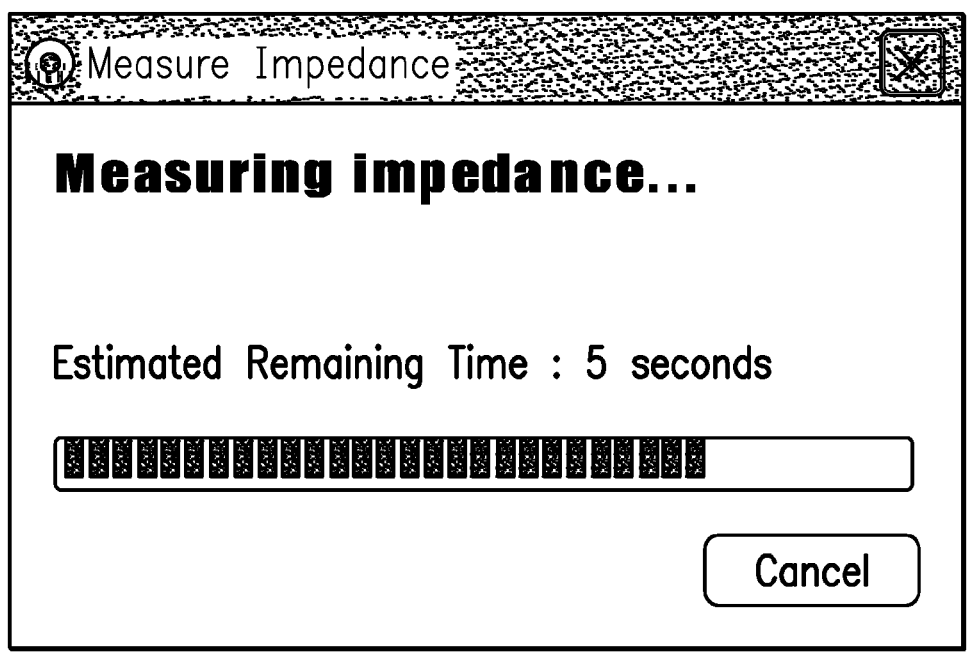
FIG. 8 shows a 'Measuring Impedance' message box.
Figure 9:
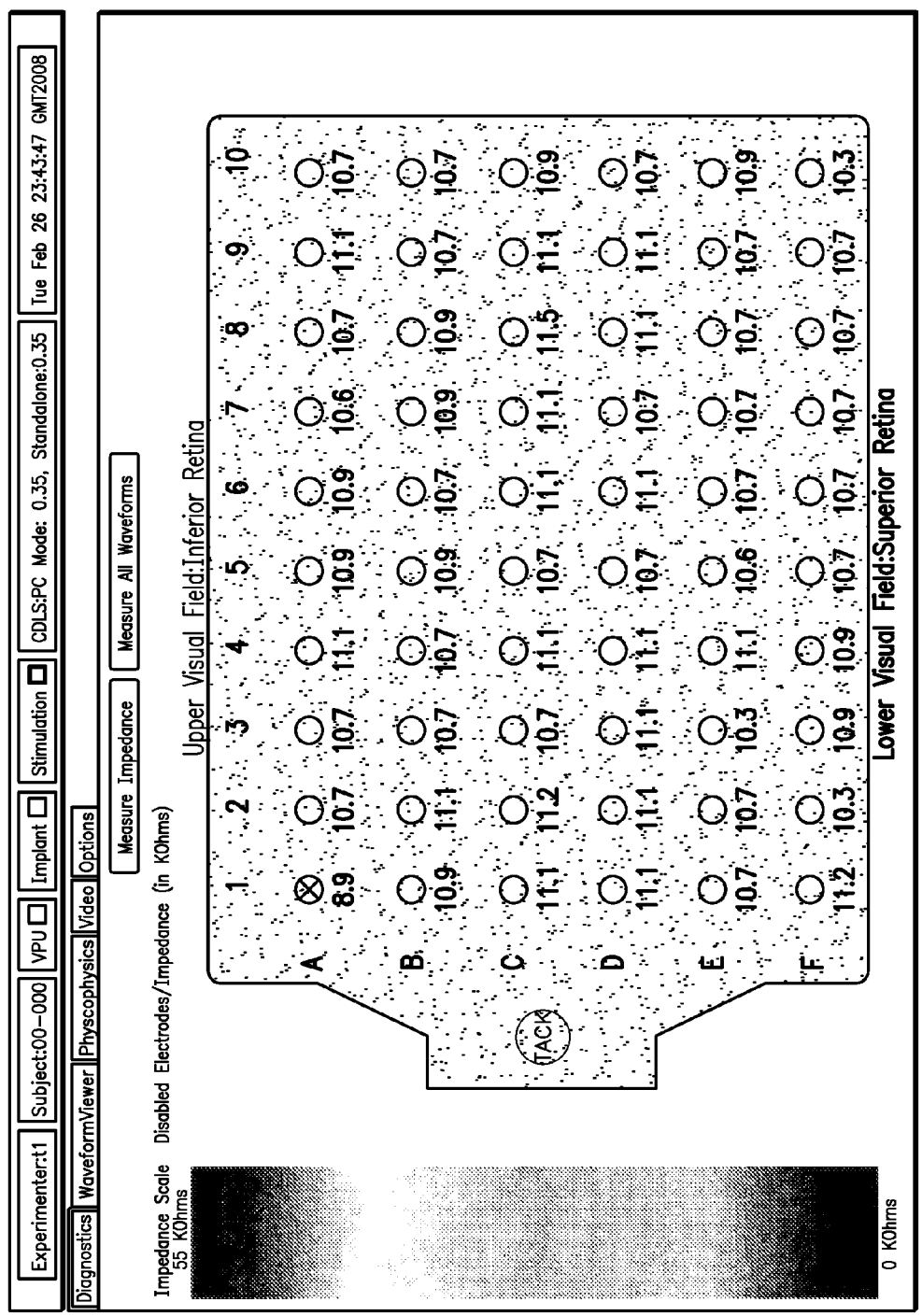
FIG. 9 shows a computer screen indicating impedance values.

Clicking on the Measure Impedance (103) will measure impedance of the electrodes and a message box shown in FIG. 8 may be used to indicate the progress of obtaining impedance measurements. Once the impedance measurements are completed, the impedance values (in kOhms) will be displayed as shown in FIG. 9 under each represented electrode. Each of the electrodes may be color coded based on where the impedance value falls within the impedance scale from 0 to 55 kOhms of the Impedance Scale (102) of FIG. 7. The impedance values for the subject may be automatically stored in a file marked for transfer on the FS laptop (10).

Figure 10:
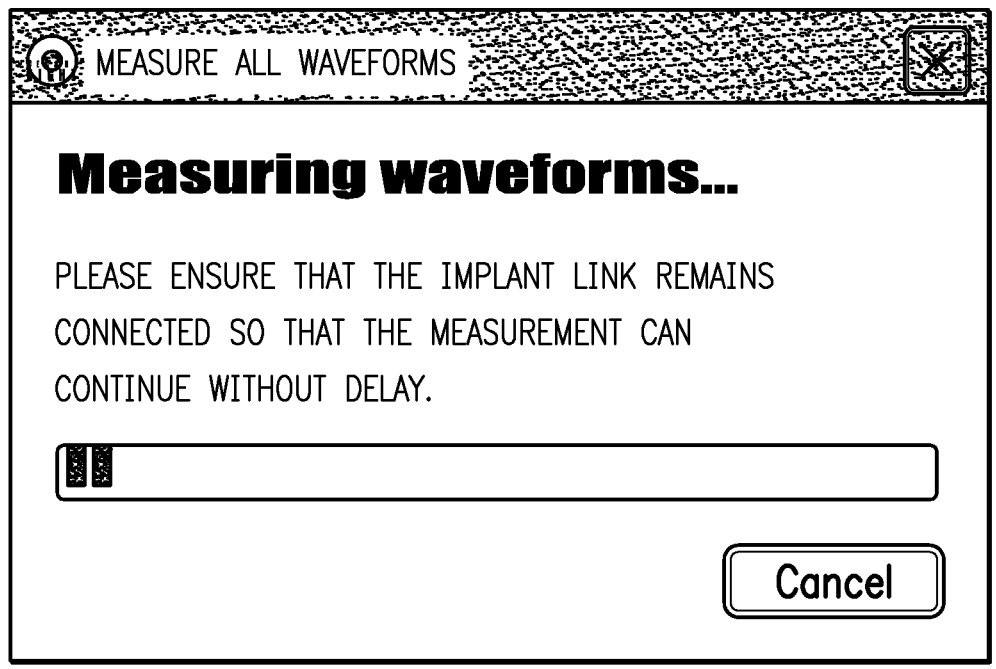
FIG. 10 shows a message box indicating progress of waveform measurements.

To measure waveforms, Clicking on "Measure All Waveforms" (104) button of FIG. 7 will measure waveforms of the electrodes and a message box shown in FIG. 10 may be used to indicate the progress of the waveform measurements. Once the measurements are complete, the waveform information may be stored in a file marked for transfer on the FS laptop (10). The waveforms for each of the electrodes can be viewed from the Waveform Viewer (107) tab shown in FIG. 7.

Figure 11:
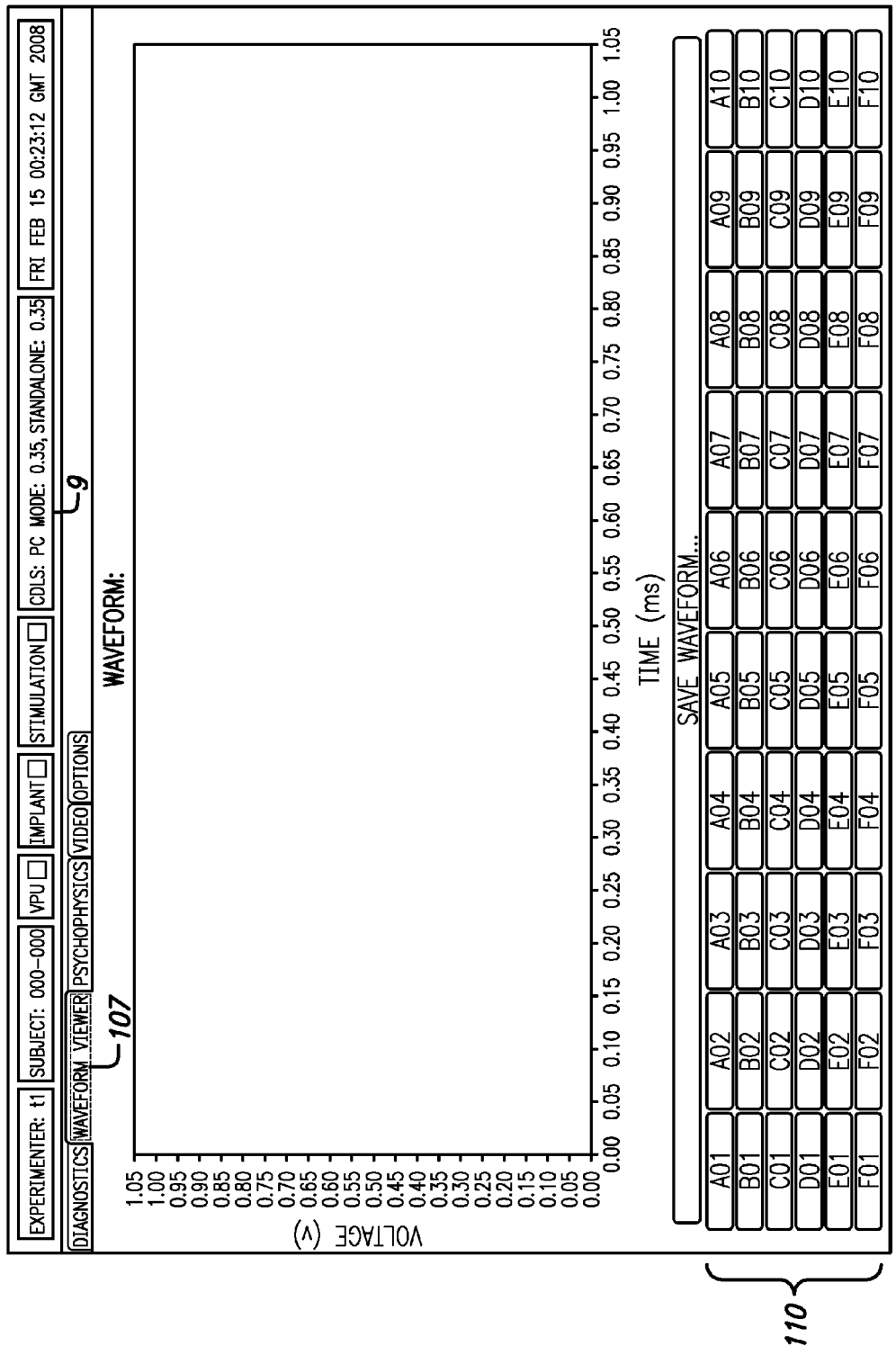
FIGS. 11 and 12 show waveform computer screens.
Figure 12:
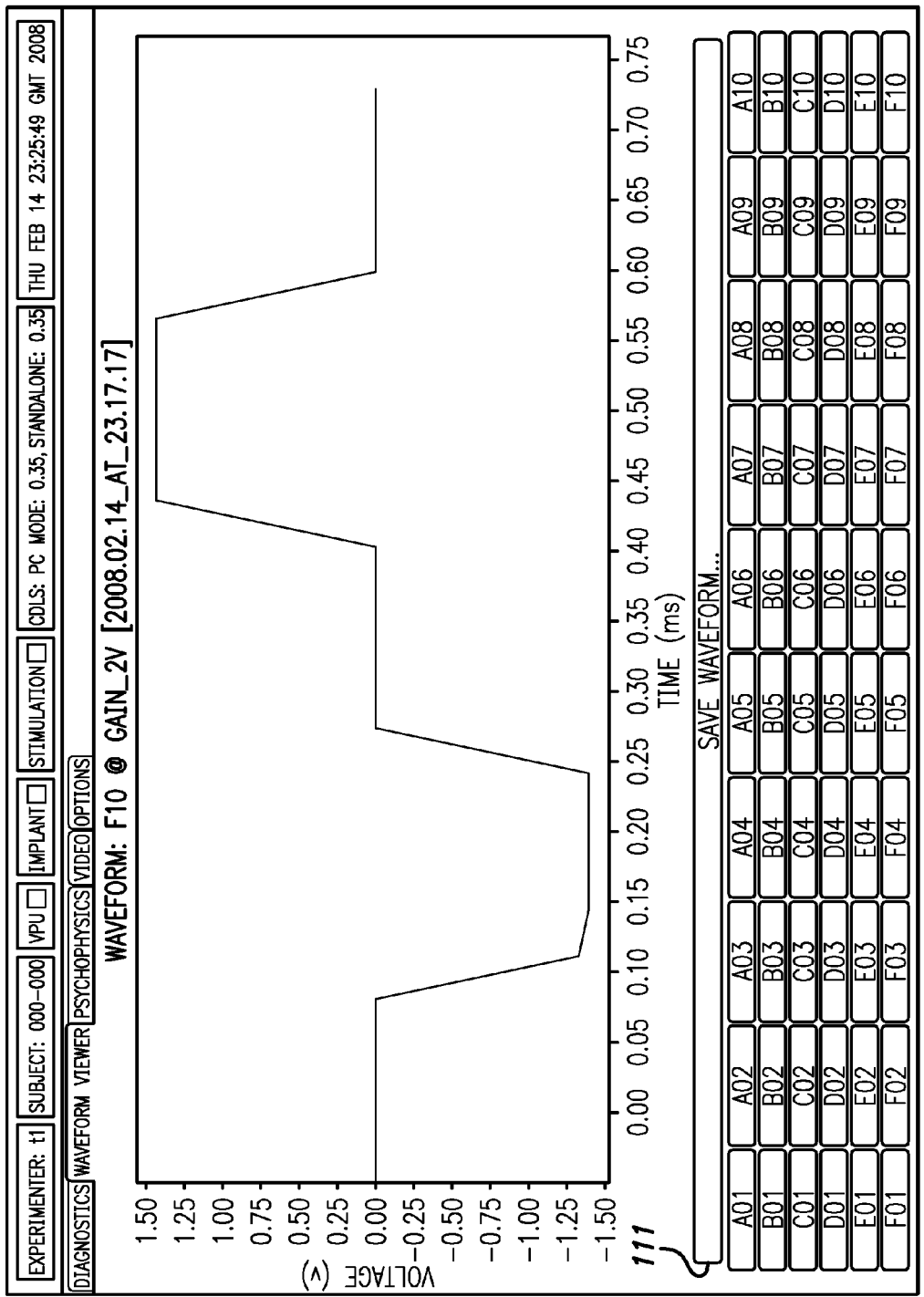

The Waveform Viewer (107) shown in FIG. 11 is a utility that may be used to measure and view the waveform of a selected electrode. From the list of the electrodes at the bottom of the screen (displayed in a 6×10 configuration (110) with their Cartesian coordinates), a specific electrode for which to measure the waveform may be selected. Upon selection of the electrode, the VPU (20) will record the waveform and the information will be sent to the FS so that the waveform data may be presented on the screen as shown in FIG. 12 in which, for example, the waveform of F10 is measured during stimulation. By right clicking on the mouse, it may be possible to zoom in and zoom out on the displayed waveform. The waveform may be saved by clicking on the Save Waveform button (111).

The Psychophysical Test System (PTS) is part of the Retinal Stimulation System (1) as it is intended to be used to facilitate fitting a subject by characterizing the subject's perceptual responses to electrical stimuli. The results from the psychophysical experiments may be accumulated, evaluated and used to determine the stimulation parameters of the VPU (20) during video stimulation.

Additionally, PTS may provide a framework for researchers and investigators to develop customized psychophysical experiments. PTS may comprise four ways to execute psychophysical experiments: 1) Threshold with Method of Adjustment, 2) Brightness Matching, 3) Direct Stimulation, and 4) Clinician-Designed Research Experiments. Each being described in detail below.

The Threshold with Method of Adjustment may be used to determine the stimulation current threshold for an individual electrode (i.e. the stimulation level at which a percept is first seen). The user interface allows the experimenter to (1) configure the experiment, including which electrodes to test, how many trials are tested per electrode and other stimulation timing parameters, (2) preview the stimulation waveform, (3) capture subject responses, and (4) view experiment results on the screen as the test progresses, and save the results.

In this test, the subject will be stimulated on one of the test electrodes. The subject may use the Patient Input Device (Jog Dial) (55) shown in FIG. 3 to increase or decrease the stimulation current amplitude on the selected electrode after each stimulation. To indicate the threshold, the subject may press down the Jog Dial (55) when perception occurs. The Results screen displays the threshold and another test electrode is tested. This continues until all selected electrodes are tested for a number of trials, as configured by the experimenter. All stimulation parameters may be recorded by the Fitting System in the psychophysics log.

The Brightness matching may be used to determine the relationship between electrode stimulation current and the perceived brightness. These data are analyzed to determine the current amplitudes required to elicit the same perceived brightness for each electrode in the array. The user interface allows the experimenter to (1) configure the experiment, including which electrodes to test, which electrode and what amplitude to use as a reference, how long to wait between the two stimuli, the number of trials per test electrode, and other stimulation timing parameters, (2) preview the stimulation waveform, and (3) view the stimulation and subject response as the test progresses.

In each trial, the subject may be stimulated with two stimuli, one on the test electrode and one on the reference electrode (The order of the stimuli is random). The subject may use the keys on the Patient Input Device (Tablet) (50) shown in FIG. 3 to signal which of the two temporal intervals contains the brighter stimulus. This process will continue until each of the selected electrodes has been tested for a number of trials, as configured by the experimenter.

Using Direct Stimulation, an experimenter is able to (1) design a stimulation wave form on a single or multiple electrodes and (2) conduct manual testing on a single or multiple electrodes. During the use of Direct Stimulation, no subject response is automatically logged in FS.

The PTS System, may, for example, also have MATLAB software installed to allow clinicians to develop their own customized psychophysical experiments for research purposes. These experiments may be used for research purposes.

Figure 13:
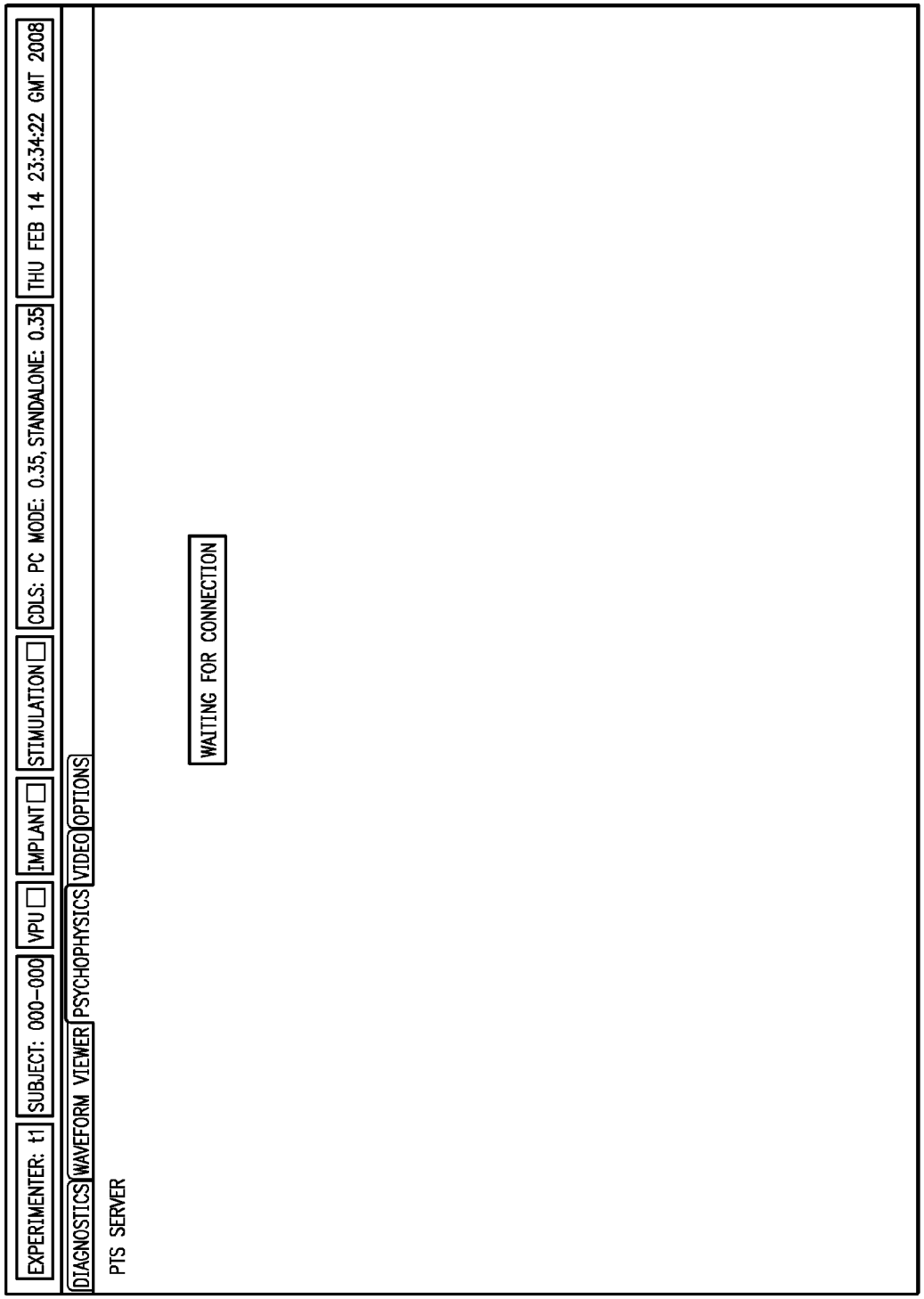
FIG. 13 shows a 'waiting for connection' message box.

The following provides instructions for running the Threshold Method of Adjustment, Brightness Matching, and Direct Stimulation Psychophysical experiments. By selecting the Psychophysics tab (106) of FIG. 7, FS will attempt to connect with PTS. "WAITING FOR CONNECTION," as shown in FIG. 13 may be displayed indicating that FS is waiting for a connection with PTS.

Figure 14:
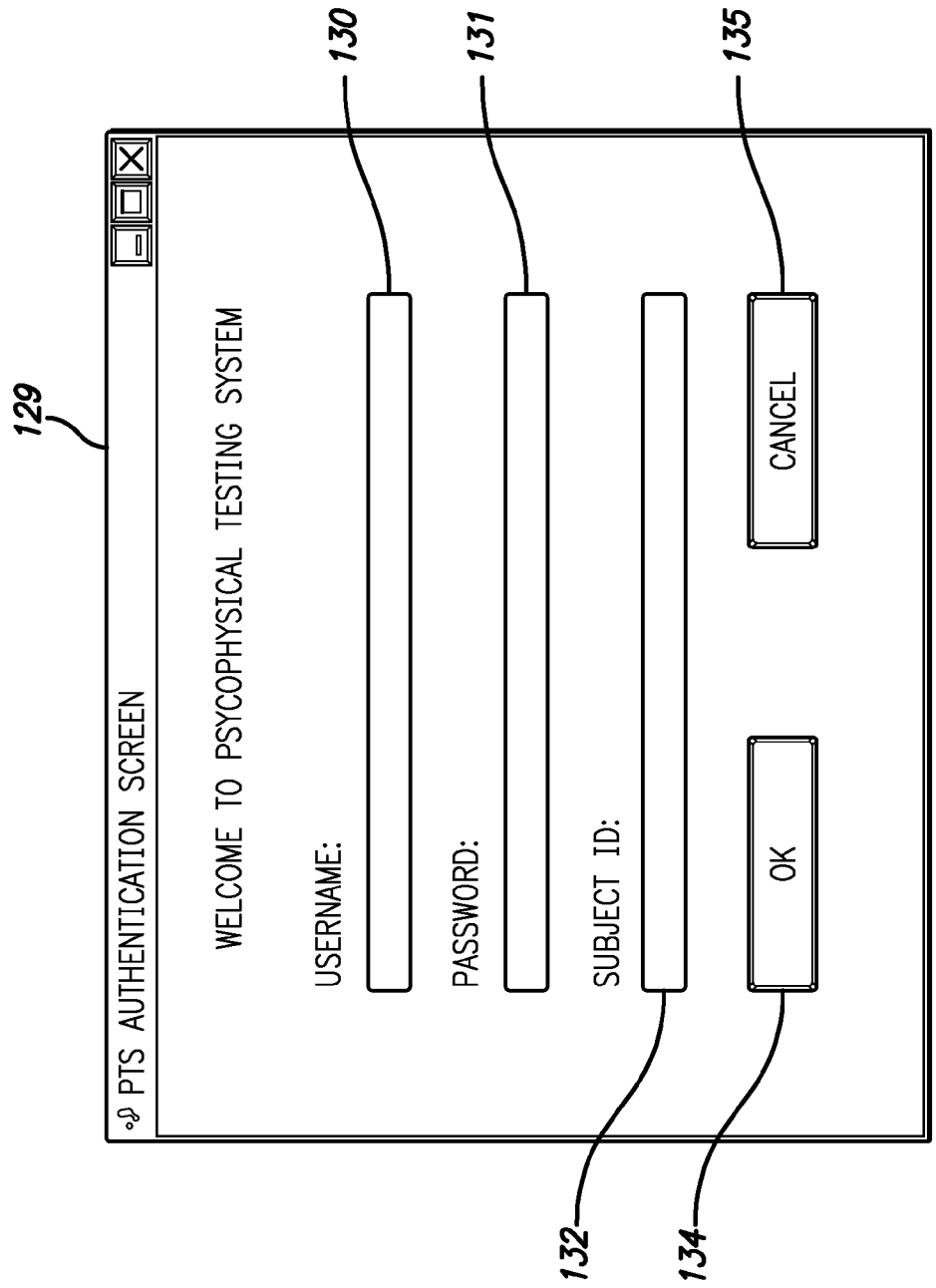
FIG. 14 shows a computer window requesting specific information.

A window (129) shown in FIG. 14 will appear on the PTS laptop (30) of FIG. 3 requesting Username (130), Password (131), and Subject ID (132). 'OK' (134) may be used to proceed to the Psychophysical Test System Main Menu and 'Cancel' (135) may be used to quit the session.

Figure 15:
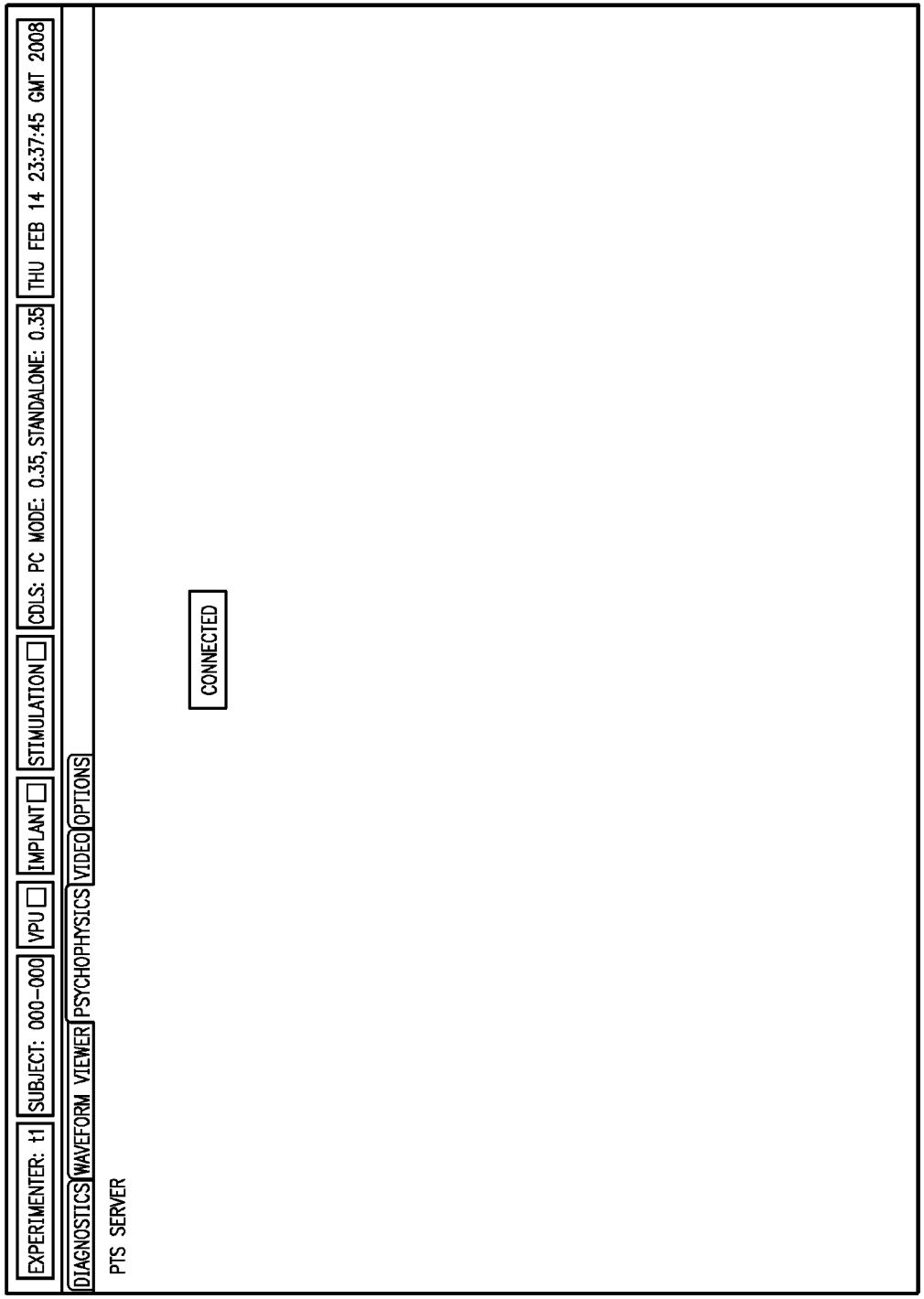
FIG. 15 shows a 'connected' message box.

If 'OK' (134) is selected, the PTS Server screen on the FS Laptop (10) of FIG. 3 should display "CONNECTED", as shown in FIG. 15, to indicate that a connection has been successfully established between the FS and PTS.

Figure 16:
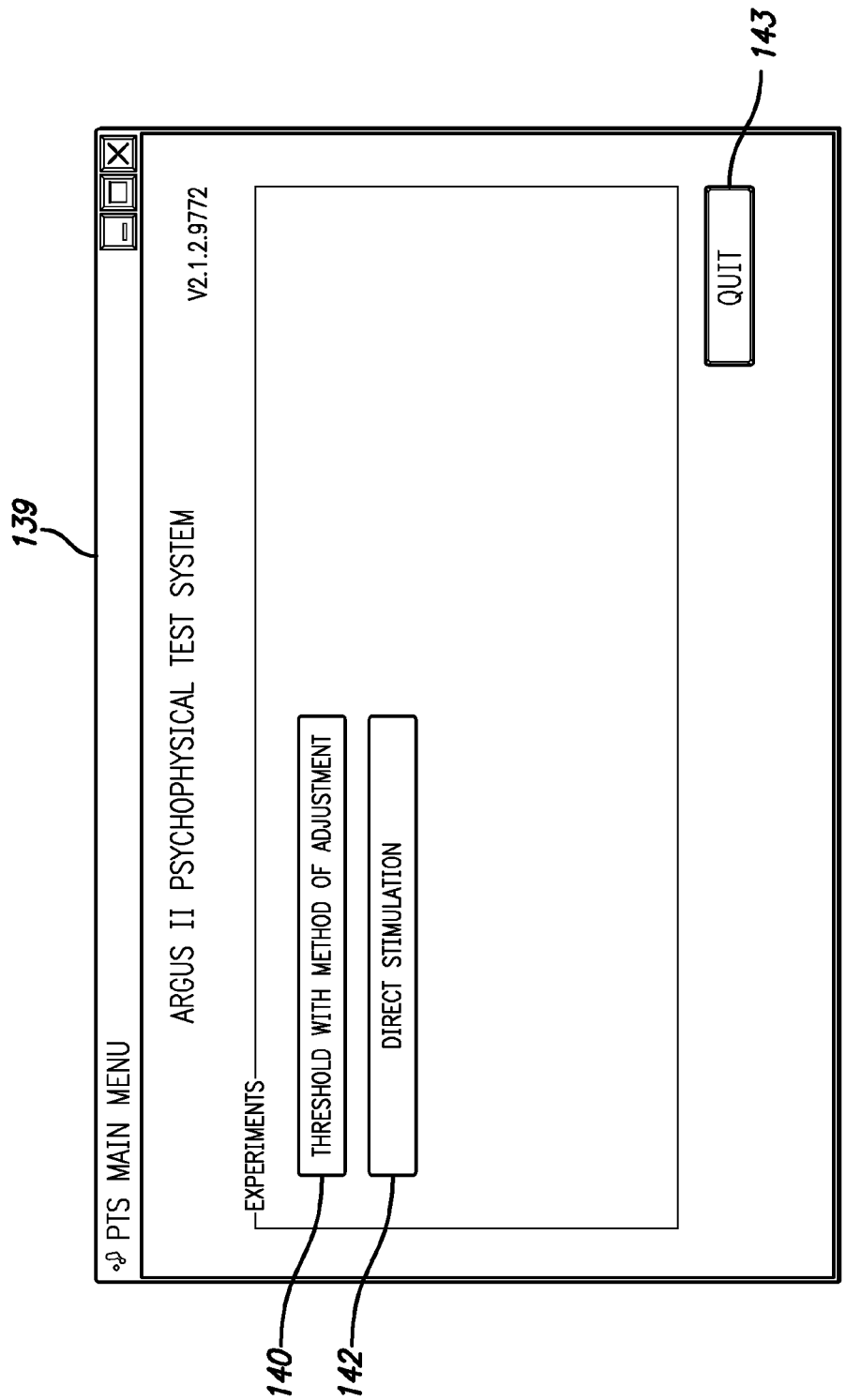
FIG. 16 shows a Psychophysical Test System (PTS) main screen.

The Psychophysical Test System (PTS) main screen (139), shown in FIG. 16, has three options 1) 'Threshold with method of adjustment' (140), 2) 'Direct Stimulation' (142), and 3) 'Quit' (143).

Next, a way of conducting a threshold measurement using the method of adjustment will be described.

Figure 17:
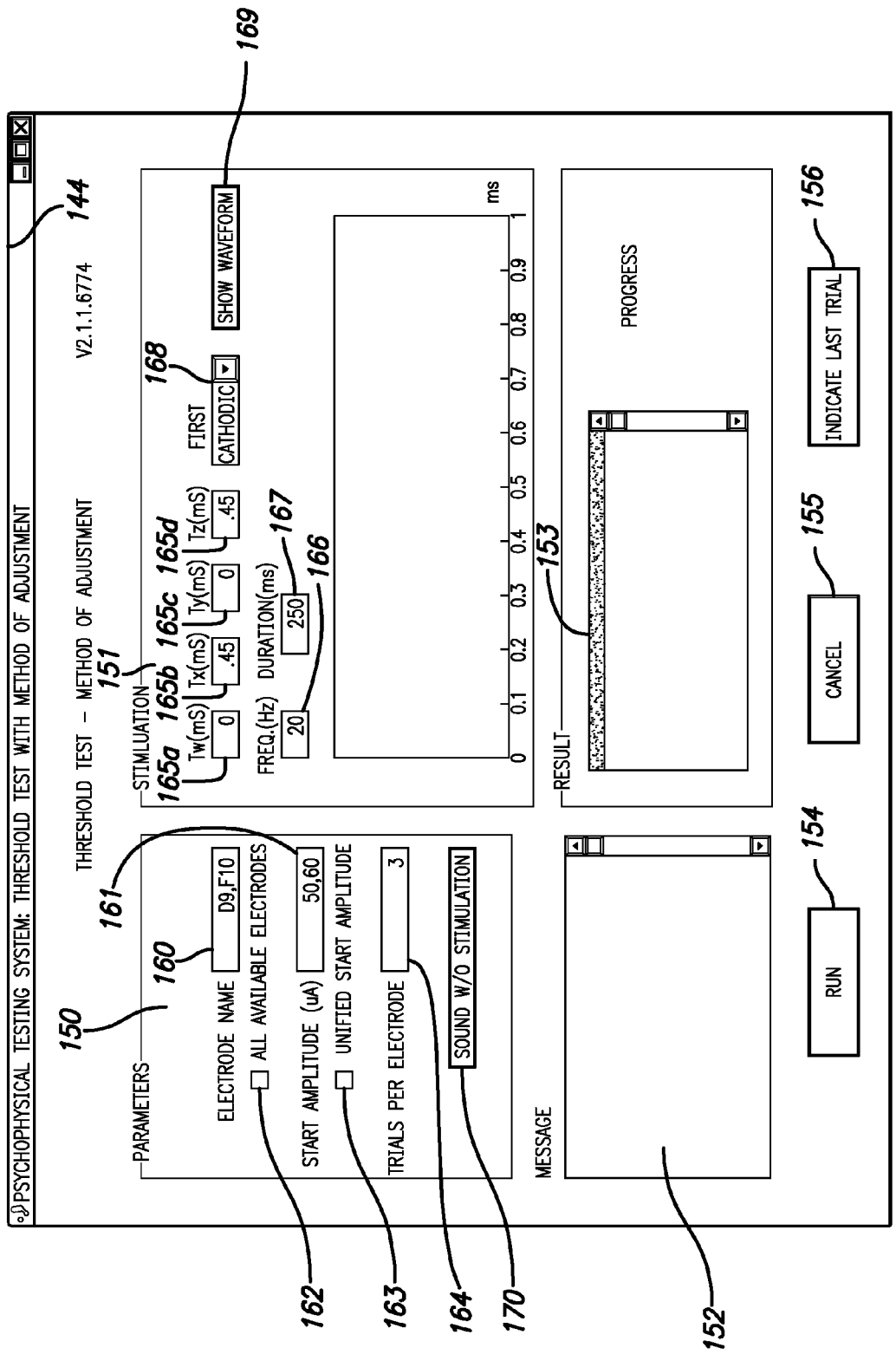
FIG. 17 shows a 'Threshold with Method of Adjustment' screen.

A 'Threshold with Method of Adjustment' screen (144) shown in FIG. 17 appears when the 'Threshold Method of Adjustment' button (140) is selected from the 'PTS Main Menu' screen (139) of FIG. 16. The 'Threshold with Method of Adjustment' screen (144) may contain:

1) a 'Parameters' panel (150) for experiment parameters that require configuration in order to execute an experiment, 2) a 'Stimulation' panel (151) for stimulation parameters that require configuration in order to execute an experiment;

3) a 'Message' panel (152) for messages that may require the experimenter's attention during the testing. There are two types of messages than can be displayed during a test session: (a) Unknown key pressed—This message is generated if the subject presses an unknown key during the test, and (b) Maximum or minimum amplitude reached—This message is generated if the maximum/minimum current amplitude is reached (as allowed by the maximum charge per phase safety limit) and the subject continues to turn the jog dial to increase/decrease the amplitude. A loud sound may also be emitted to alert the experimenter and the subject;

4) a 'Result' panel (153) for displaying electrodes that are currently under test, stimulation amplitude and previously recorded thresholds in this experiment;

5) a 'Run' button (154) to start to run the threshold with method of adjustment experiment. The program will check the parameters entered against the safety limits and the experimenter will have a chance to correct them if so;

6) a 'Cancel' button (155) to cancel the current running experiment; and 7) an 'Invalidate Last Trial' button (156) to invalidate the last found threshold if the subject pushed the jog dial by accident.

Configuration parameters may be entered for the experiment as described below, with continued reference to FIG. 17.

The names of electrode(s) whose thresholds are to be measured during testing may be entered in the 'Electrode Name' window (160) of the 'Parameters' panel (150). One may select all the electrodes by selecting the 'All Available Electrodes' option (162) of the 'Parameters' panel (150) or one may select only certain electrodes from the grid shown in a Table 1 below.

TABLE 1

| A1 | A2 | A3 | A4 | A5 | A6 | A7 | A8 | A9 | A10 |
| B1 | B2 | B3 | B4 | B5 | B6 | B7 | B8 | B9 | B10 |
| C1 | C2 | C3 | C4 | C5 | C6 | C7 | C8 | C9 | C10 |
| D1 | D2 | D3 | D4 | D5 | D6 | D7 | D8 | D9 | D10 |
| E1 | E2 | E3 | E4 | E5 | E6 | E7 | E8 | E9 | E10 |
| F1 | F2 | F3 | F4 | F5 | F6 | F7 | F8 | F9 | F10 |

The starting stimulation amplitude(s) (µA) for each of the test electrodes may be entered in the 'Start Amplitude' window (161) of the 'Parameters' panel (150). A 'Unified Start Amplitude' option (163) of the 'Parameters' panel (150) may be checked to enter a single Start Amplitude for all electrodes.

The number of threshold measurements to be made on each electrode may be entered in the 'Trials per electrode' window (164) of the 'Parameters' panel (150).

Figure 18:
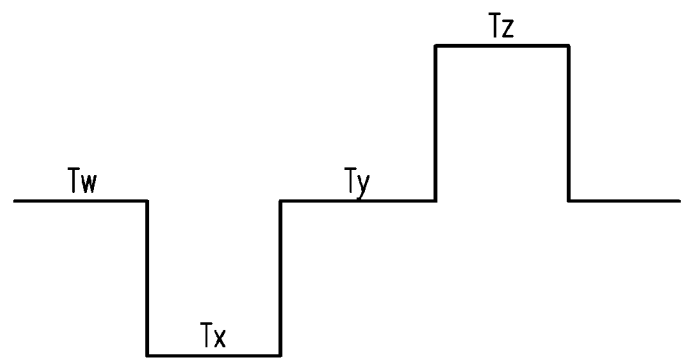
FIG. 18 shows a waveform related to FIG. 17.

The pulse Width (ms) may be entered into windows (165a-d) of the 'Stimulation' panel (151). The desired time between start of the effective stimulation window and initiation of the first phase may be entered into a Tw window (165a). The duration of the first phase may be entered into a Tx window (165b). The desired time between the end of the first phase and the beginning of the second phase may be entered into a Ty window (165c). The duration of the second phase may be entered into a Tz window (165d). FIG. 18 depicts a waveform of the numbers entered into windows (165a-d).

Figure 19:
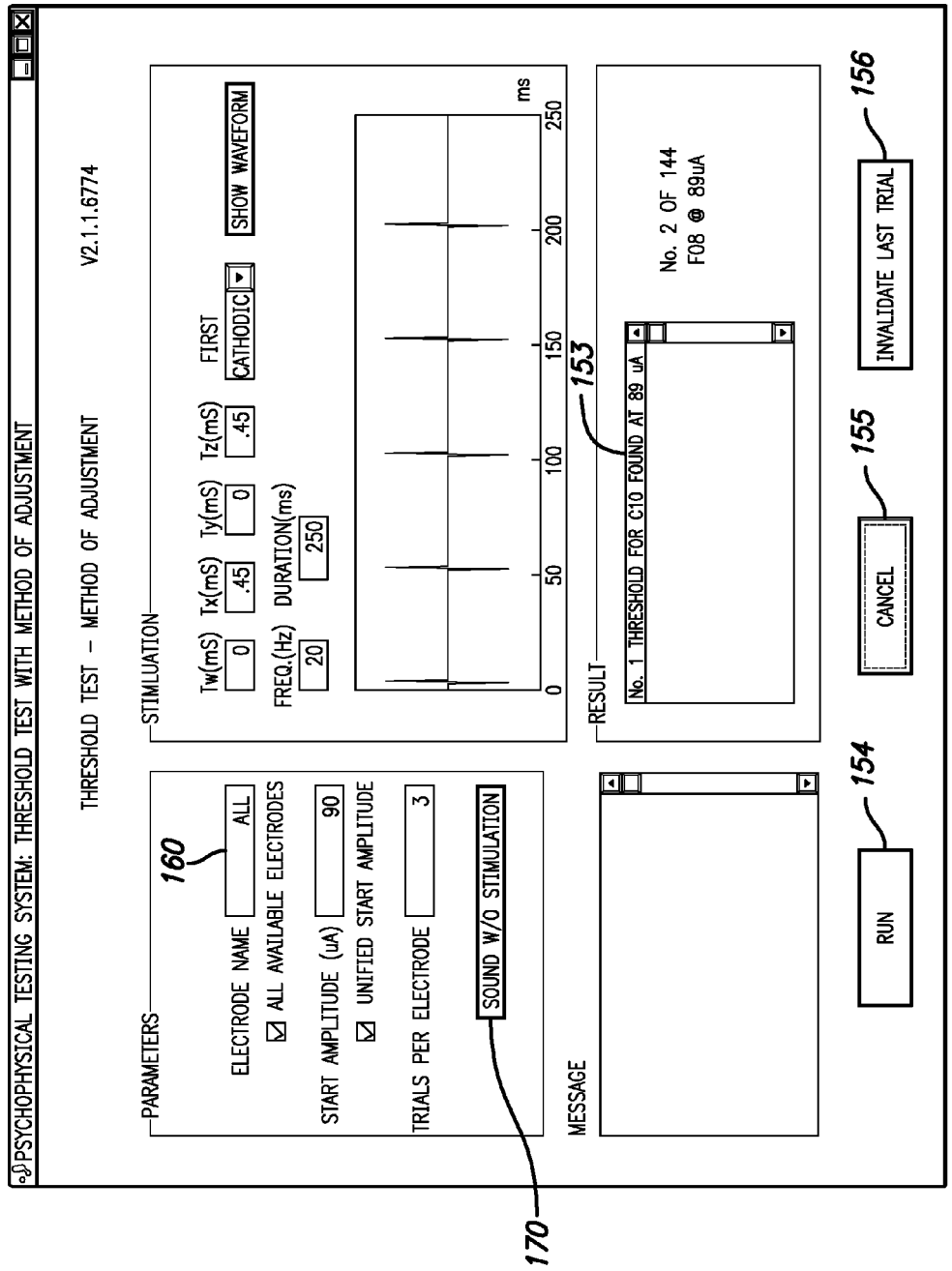
FIG. 19 shows a 'Threshold Test' computer screen.

The frequency of how many times per second the waveform shown in FIG. 18 will be repeated may be entered into a 'Frequency' window (166) of the 'Stimulation' panel (151) of FIG. 17. The desired length of each stimulation in milliseconds (i.e. the length of stimulation at a given test amplitude) may be entered into a 'Duration' window (167) of the 'Stimulation' panel (151). Selection of whether the first phase is negative (cathodic) or positive (anodic) current may be performed using 'First' window (168) of the 'Stimulation' panel (151). A 'Show waveform' button (169) may be used to produce a graph that plots the waveform of the complete stimulus for a trial. A 'Sound w/o stimulation' button (170) may be used to generate a sound (the same as the one heard when stimulation is delivered) without actually delivering stimulation. Once all configuration parameters have been entered, the experimenter has the option to press the 'Show Waveform' button (169) prior to initiating the experiment to check the parameters to produce a graph that plots the waveform of the complete stimulus for a trial as shown in FIG. 19. A 'Run' button (154) may be used to proceed with the experiment.

Figure 20:
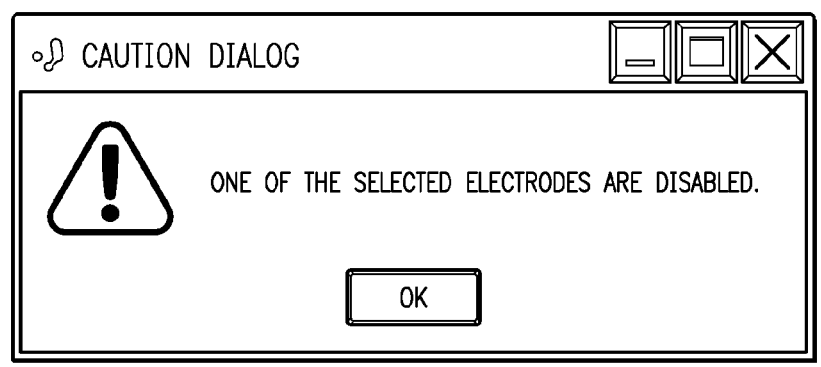
FIGS. 20 and 21 show warning dialog message boxes.
Figure 21:
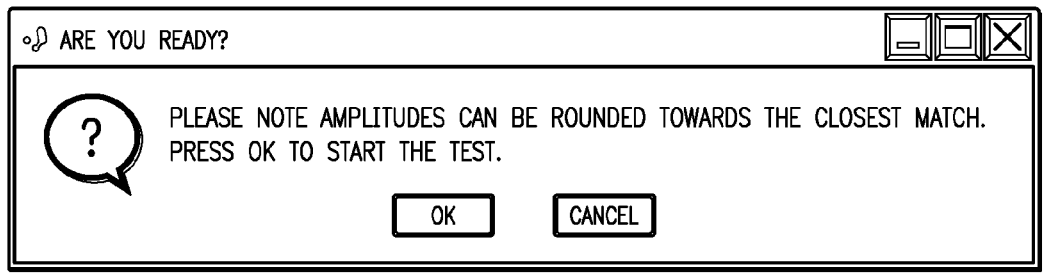

After the 'Run' button (154) or 'Show Waveform' button (169) are activated, the parameters may be checked against safety requirements of the system. If any of the parameters violates safety limits, a message box may be displayed and the experimenter will need to change the configuration parameters. Common errors may include broken/shorted electrodes and start amplitudes which exceed maximum charge per phase limit. For example, if any of the chosen electrodes are already deemed broken/shorted, a popup message shown in FIG. 20 may be displayed on the screen. If no safety violations are found, a popup message shown in FIG. 21 will appear. If the requested pulse amplitude cannot be generated by the VPU (20) of FIG. 3, the closest value will automatically be used. The value will appear in the results section discussed below.

After each stimulus presentation, the subject may turn the jog dial (55) of FIG. 3 to the right to increase stimulation amplitude, or may turn the jog dial (55) to the left to decrease stimulation amplitude. The subject may increase or decrease the stimulation level until he/she has determined their threshold (i.e. the minimum stimulation amplitude for seeing the stimulation.) The subject may signal the threshold for that electrode by pressing down on the Jog Dial (55). If multiple electrodes are tested, the electrodes may be tested in random order.

Figure 22:
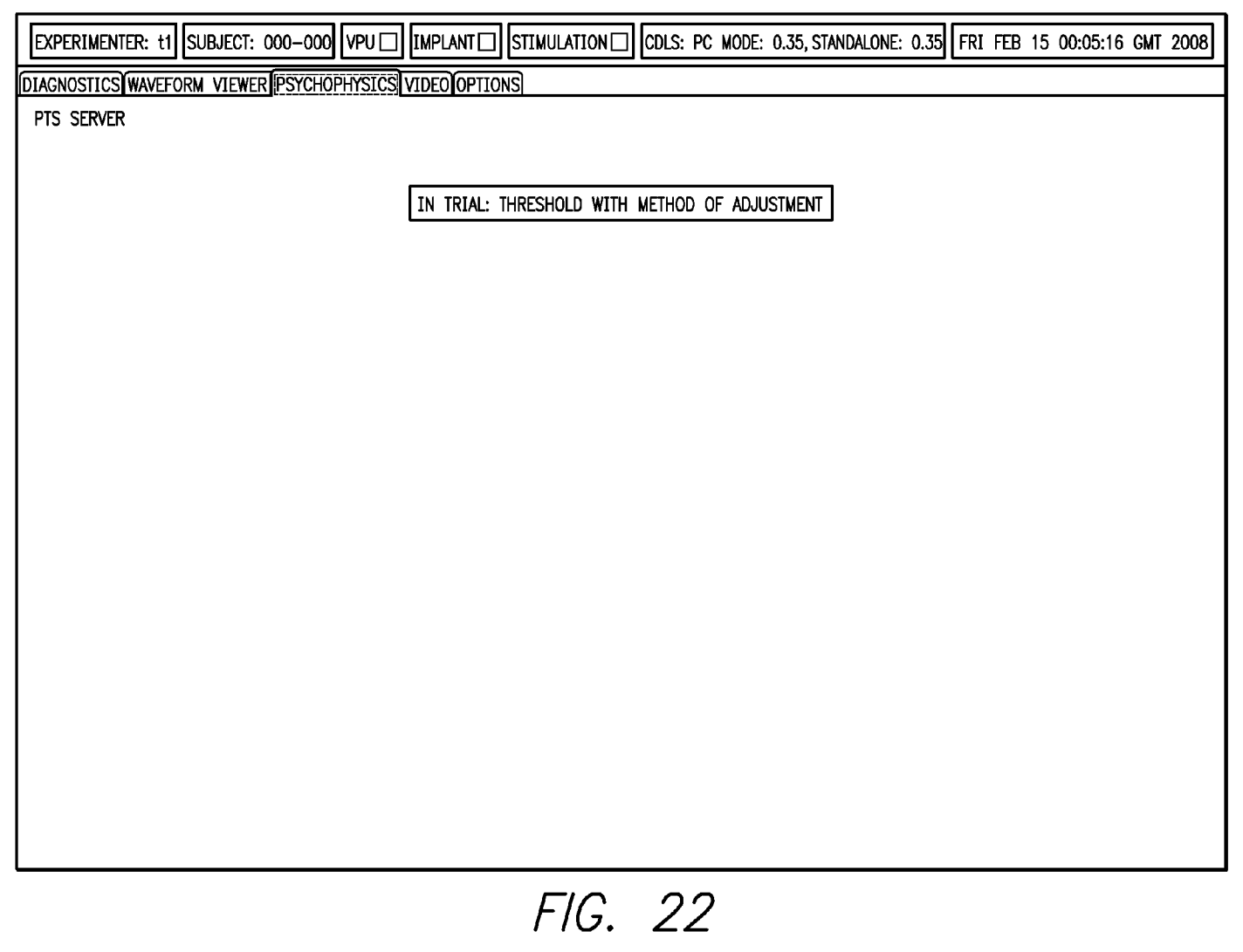

During a Threshold with Method of Adjustment experiment, the PTS Server screen on the FS Laptop (10) may display 'IN TRIAL: Threshold with method of adjustment' is shown in FIG. 22. At any time during the experiment, the experimenter can click the 'Sound w/o stimulation' button (170) of FIG. 17 or 19 to generate a stimulation sound without actually delivering stimulation to the subject.

If for any reason, the experimenter determines that the last threshold measurement is invalid (e.g. the subject pressed down the jog dial (55) accidentally), the experimenter can click on the 'Invalidate Last Trial' button (156) of FIG. 17 or 19 to invalidate that trial. This may be set up to invalidate only the results of the last trial, not the whole experiment. The 'Result' panel (153) of FIG. 17 or 19 will show the trial as "Invalid" and the trial will be repeated in a random order with the remaining electrodes.

The experiment ends once all of the trials have been completed. In the 'Result' panel (153), the total number of trials and number of finished trials may be displayed throughout the experiment. The 'Cancel' button (155) may be used to stop an experiment prior to the completion of all trials.

Figure 23:
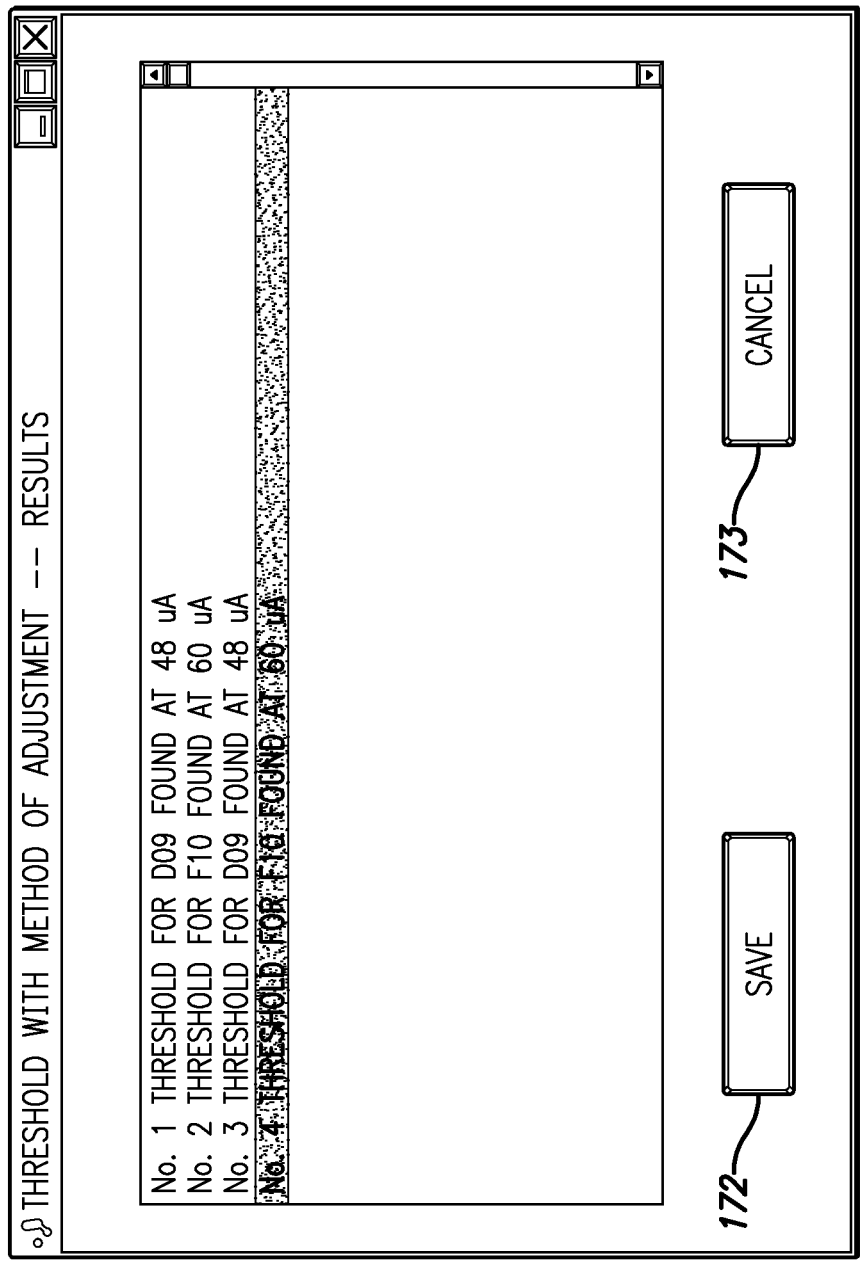
FIG. 23 shows a 'Threshold Test with Method of Adjustment' message box.

At the end of the experiment, the "Threshold with method of adjustment-results" screen shown in FIG. 23 may appear and the experimenter may have the option of saving the results to a hard drive.

Figure 24:
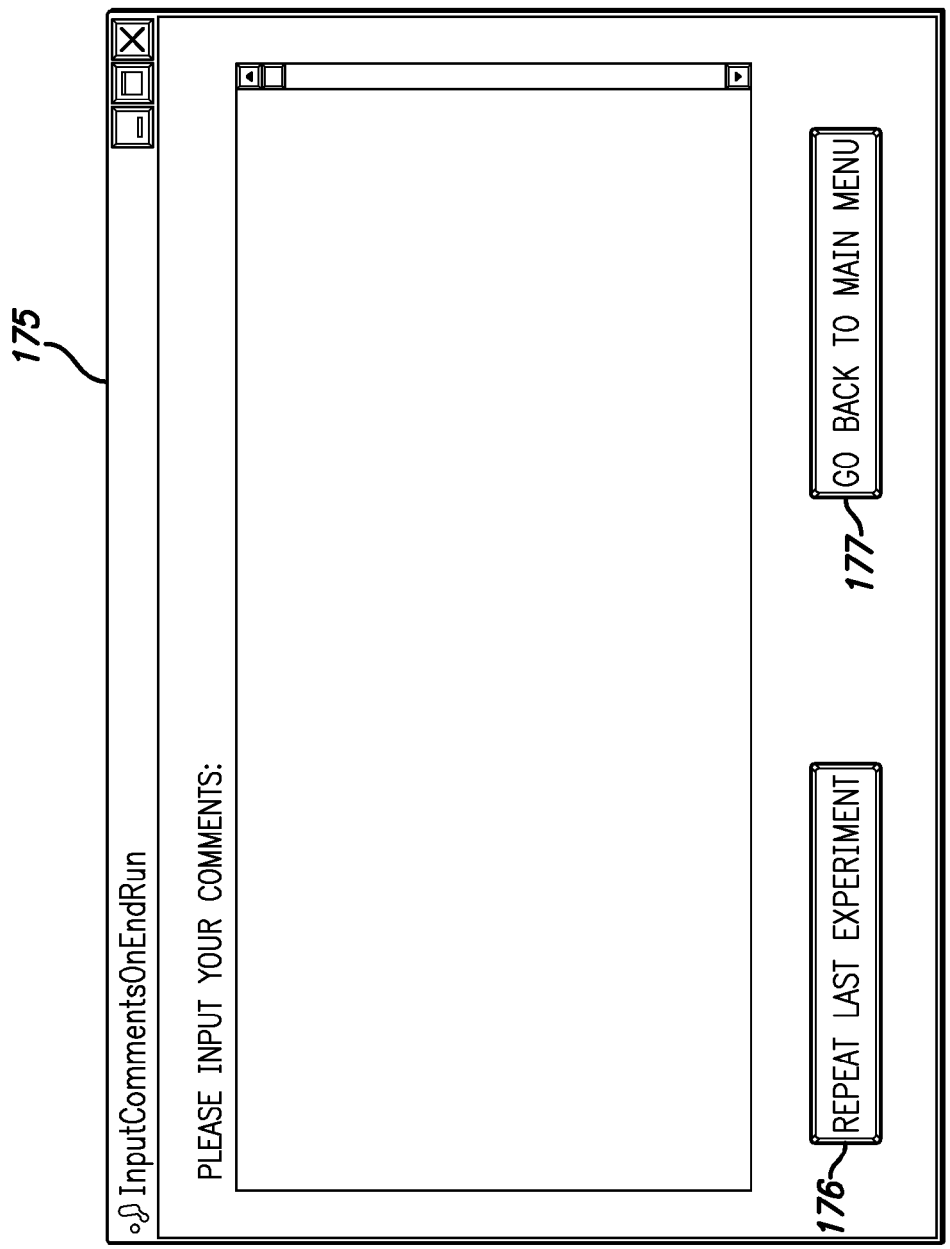
FIG. 24 shows an 'Input Your Comments' message box.

After saving the results (172) and/or canceling (173), a 'Comment' screen (175) shown in FIG. 24 may be used for comments. The 'Comment' screen (175) contains two buttons, 'Repeat Last Experiment' (176) and 'Go Back to Main Menu' (177). If 'Repeat Last Experiment' (176) is chosen, the experimenter will be returned to the main Threshold Test-'Method of Adjustment' screen (144) of FIG. 17 with the Parameters from the last experiment and the experimenter can modify and repeat the experiment. If 'Go Back to Main Menu' (177), is chosen, the experimenter will be returned to the main PTS menu (139) of FIG. 16.

Figure 25:
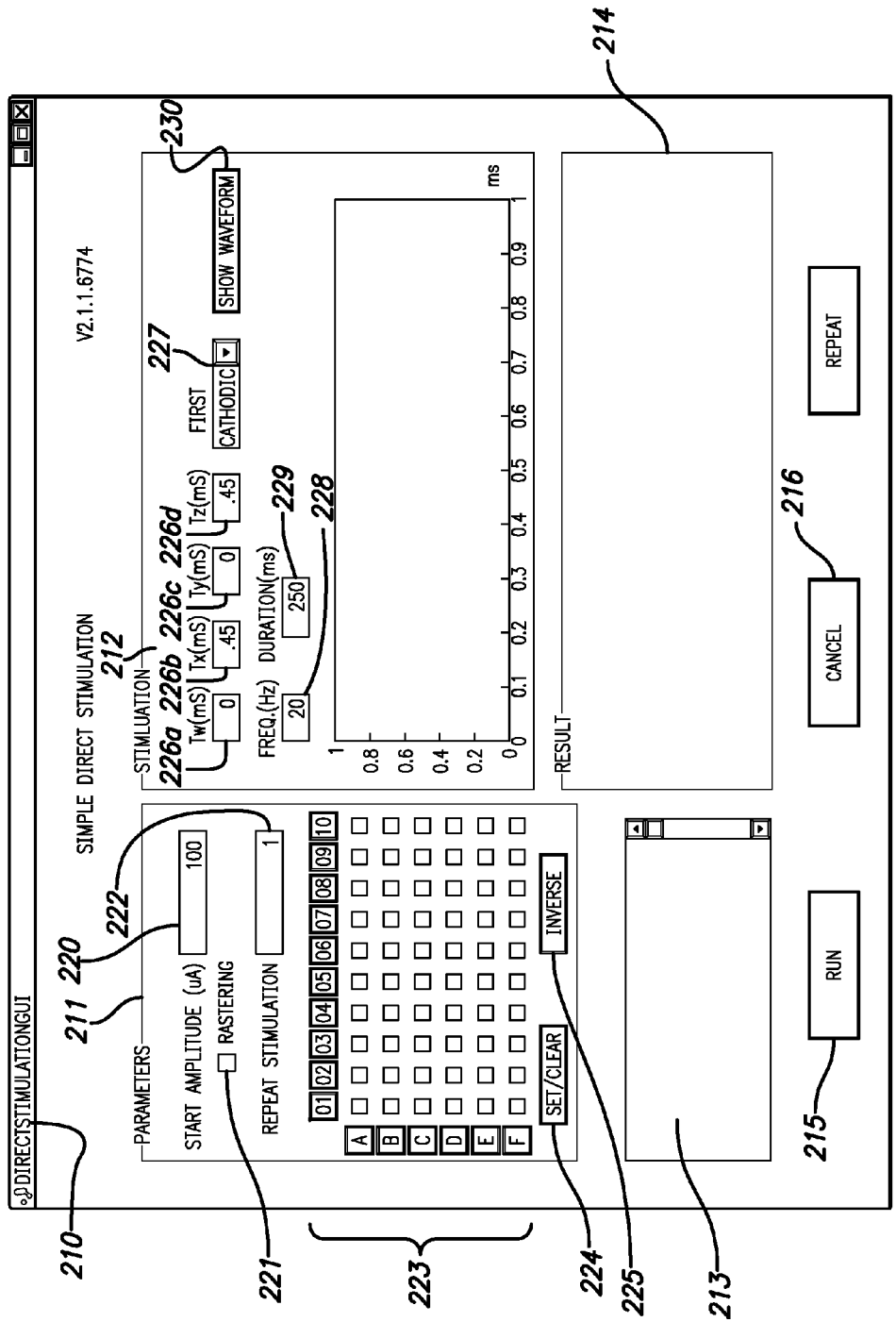
FIG. 25 shows a 'Simple Direct Stimulation' computer screen.

A 'Direct Stimulation' screen (210) shown in FIG. 25 appears when the 'Direct Stimulation' button (142) of FIG. 16 is selected from the PTS Main Menu Screen (139) of FIG. 16. The 'Direct Stimulation' screen (210) may also contain 1) 'Parameters' panel (211), 2) 'Stimulation' panel (212), 3) 'Message' panel (213), and 4) 'Result' panel (214). During a Direct Stimulation experiment, the PTS Server screen on the FS Laptop (10) may display "EXPERIMENT: Direct Stimulation" as shown in FIG. 27.

Configuration parameters may be entered for the experiment as described below with reference to FIG. 25.

Starting stimulation amplitude(s) (μA) for each of the selected electrodes may be entered into a 'Start Amplitude' window (220) of the 'Parameters' panel (211). 'Rastering' (or timing) (221) may be used to stagger the start times that electrodes are stimulated. When this option is not selected, all electrodes are stimulated simultaneously.

The number of times a stimulation will be repeated may be entered into a 'Repeat Stimulation' window (222) of the 'Parameters' panel (211). The time delay between successive repetitions may be approximately 0.5 seconds.

The electrodes to be stimulated can be selected from the 'Electrodes' windows (223) of the 'Parameters' panel (211). The electrodes may be individually selected by clicking individual boxes. Complete rows of electrodes may be selected or de-selected by clicking on the alphabetic button (A-F). Complete columns of electrodes may be selected or de-selected by clicking on the numeric button (01-10). All electrodes can be selected by using the 'Set/Clear' button (224). The inverse of the selected electrodes can be achieved by clicking on the 'Inverse' button (225).

A Pulse Width (ms) may be entered into windows (226a-d) of the 'Stimulation' panel (212). A desired time between start of the effective stimulation window and initiation of the first phase may be entered into a Tw window (226a). The duration of the first phase may be entered into a Tx window (226b). The desired time between the end of the first phase and the beginning of the second phase may be entered into a Ty window (226c). Duration of the second phase may be entered into a Tz window (226d). FIG. 18 depicts a possible waveform of the numbers entered into windows (226a-d).

The frequency of how many times per second the waveform shown in FIG. 18 will be repeated may be entered into a 'Frequency' window (228) of the 'Stimulation' panel (212). A desired length of each stimulation in milliseconds (i.e. the length of stimulation at a given test amplitude) may be entered into a 'Duration' window (229) of the 'Stimulation' panel (212). Selection of whether the first phase is a negative (cathodic) current phase or a positive (anodic) current phase may be performed using the first window (227) of the 'Stimulation' panel (212). The 'Show Waveform' button (230) may be used to produce a graph that plots the waveform of the complete stimulus for a trial. The 'Run' button (215) may be used to proceed with the experiment.

Figure 26:
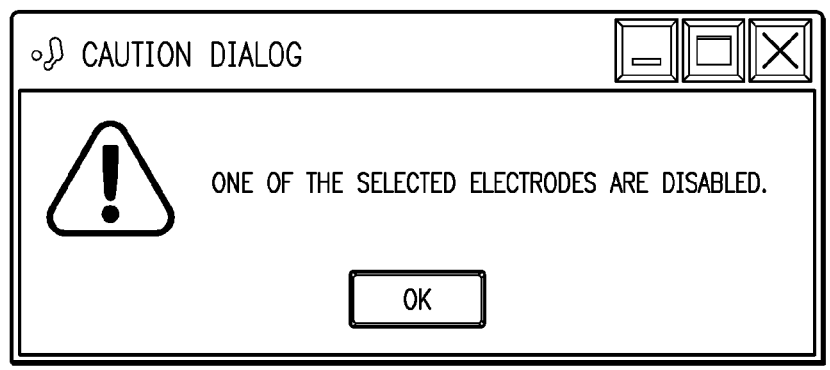
FIG. 26 shows a warning dialog message box.

After the 'Run' button (215) or 'Show Waveform' button (230) are activated, the parameters may be checked against safety requirements of the system. If any of the parameters violates safety limits, a message box will be displayed and the experimenter will need to change the configuration parameters. Common errors may include broken/shorted electrodes, start amplitudes which exceed a maximum charge per phase limit (or the maximum total instantaneous current limit). For example, if there are any broken electrodes, the popup message shown in FIG. 26 may be displayed on the screen. While the experiment is running, the 'Result' screen (214) of FIG. 25 will indicate that stimulation is in progress. The 'Cancel' button (216) of FIG. 25 may be used to cancel Stimulation. A message (not shown) may appear indicating that stimulation was stopped by request.

Figure 28:
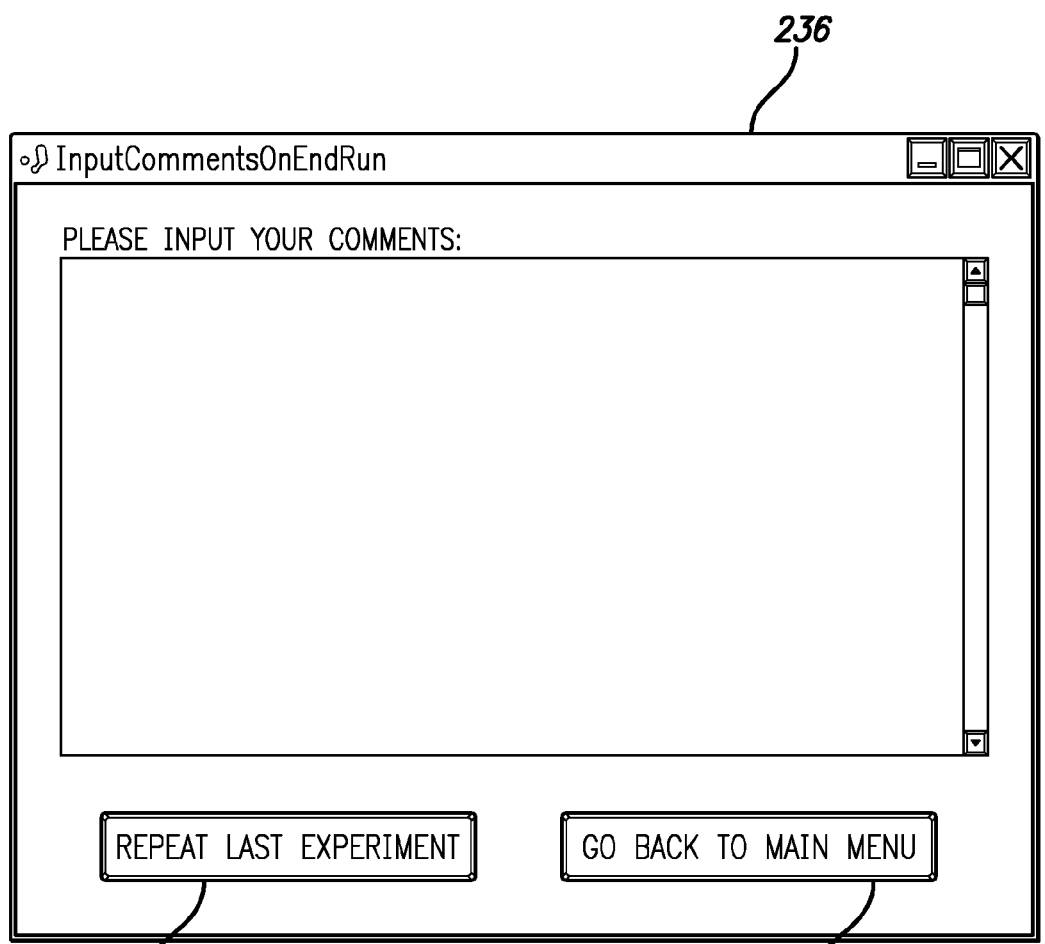
FIG. 28 shows an 'Input Your Comments' message box.

If stimulation has ended normally, a Comment screen (236) shown in FIG. 28 may be displayed. The Comment screen (236) contains two buttons, 'Repeat Last Experiment' (237) and 'Go Back to Main Menu' (238). If Repeat Last Experiment (237) is chosen, the experimenter will be returned to the main Direct Stimulation screen (210) with the Parameters from the last experiment and the experimenter can modify and repeat the experiment. If 'Go Back to Main Menu' (238), is chosen, the experimenter will be returned to the main PTS menu (139) of FIG. 16.

A Clinician-Designed Research Experiments module allows researchers to develop and execute their own custom-designed experiments for research purposes. Experimental psychophysical scripts are developed in MATLAB and are then executed within a MATLAB/PTS framework.

In the next paragraphs, FIGS. 29-53 will describe a video configuration file (VCF) editor. A video configuration file (VCF) defines how the video signal is mapped to the electrical signal for individual or groups of electrodes. In particular, the VCF controls various aspects of the video configuration, e.g., the spatial relationship between the video input and the electrodes. In other words, the VCF provides the instructions for the stimulation that each electrode will deliver based on the video stream captured by the camera located on the glasses (5) of FIG. 3.

The VCF is initially processed on the laptop computer (10) of FIG. 3. After that, the VCF is downloaded to the VPU (20) of FIG. 5 through the video module later shown in FIG. 42, thus allowing the VPU (20) to function in a stand-alone mode. A previously used VCF can also be loaded from the VPU, (20), or other storage such as network storage or flash drive, for adjustment. Once a desired VCF is loaded to the VPU, stimulation of the subject may be performed. The VCFs may be in a comma separate value (.csv) format.

Editing or creation of a VCF is performed by a module called VCF editor. In the next figures, the VCF editor will be shown and described in detail. The "Video Stimulation" function in CFS can be used to download a VCF to the VPU to allow the VPU to be used properly in stand-alone mode or to stimulate the subject in video mode.

Figure 29:
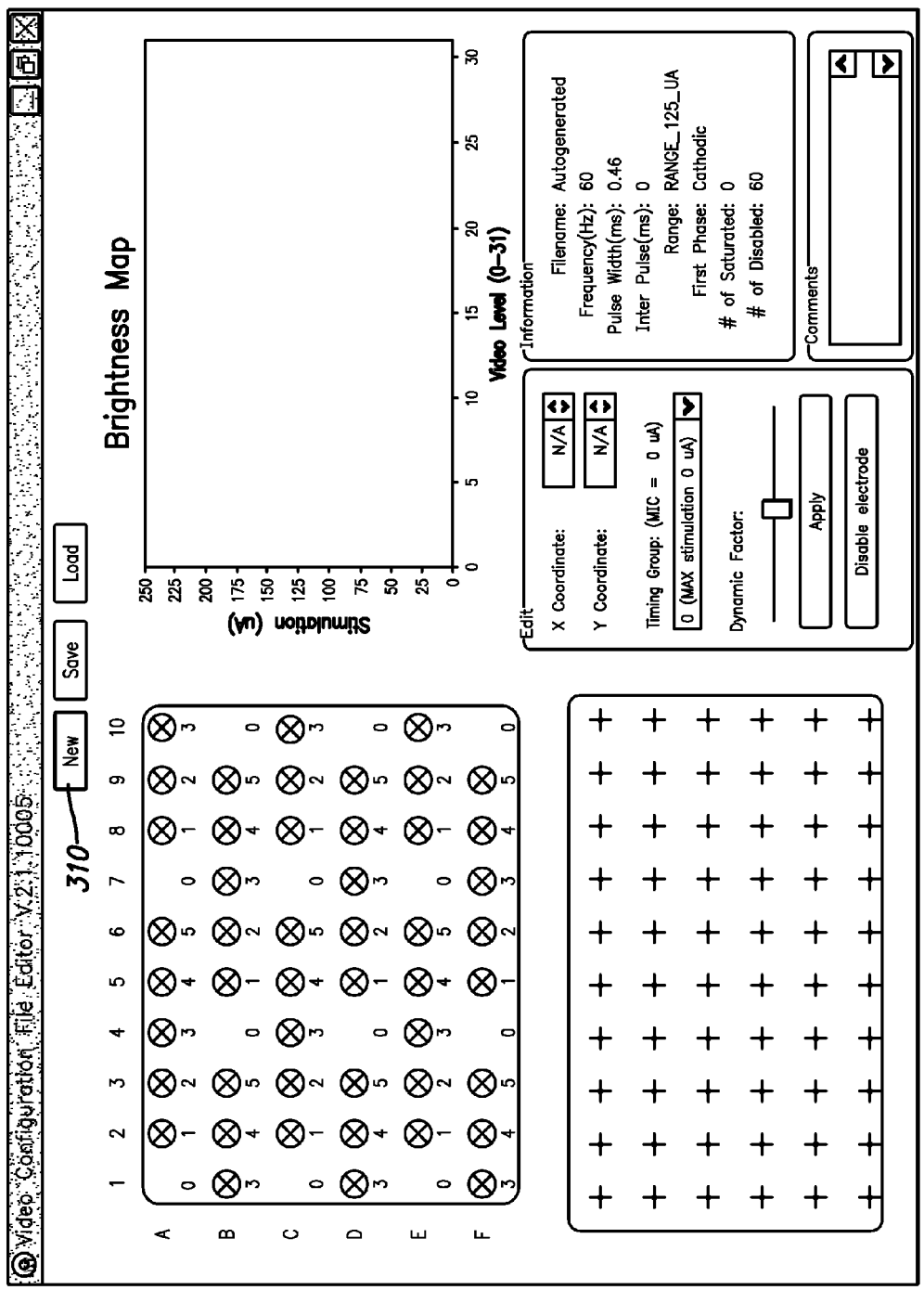
FIG. 29 shows a video configuration file (VCF) editor screen.
Figure 30:
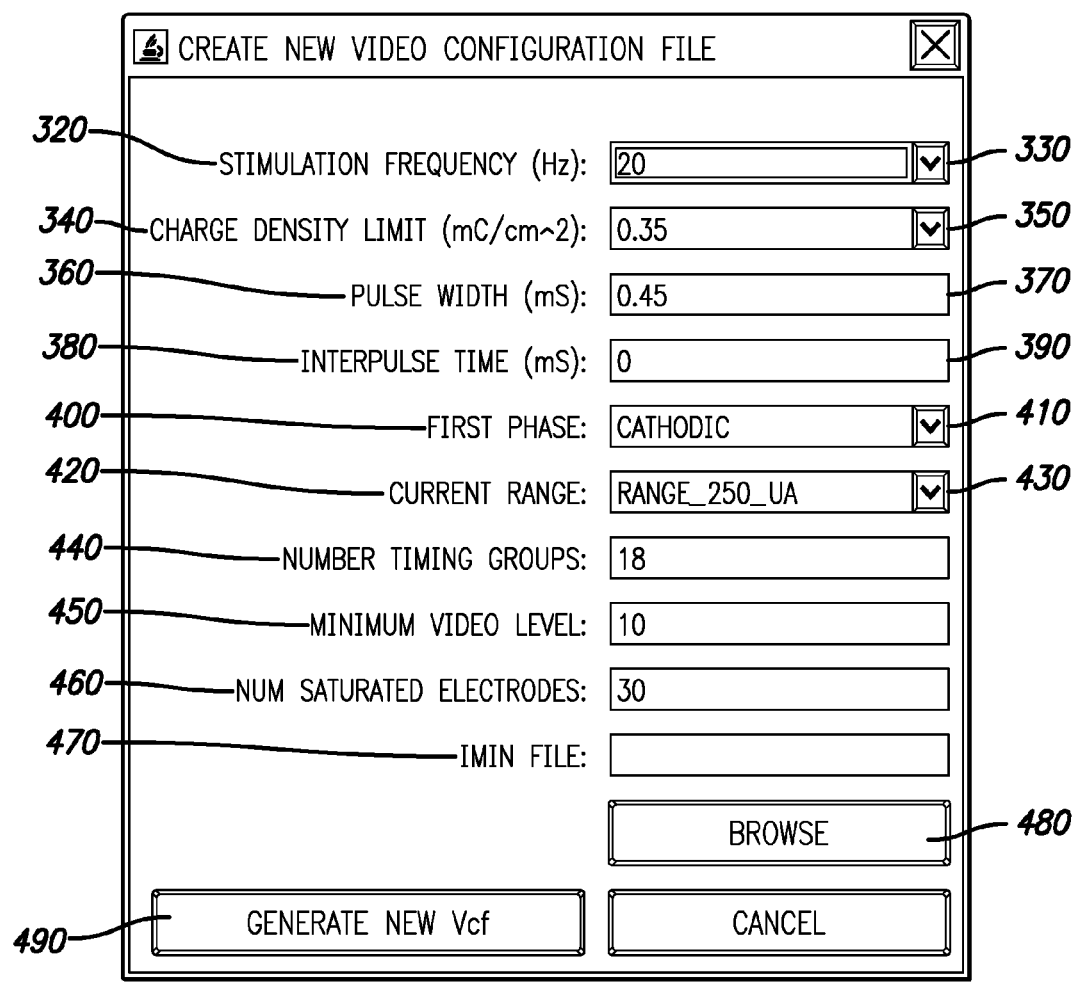
FIG. 30 shows a new VCF global parameter screen with default values.
Figure 32:
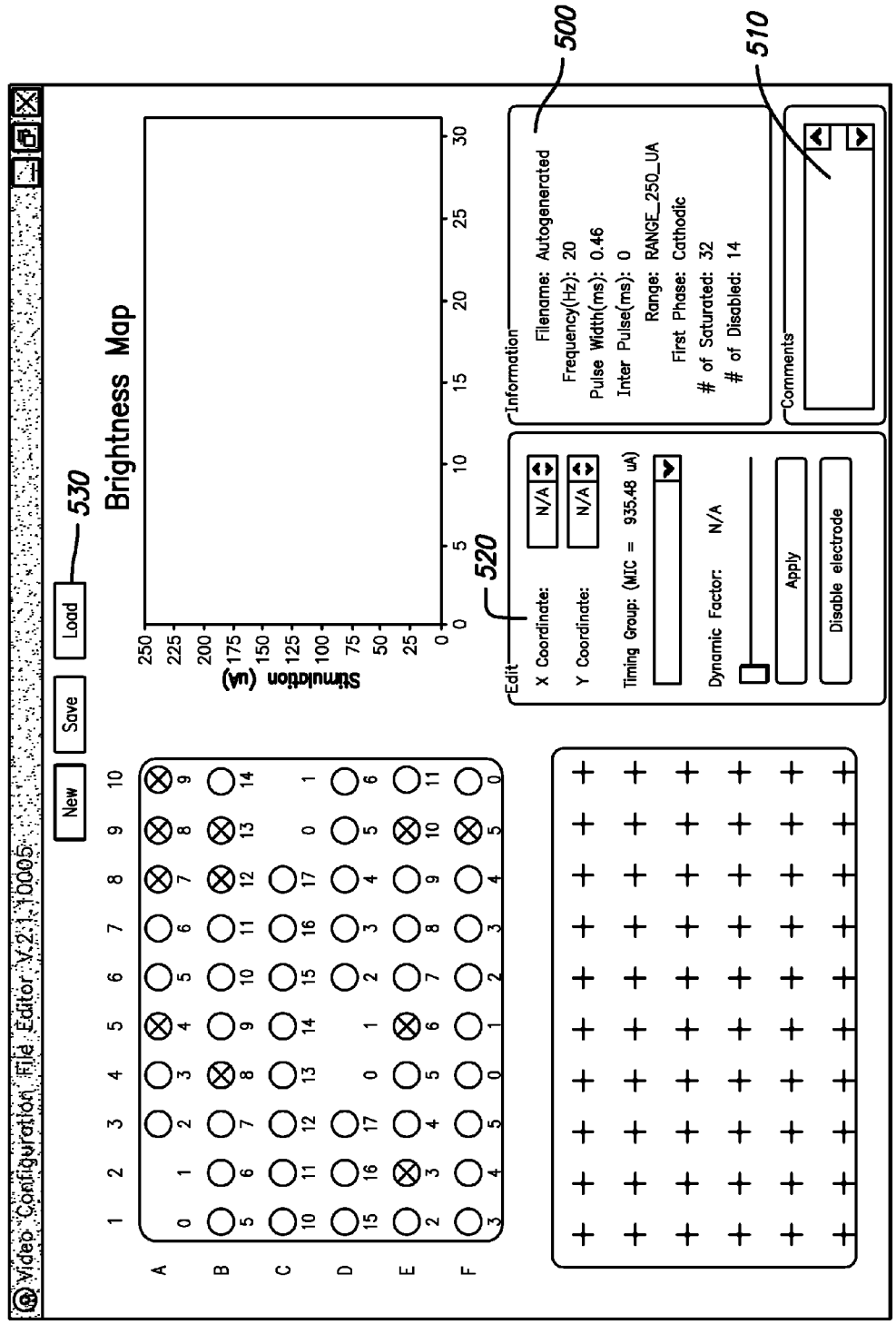
FIG. 32 shows a VCF editor screen with default global parameters and an arbitrary Imin (minimum stimulation current) file.
Figure 33:
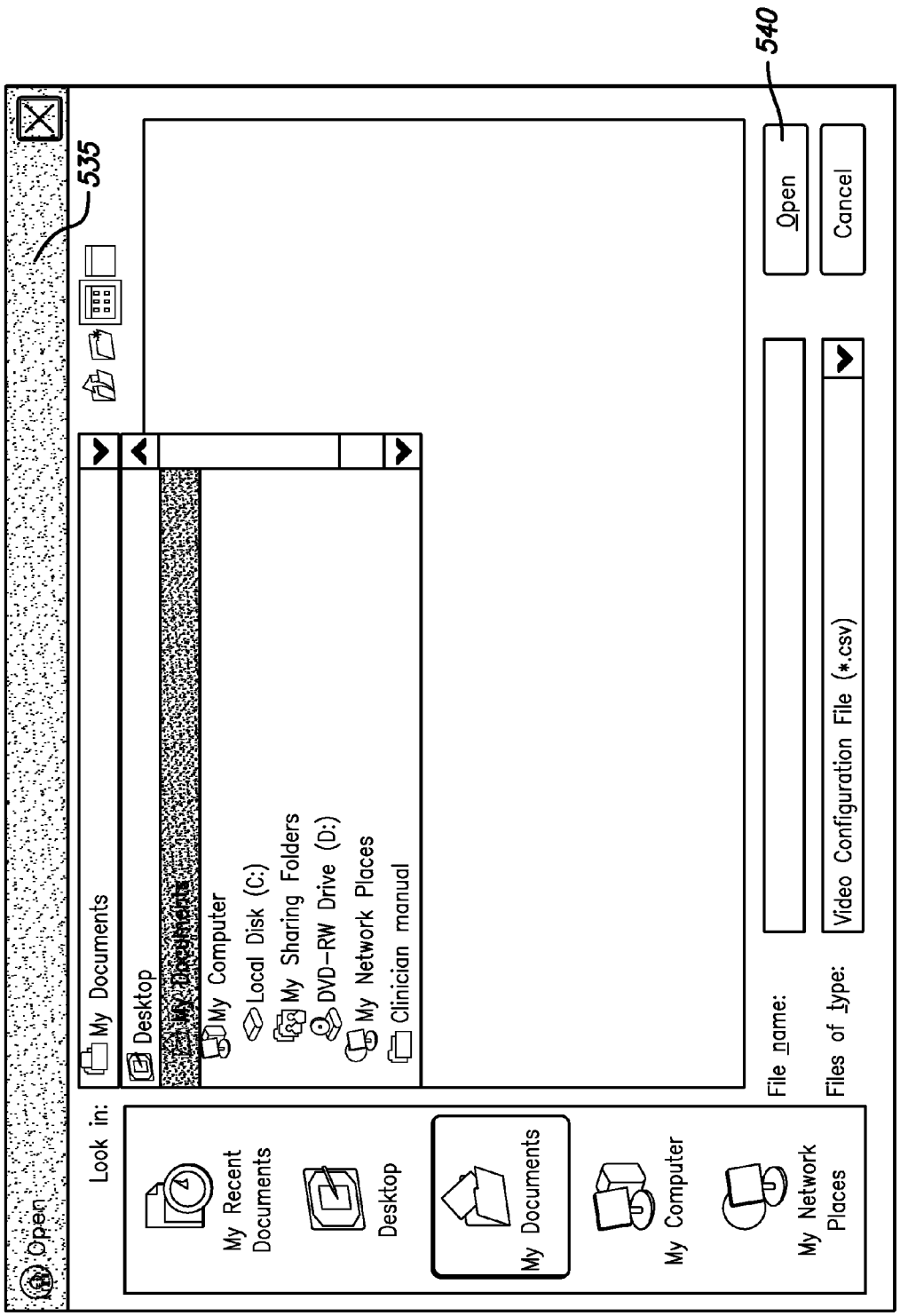
FIG. 33 shows a screen displayed after the "Load" button of the VCF editor screen is clicked.
Figure 34:
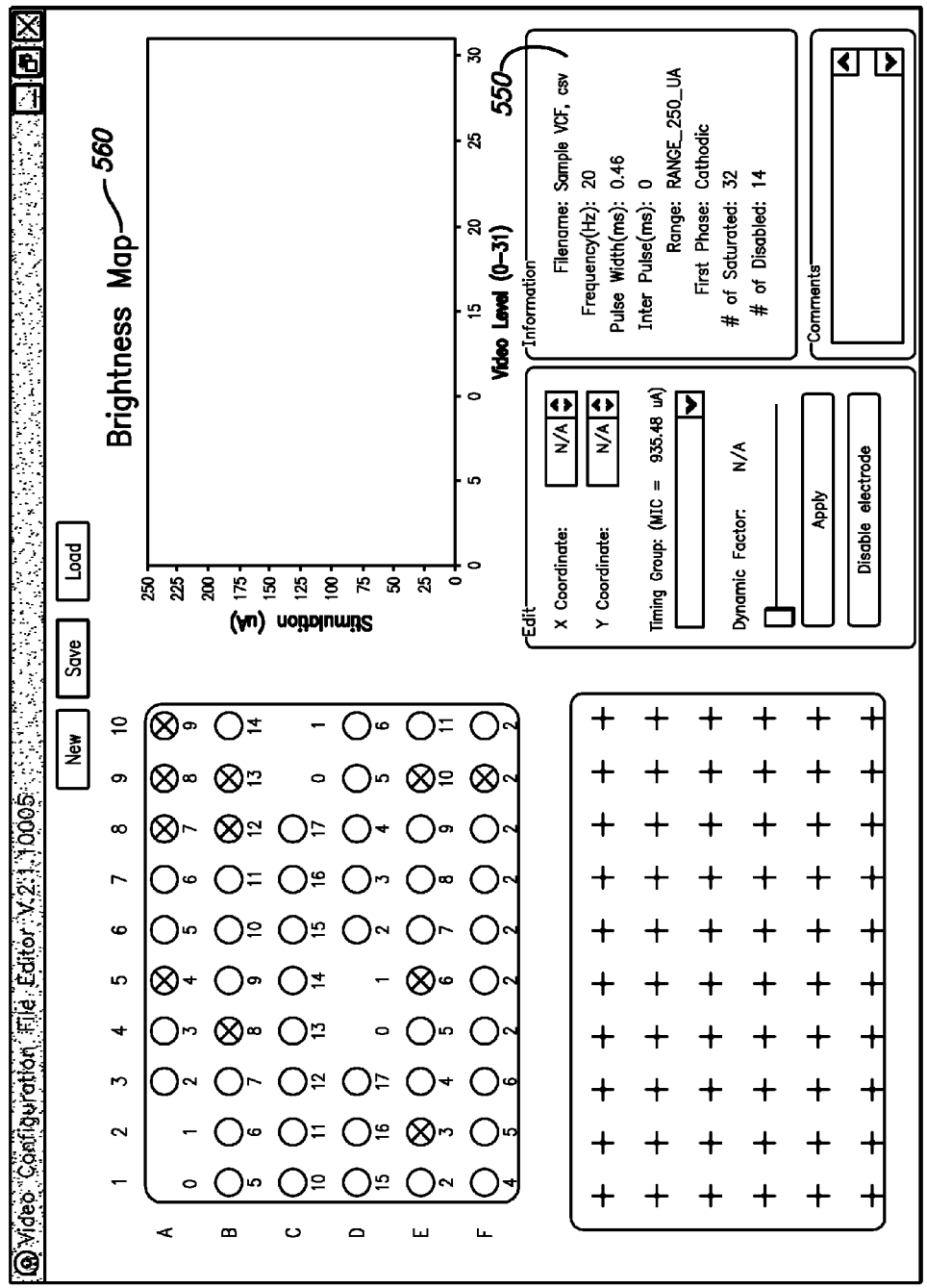
FIG. 34 shows a VCF editor screen with a VCF filename displayed.

A brief summary of what shown in some of FIGS. 29-53 will now follow. FIG. 29 shows the main screen of the VCF editor. FIG. 30 shows the controllable components of the VCF that can be specified upon creation of a VCF. These components include features such as stimulation frequency, charge density limit, pulse width, interpulse time, first phase (cathodic or anodic), current range, number timing groups (i.e. the number of non-simultaneous electrode stimulation groups), minimum video level, number of saturated electrodes, and list of minimum stimulation values for each electrode. An existing VCF can also be loaded to the VCF editor of FIG. 29, as shown in FIGS. 32, 33 and 34.

Figure 35:
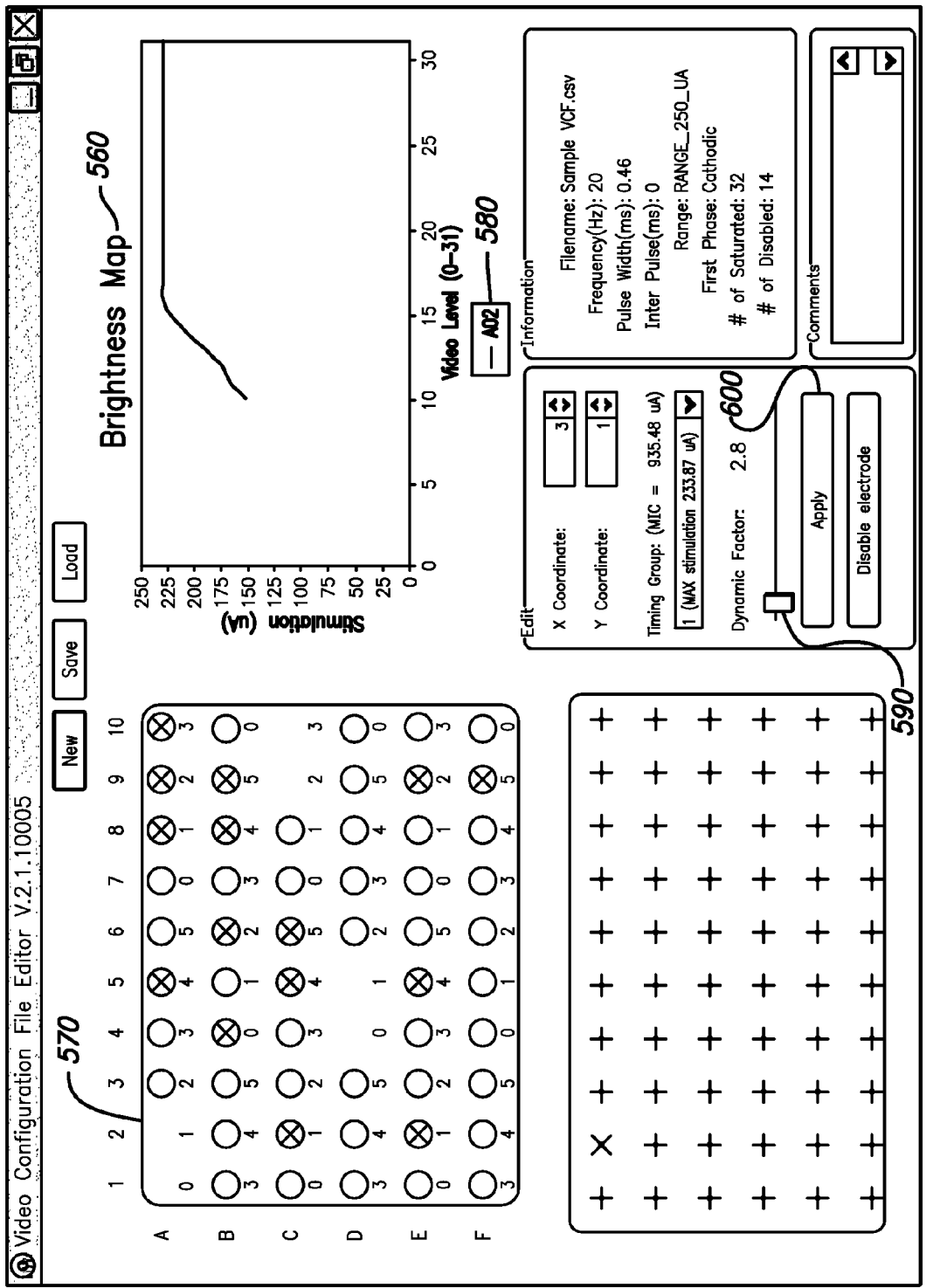
FIG. 35 shows a VCF editor screen with a brightness map corresponding to a selected electrode.
Figure 36:
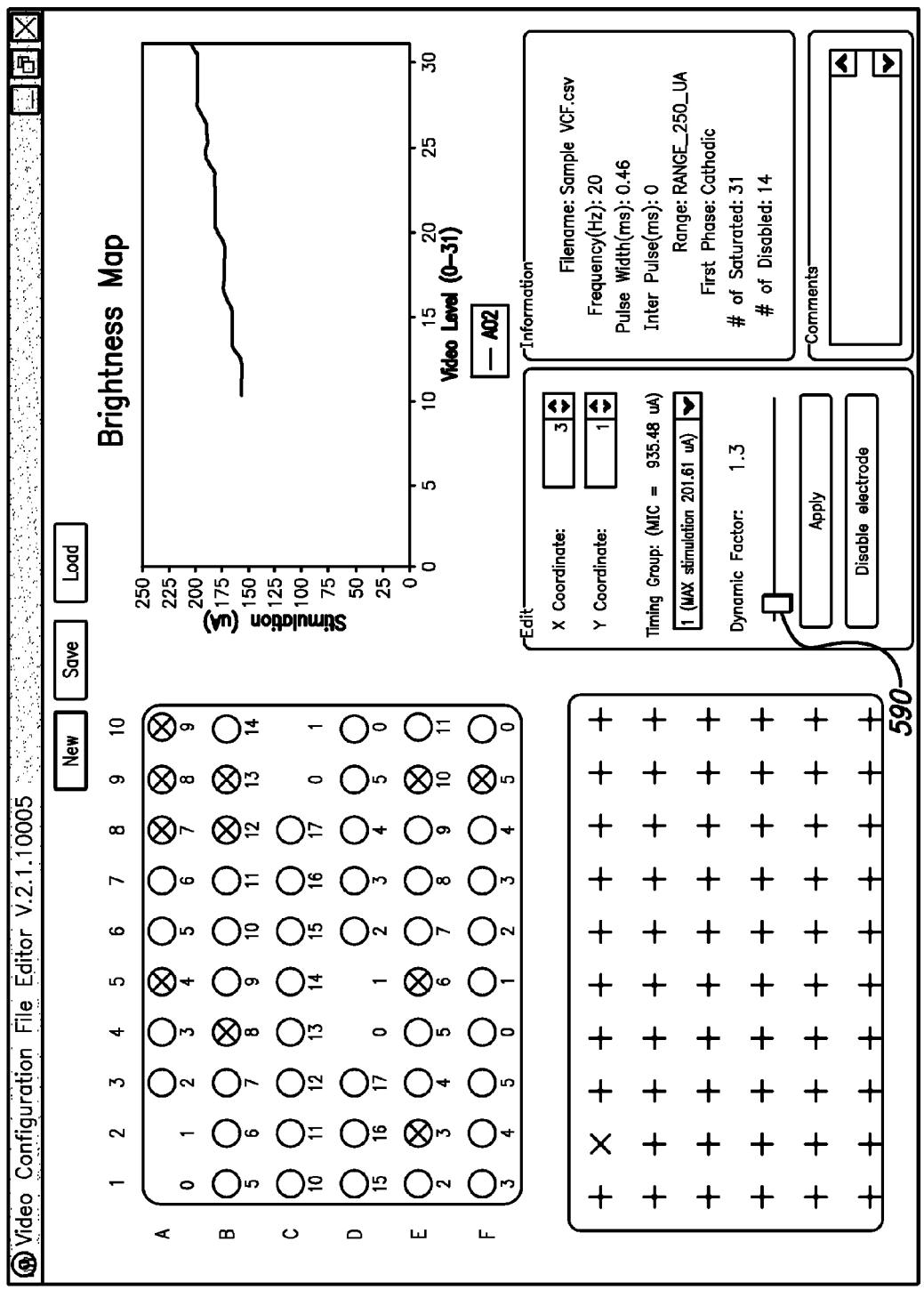
FIG. 36 shows a VCF editor screen with a brightness map corresponding to a newly selected electrode.
Figure 38:
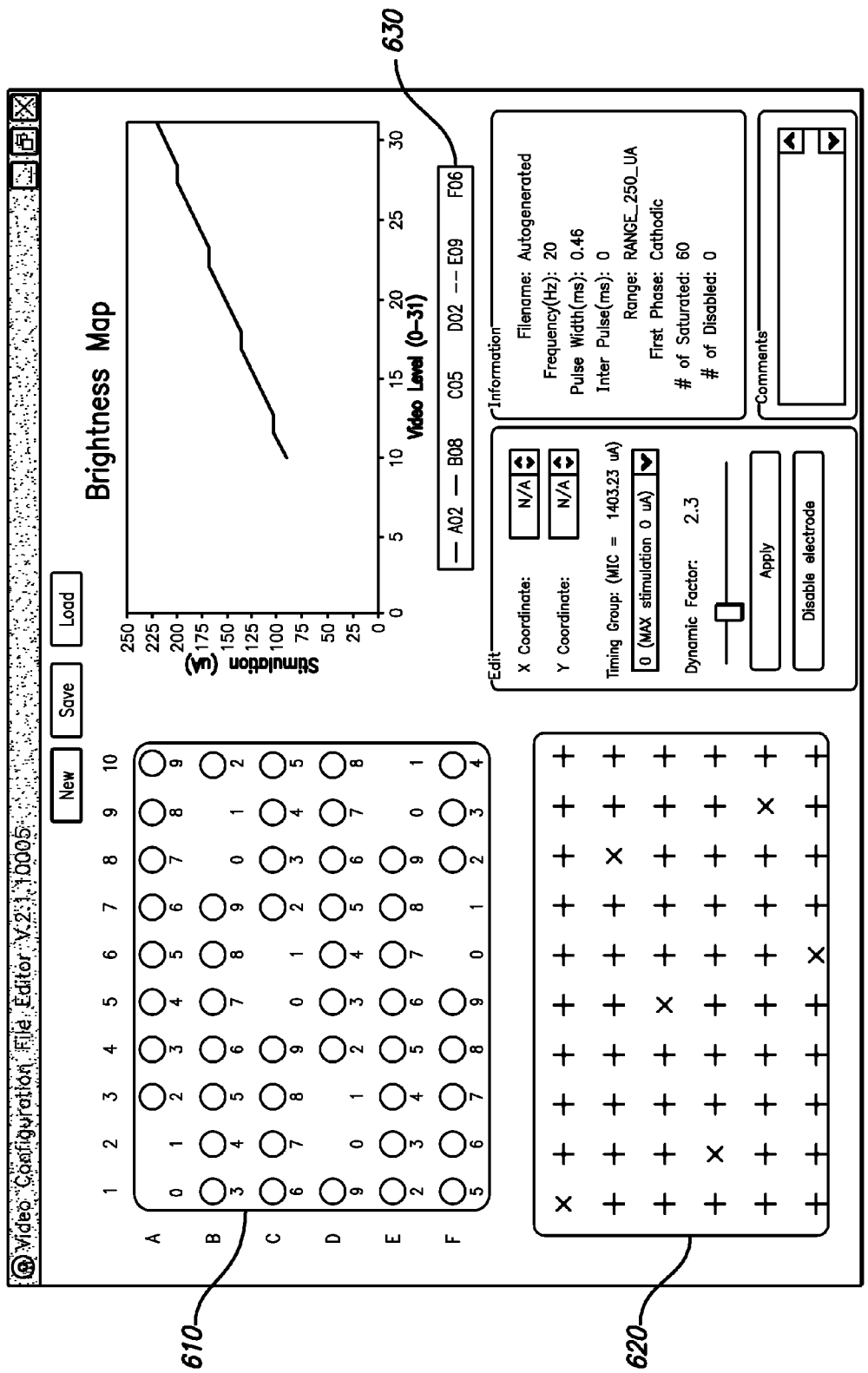
FIG. 38 shows a VCF editor screen with multiple electrodes selected and distance between electrodes maximized.
Figure 39:
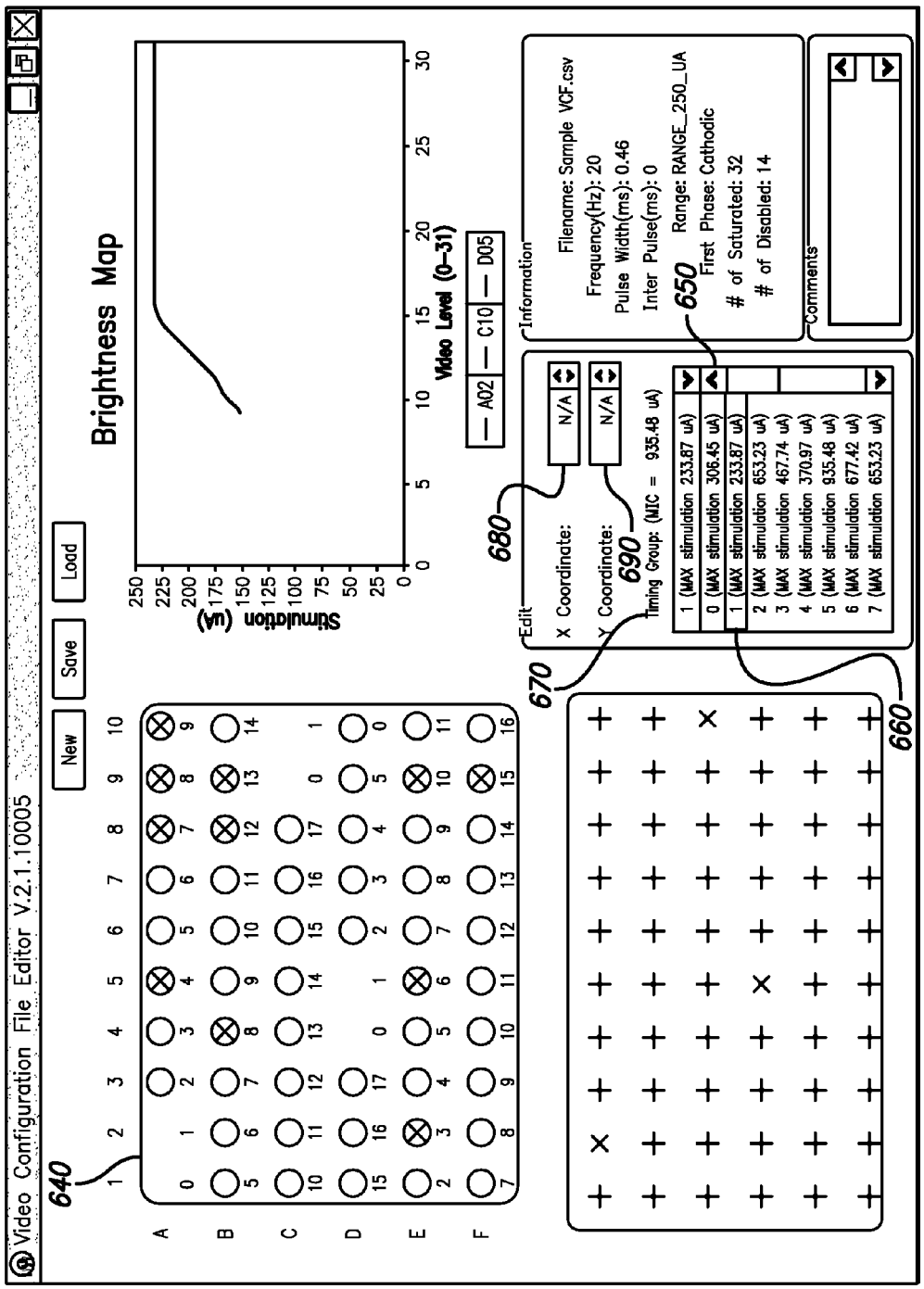
FIG. 39 shows a VCF editor screen where timing group for an individual electrode is changed.
Figure 40:
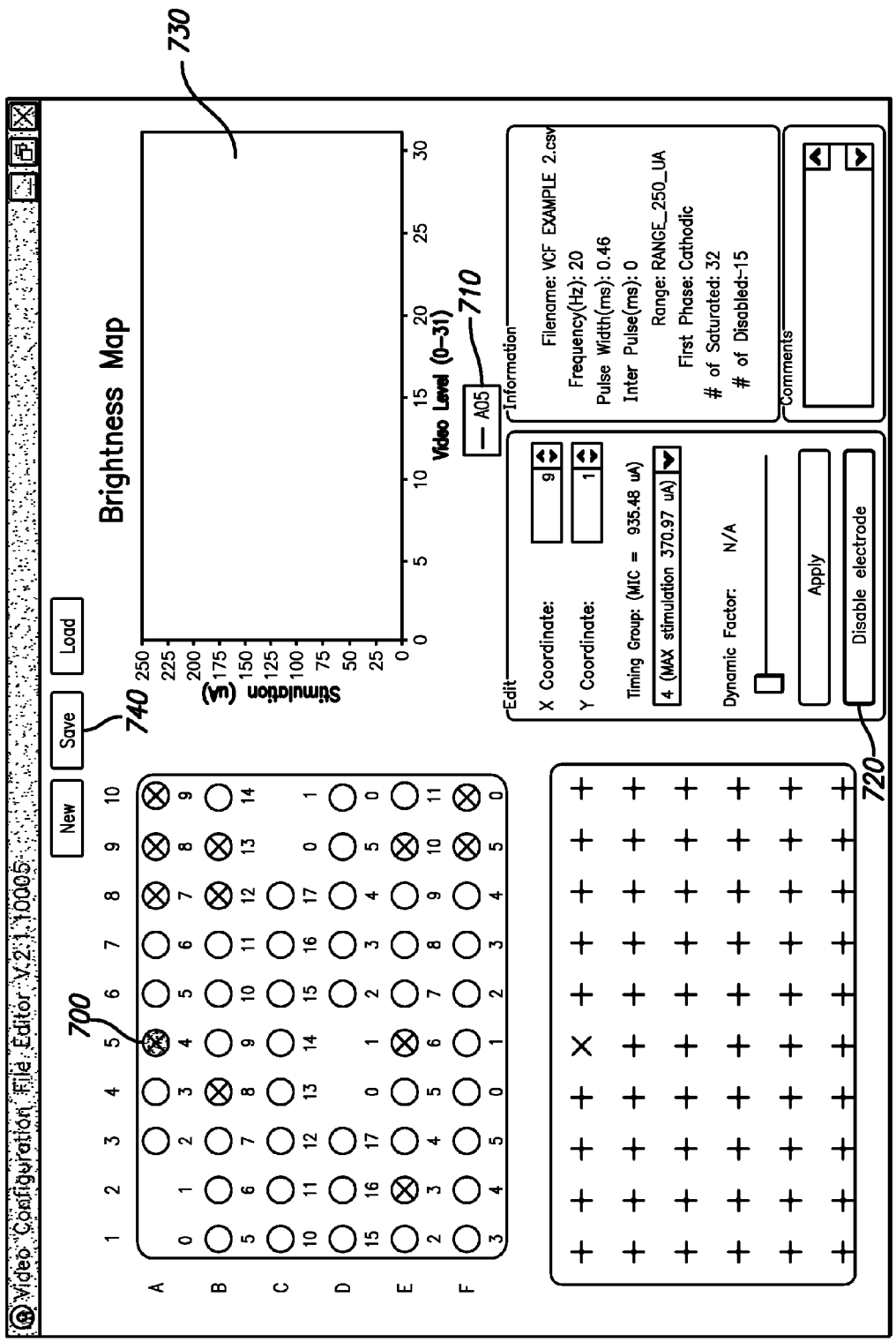
FIG. 40 shows a VCF editor screen where one electrode is disabled.
Figure 41:
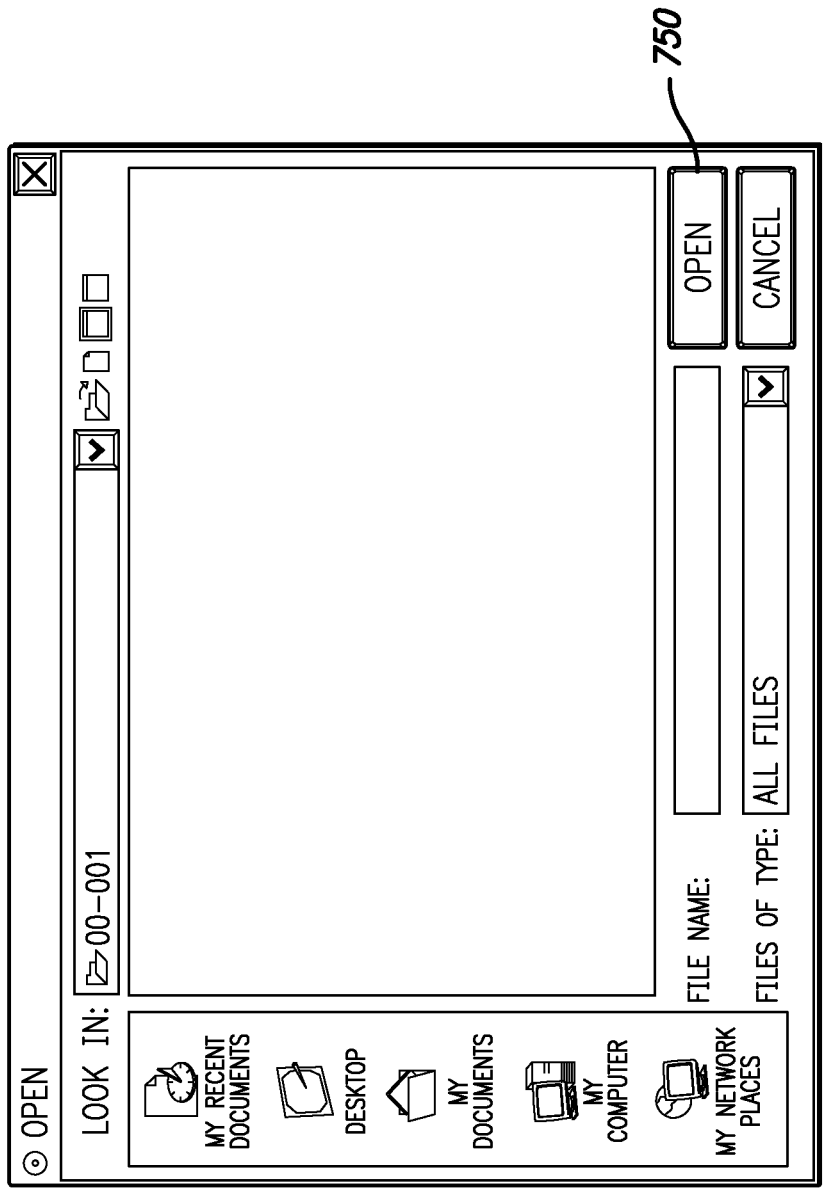
FIG. 41 shows a screen displaying where VCFs can be stored.

One of the editing functions of the VCF editor is that of changing the brightness map for an individual electrode or electrode groups, as shown in FIGS. 35, 36 (single electrode), and 37 (electrode group). The brightness map represents the mapping between the video brightness level and the corresponding stimulation current amplitude specified in the VCF. A further editing function is that of defining or changing the temporal stimulation pattern to which each electrode or electrode groups are assigned. This feature is described in FIG. 38 (where six electrodes are assigned to the same timing group) and 39 (where a timing group for a single electrode is changed). FIG. 39 also shows how the spatial mapping between the output of the camera and the array of electrodes can be modified. The spatial mapping represents the spatial location (coordinates) from the subject's viewpoint for each electrode as specified in the VCF. One or more electrodes can also be disabled, as shown in FIG. 40. Once created or modified, a VCF is stored in a particular folder, as shown in FIG. 41.

Figure 42:
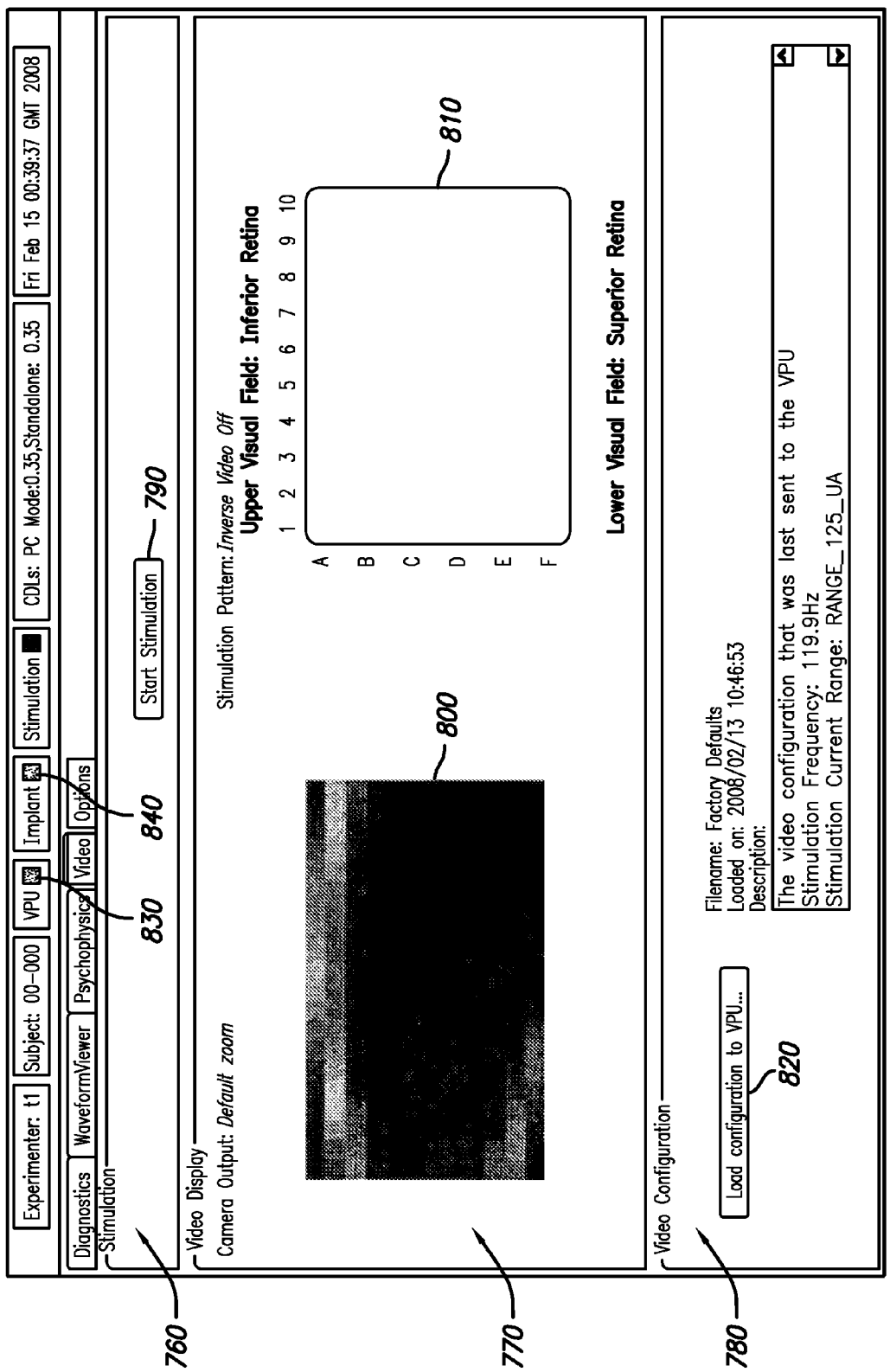
FIG. 42 shows a video screen with a stimulation section, a video display section, and a video configuration section.
Figure 43:
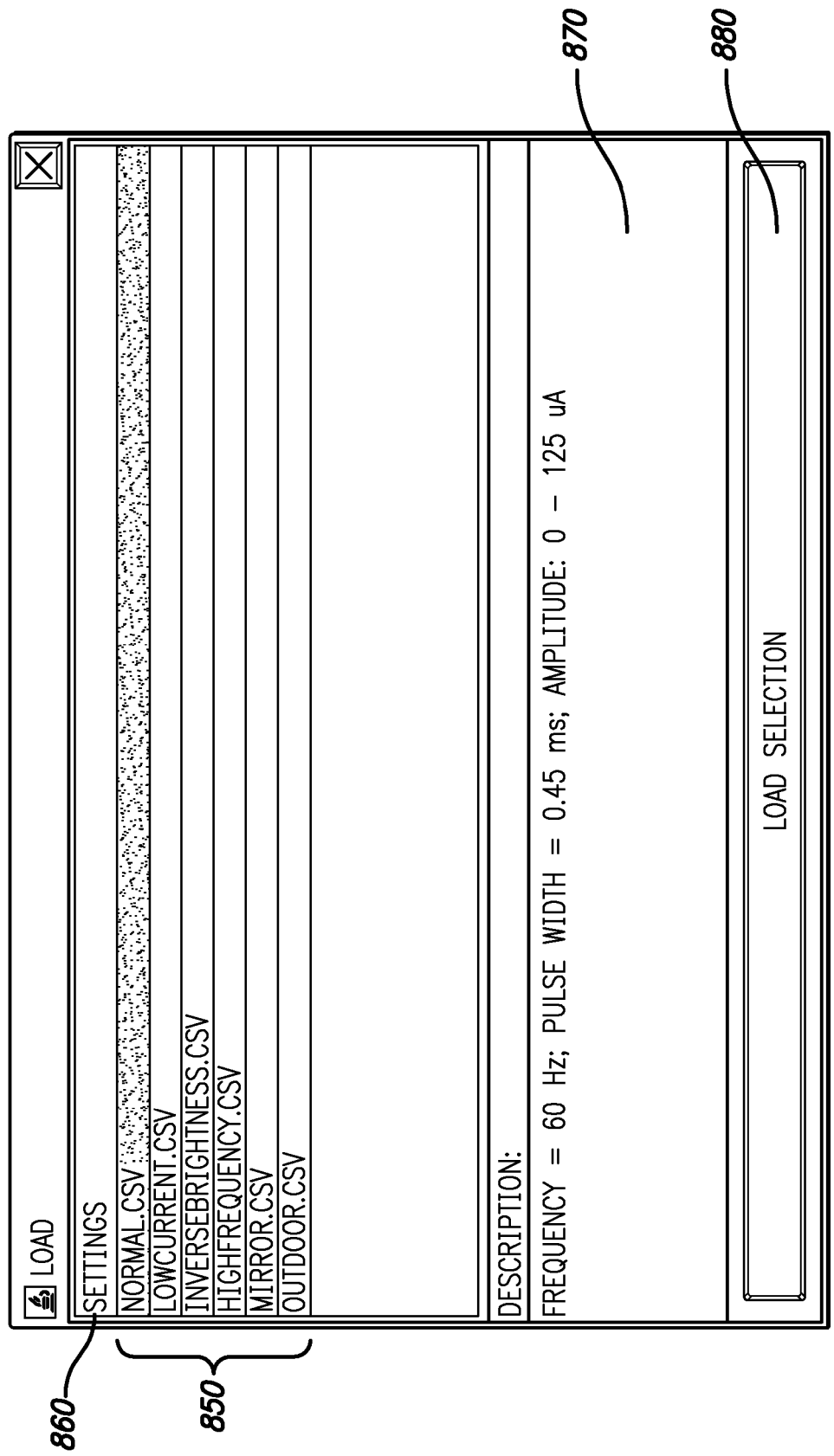
FIG. 43 shows a "Load" screen appearing upon clicking on the "Load configuration" button of the video screen of FIG. 12.

The video module briefly introduced in paragraph [0091] above is shown in FIG. 42. The video module allows a VCF to be loaded onto the VPU. The loading process is explained in detailed in the paragraphs that make reference to FIGS. 42, 43 and 44.

Figure 47:
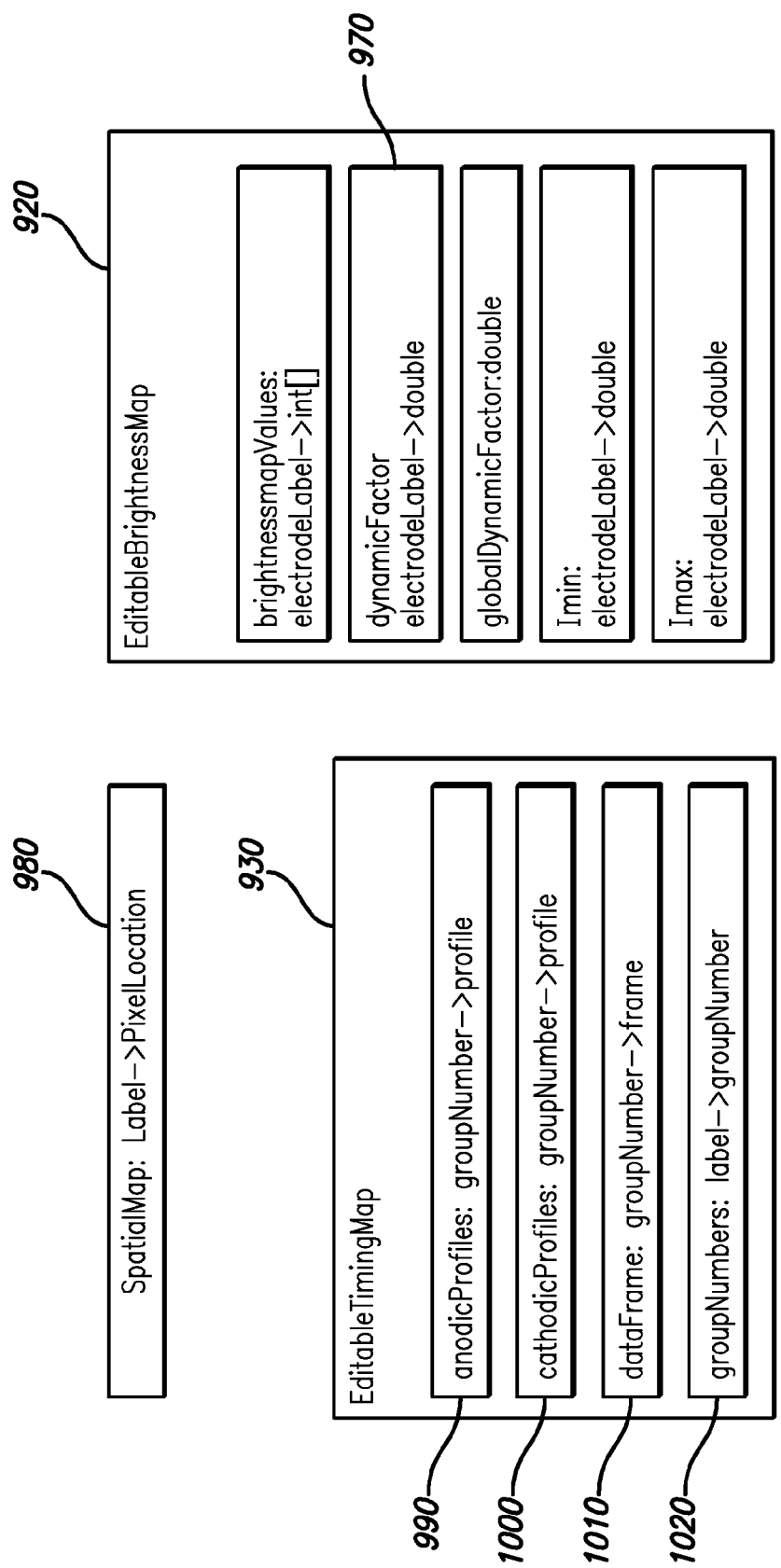
FIG. 47 shows a possible software architecture for software objects such as spatial map, timing map and brightness map.
Figure 48:
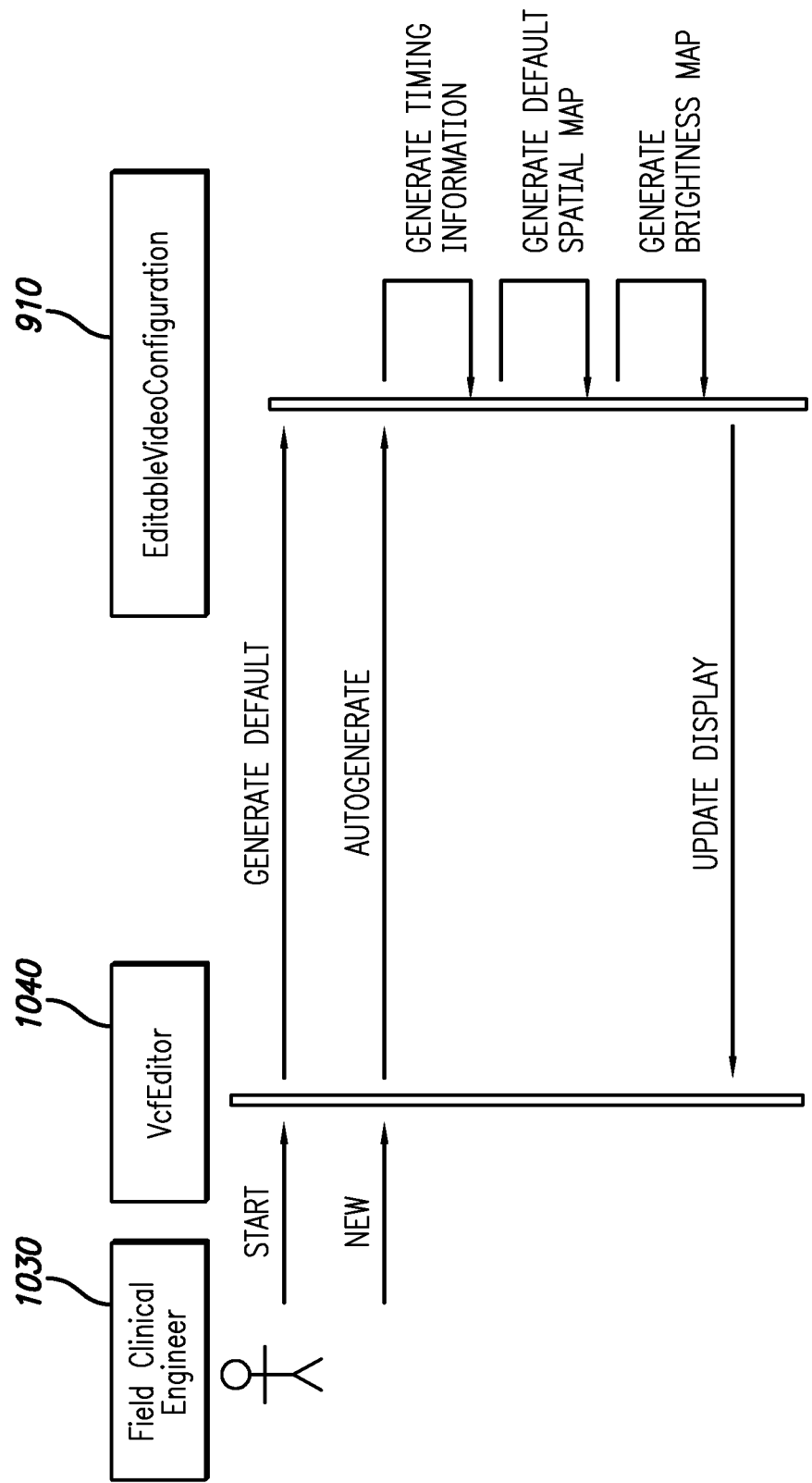
FIG. 48 is a diagram showing auto-generation of a video configuration.
Figure 49:
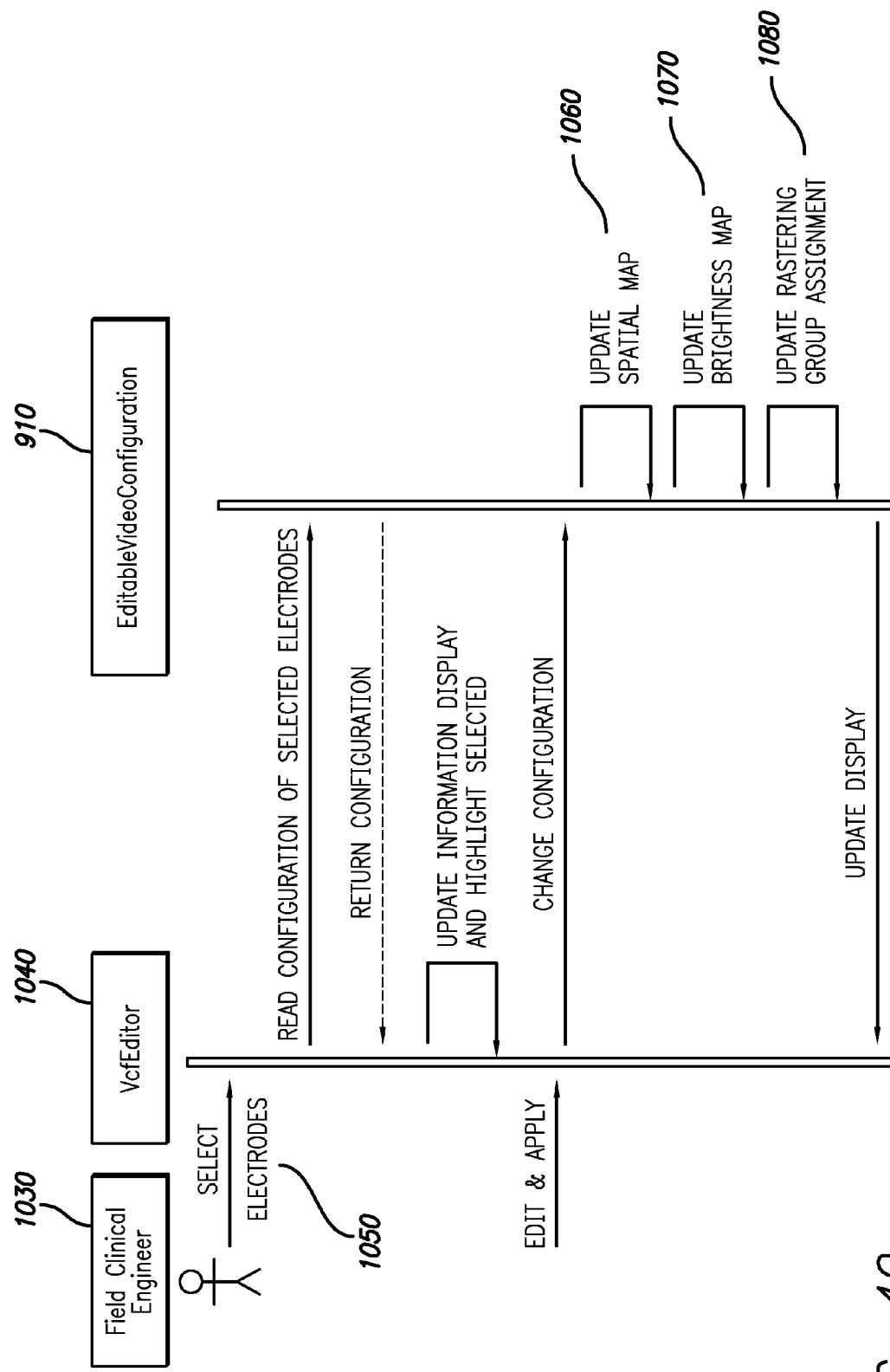
FIG. 49 is a diagram showing editing of the video configuration.
Figure 50:
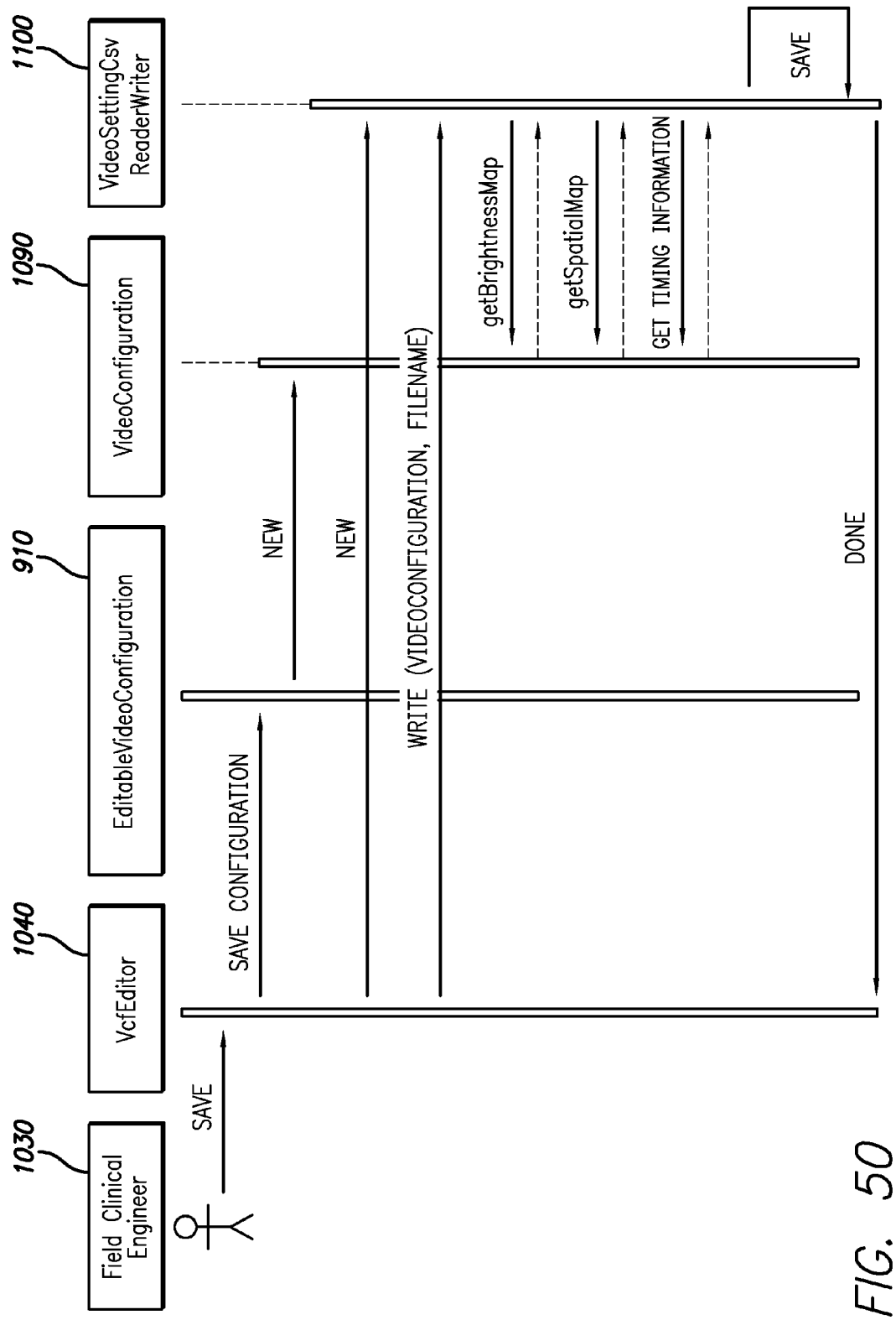
FIG. 50 is a diagram showing an operation of saving the video configuration to file.
Figure 51:
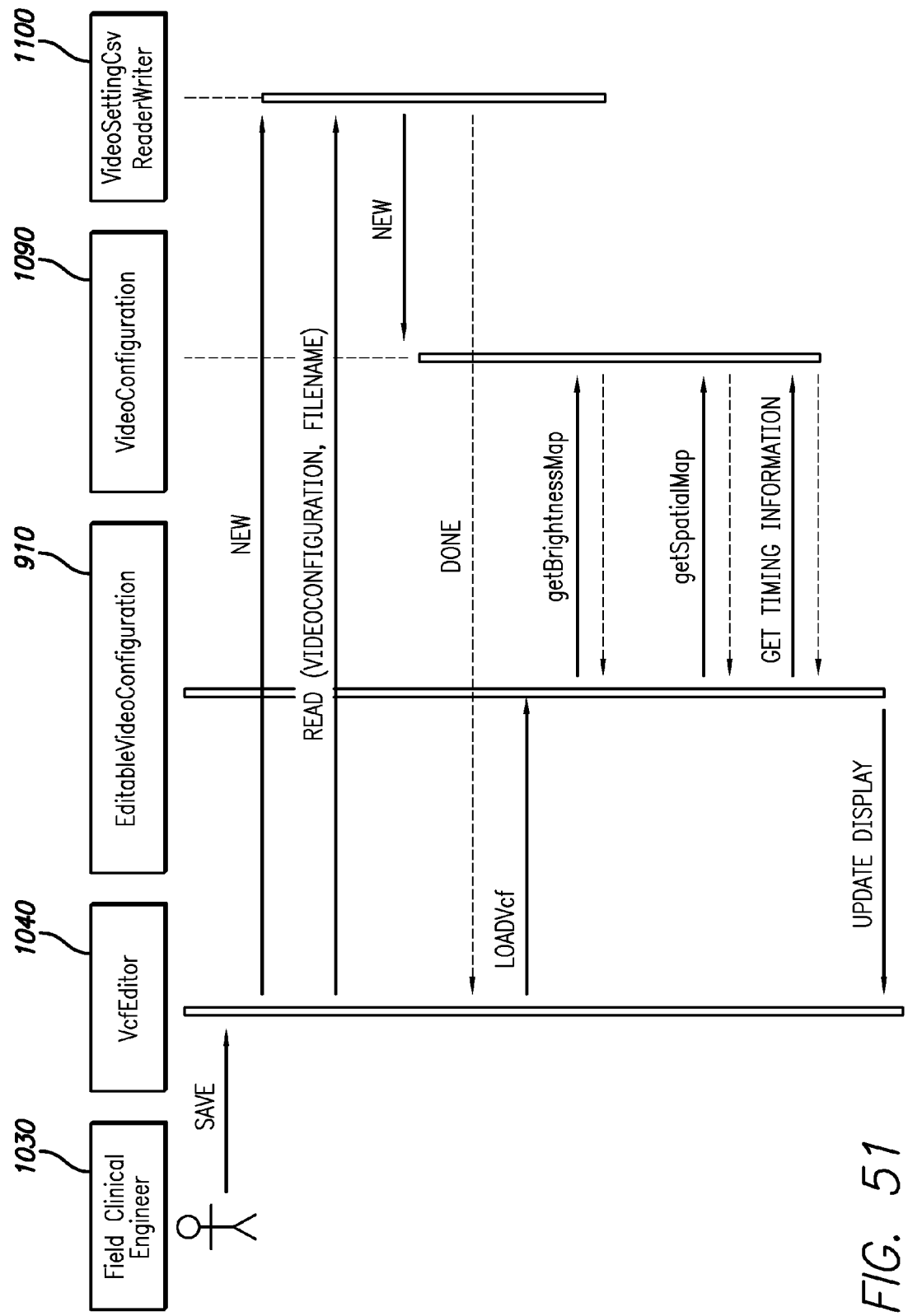
FIG. 51 is a diagram showing an operation of loading a video configuration from an existing file.
Figure 52:
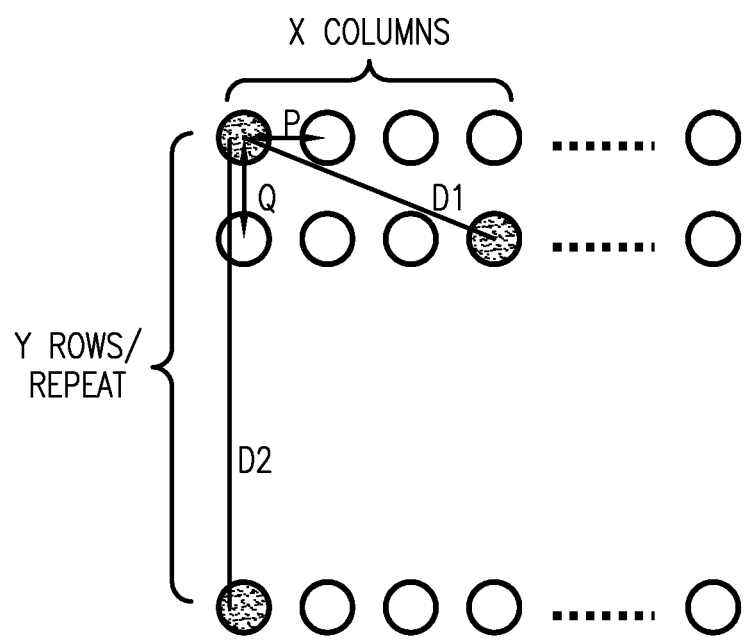
FIG. 52 is a diagram of the process used to maximize distance among electrodes of the same timing group.
Figure 53:
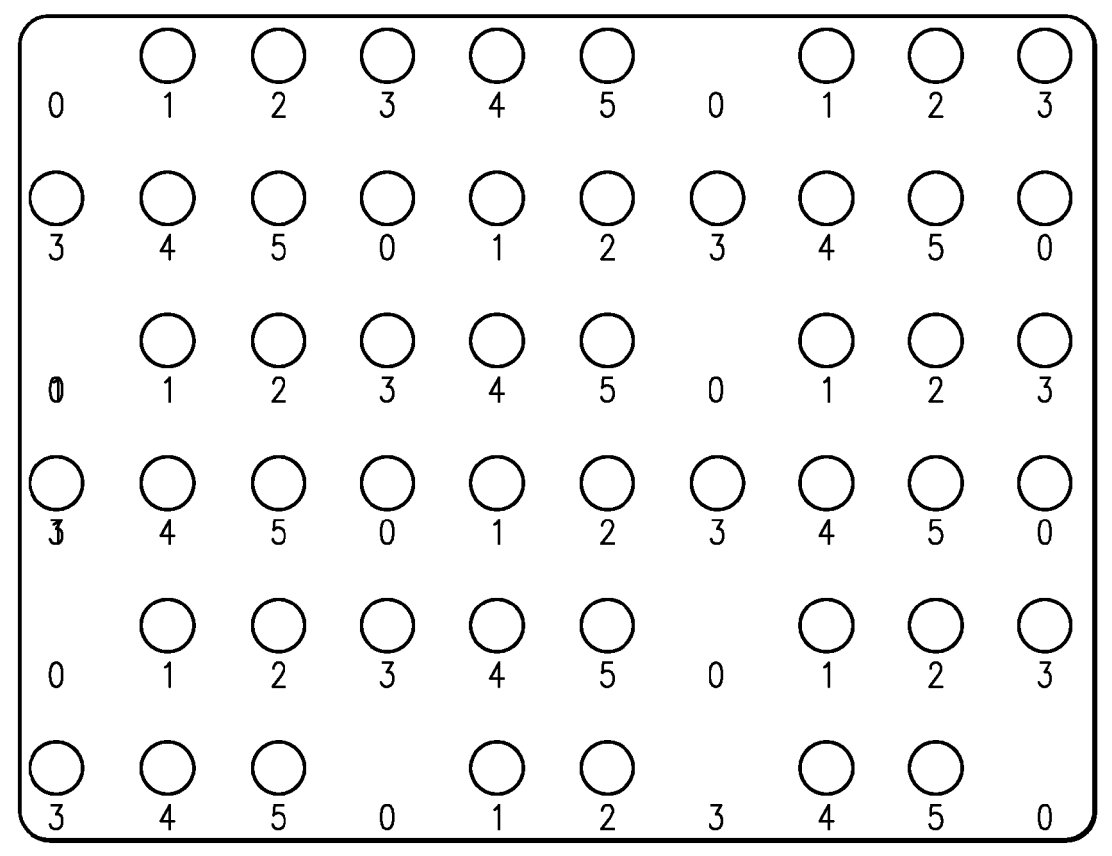

FIGS. 45-53 will deal with the software architecture of the VCF editor. FIGS. 47, 48 and 49 show high level diagrams of software classes associated with the VCF editor graphic user interface (GUI) application. FIGS. 48-51 represent sequence diagrams of auto-generation of video configuration, edit video configuration, save video configuration to file, and load video configuration from a file. FIG. 52 shows a diagram useful to understanding how distance between electrodes in the same timing group is maximized by way of an algorithm, the result of which is shown in FIG. 53.

FIGS. 29-44, briefly summarized above, will now be discussed in detail.

FIG. 29 shows a video configuration file (VCF) editor screen. A new VCF is opened by clicking on the "new" button (310). A parameter screen will be displayed with default global values as shown in FIG. 30.

Figure 31:
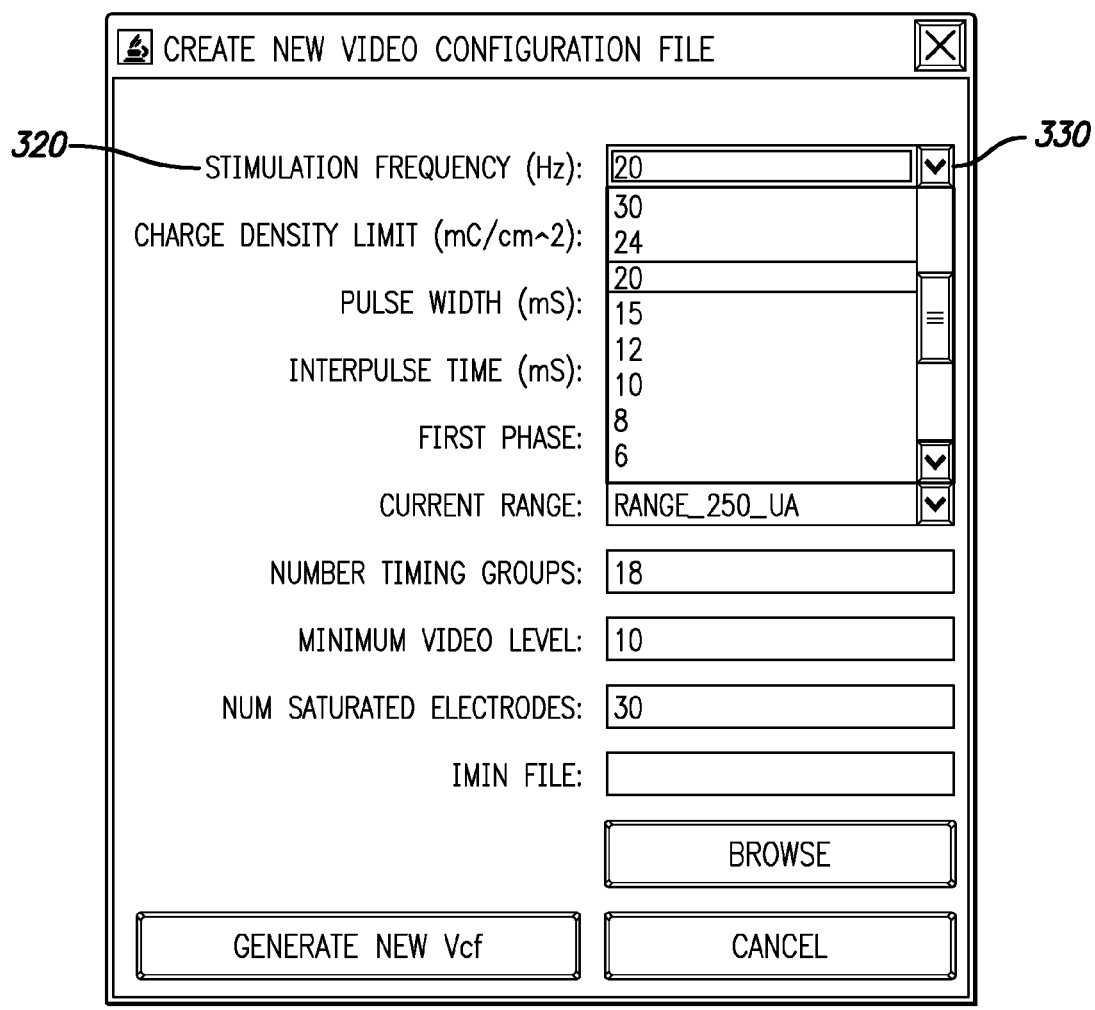
FIG. 31 shows the screen of FIG. 2 with a stimulation frequency pull down menu open.

As shown in FIGS. 30 and 31, the "Stimulation Frequency" (320) is the number of pulses sent to each electrode per second. Stimulation frequency can be changed by clicking the stimulation frequency pull-down menu (330). Some of the frequencies that can be supported by the VCF are: 120 Hz, 60 Hz, 40 Hz, 30 Hz, 24 Hz, 20 Hz, 15 Hz, 12 Hz, 10 Hz, 8 Hz, 6 Hz, 5 Hz, 4 Hz, 3 Hz, 2 Hz, and 1 Hz. The default stimulation frequency is 20 Hz.

Turning to FIG. 30, the "Charge Density Limit ($mC/cm^2$)" (340) is the upper limit for the charge density that is delivered to the subject. By way of example, four ranges can be chosen from in the pull-down menu (350): 0.35, 0.5, 0.75 and 1.0 $mC/cm^2$. The default is 0.35 $mC/cm^2$.

The "Pulse Width" (360) is defined as the width of the biphasic pulse per phase. "Pulse Width" (360) can be changed by typing into field (370) the pulse width in ms. The default pulse width is 0.45 ms. The range of the pulse width can be 0-3 ms.

The "Interpulse Time" (380) is defined as the gap between the cathodic and anodic phases of the biphasic pulse. "Interpulse Time" (380) can be changed by typing into field (390) the interpulse time in ms. The default value is 0. The maximum interpulse time can be set to 6 ms−2*(pulse width). The "First Phase" (400) defines whether the first phase of the biphasic pulse is "Cathodic" or "Anodic". "First Phase" can be changed by clicking on the "First Phase" pull-down menu (410).

The current range (420) is defined as the maximum stimulation current that can potentially be delivered to each electrode. However, the actual current range that can be delivered to each electrode is limited by the maximum charge density defined for the device and is thus related to the pulse width. For example, if the pulse width is set at 0.45 ms, the maximum current range without exceeding the charge density limit of 0.35 $mC/cm^2$ is 0-250 µA. If a pulse width of 0.11 ms is chosen, then the current range of 1000 µA is appropriate. Any amplitude value greater than the maximum safe limit (as defined by the maximum charge density) will be set to the maximum safe amplitude. "Current Range" (420) can be changed by clicking on the pull-down menu (430). According to an embodiment of this disclosure, the VCF can support, for example, current ranges of 0 to 125 µA, 250 µA, 500 µA, and 1000 µA.

The "Number of Timing Groups" (440) is defined as the number of interleaved (non-simultaneous) electrode stimulation groups in the VCF. It can vary, for example, from 1 to 60 groups.

The "Minimum Video Level" (450) defines the limit for the digital video level. When the video level is below that value there will be no stimulation applied to the electrodes. The range of the "Minimum Video Level" can be 0-31.

The "Num saturated electrodes" parameter (460) defines the number of electrodes that will reach the maximum allowable current level limited by the "charge density limit" for that VCF. The number of saturated electrodes will increase if the slope of the brightness mapping curve is increased. By default, the slope of the brightness curve is varied (e.g., uniformly) for all the electrodes to meet this criterion.

The "Imin File" (470) is a list of minimum stimulation values for each electrode that are derived from threshold testing. The threshold values define the level of stimulation current that is applied for each electrode at the minimum video level discussed with reference to the "Minimum Video Level" (450) above. This file should be generated prior to creating a new VCF and can then be loaded into the VCF editor by using the Browse button (480) and selecting the appropriate Imin file. In this file, also the disabled electrodes can be indicated.

Based on the above, once the "Generate New VCF" button (490) is clicked, a new VCF based on the chosen settings is generated.

FIG. 32 displays the new VCF created with the default global parameters and an arbitrary Imin file. See the "Information" section (500) of FIG. 32, which shows the values for the global parameters. The VCF created using the default global values has 18 timing groups (0-17). The 'Comments' field (510) allows the user to record comments for that particular VCF which will be displayed each time the VCF is opened with the editor. The 'Edit' section (520) allows the user to modify the VCF and is discussed in detail below. To load an existing VCF to the Editor, the "Load" button (530) in the main editor screen can be clicked.

A new screen (535) will be displayed after the "Load" button (530) is clicked, as shown in FIG. 33. An existing VCF can be selected by selecting the appropriate directory and file name and click on the 'Open' button (540) of FIG. 33. The VCF will be loaded to the editor and the file name is displayed in the editor screen, as shown by circle (550) in FIG. 34.

As also shown in FIG. 35, the brightness map (560) can be changed for an individual electrode or electrode groups. The brightness map is defined as the mapping between the video brightness level and the corresponding stimulation current amplitude. The brightness map (560) for each individual electrode is displayed when the electrode is selected. To select an individual electrode, the user should click on the center of the electrode circle (570). FIG. 35 shows the brightness map for electrode A2, see also (580). In this figure, the brightness range of 0 to 31 units is mapped to the stimulation current range of 0 to 233 µAmps.

The brightness map formula can be defined as:

$$\text{Stimulation Amplitude} = \begin{cases} I_{min}\left(1 + \dfrac{(k-1)*(\text{Brightness}-V_{min})}{V_{max}-V_{min}}\right) & \text{if} < I_{max} \\ I_{max} & \text{if} > I_{max} \end{cases}$$

Where: $V^{min}$ is the minimal video level (0-31). The default value for $V^{min}$ is 10; $V^{max}$ is the maximum video level set at 31; $I^{min}$ is the stimulation current corresponding to $V^{min}$ for each electrode; and K is the dynamic range factor; the ratio between the maximum and minimum current for each electrode ($I^{max}/I^{min}$). $I^{max}$ is defined by the charge density limit (CDL) and the current range. As shown above, the stimulation current amplitude will never exceed Imax to ensure safety.

To change the brightness map for an individual electrode, the electrode should be selected. Once the electrode is selected, the slide bar (590) should be moved to adjust the dynamic range factor. The "Apply" button (600) should then be clicked. The new brightness map will then be displayed as shown in FIG. 36.

Figure 37:
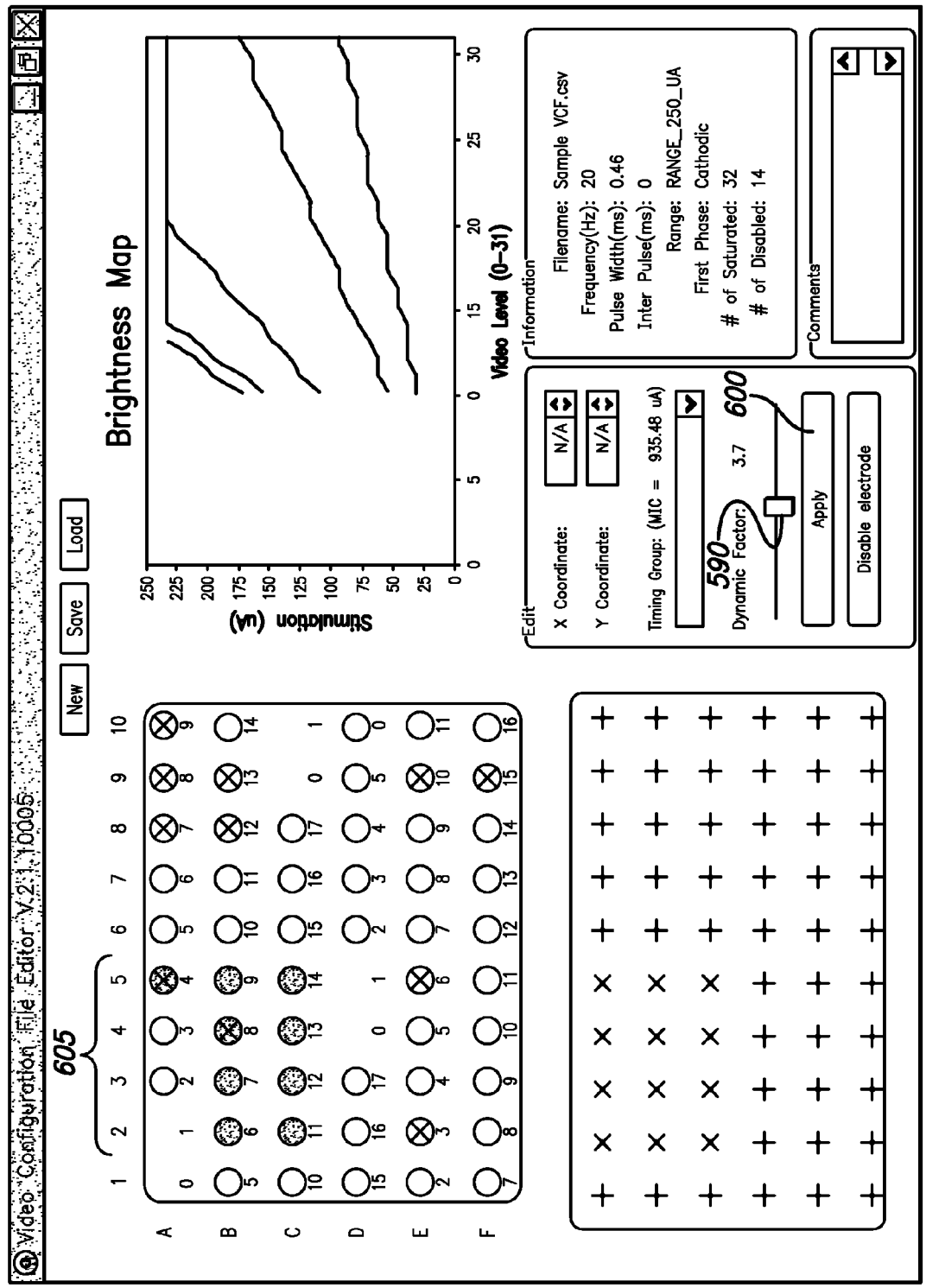
FIG. 37 shows a VCF editor screen with a brightness map for multiple electrodes.

To set the same brightness map for a group of electrodes, a group of electrodes should be selected by left-clicking the mouse and dragging the mouse to highlight the group as shown by reference numeral (605) in FIG. 37. Alternatively, the electrodes can be selected one at a time while pressing down the 'Ctrl' key on the keyboard. If the electrodes selected have different brightness maps, the different maps will be displayed as shown in FIG. 37. The dynamic factor for all the selected electrodes can then be varied by moving the slide-bar (590) just as for an individual electrode. Also in this case, when the desired dynamic factor is set, the 'Apply' button (600) should be pressed.

The timing group can also be changed. The term 'Timing Group' defines the temporal (time domain) stimulation pattern to which each electrode is assigned. If multiple electrodes are assigned to the same timing group, it means that they will be stimulated simultaneously. Different timing groups are stimulated non-simultaneously or interleaved. As indicated in sections (610), (620) and (630) of FIG. 38, the VCF Editor maximizes the distance between electrodes within the same timing group.

The maximum number of timing groups can be calculated as follows:

$$\text{Maximum Number of Timing Groups} = \text{Min}\left(\dfrac{120 \times 3}{\text{Stimulation\_Frequency}}, 60\right)$$

For example, if the stimulation frequency is 20 Hz, the maximum timing groups will be 18. In the embodiment shown in FIG. 38, the maximum number of timing groups for the system does not exceed 60. The above calculation applies to the stimulation pulse width up to 1 ms. The timing group assigned to each electrode can be designated by a color code and a numerical value under the electrode, as shown in FIG. 38, where the six chosen electrodes A01, B08, C05, D02, E09 and F06 are all represented with the same color, e.g., blue. To select all the electrodes in the same timing group, one of the electrodes in that group can be double clicked, as shown in FIG. 38.

With reference to FIG. 39, to change the timing group for an individual electrode: 1) The electrode (e.g., electrode A1 shown as (640)) should be selected by clicking on the visual representation of such electrode; 2) The pull-down menu (650) for the 'Timing Group' should be opened and the desired timing group (660) selected; 3) The "Apply" button should be clicked.

The pull-down menu (650) shows the combined maximum stimulation current for all the electrodes contained within each group of electrodes. The maximum level of simulation current for all the groups is reported as the Maximum Instantaneous Current (see MIC (370) in FIG. 39) above the pull-down menu.

To change the timing group for multiple electrodes: 1) The electrodes should be selected by left-clicking the mouse and dragging the mouse to highlight the group. Alternatively, the electrodes can be selected while pressing down the "ctrl" key on the keyboard. 2) The pull-down menu for the 'Timing Group' should be opened and the desired timing group selected; 3) The "Apply" button should be clicked.

The spatial mapping between the camera output, which has 20×12 pixels and the 10×6 array of electrodes can be modified using the "X Coordinate" and "Y Coordinate" variables in the Edit section, see, e.g. elements (680) and (690) in FIG. 39. Once the X and/or Y Coordinate values are modified, the "Apply" button should be clicked. The X Coordinate can range from 0 to 19 and the Y Coordinate from 0 to 11.

Electrodes can also be disabled, as shown in FIG. 40. To disable an electrode, the electrode (e.g., A05) should be selected (700), (710) and the "Disable electrode" button (420) should be clicked. An 'X' will be displayed in the center of the electrode, as shown in the figure, see reference numeral (700). The disabled electrode's brightness map (730) will contain all zeros for the current amplitude. With reference to the embodiment of FIG. 40, should be noted that once an electrode is disabled in the VCF editor, it can be enabled by changing K. However, if Imin is set to 0, then it cannot be re-enabled using the VCF editor. A new VCF would need to be generated with the desired electrode active.

The VCF can be saved by clicking on the "Save" button, see, e.g., button (740) in FIG. 40. As shown in FIG. 41, video configuration files are stored in a folder named after the particular Subject ID in the "settings" directory in a Video Settings USB Drive. For example, if the Subject ID is "00-001", the folder containing the video configuration files for that particular subject should be named "00-001". The button "open" (750) should be clicked to save the VCF in the specified directory of the Video Settings USB drive as discussed above.

Now the VCF is created and can be loaded onto the VPU using the following procedure:

1—If not already done, the Clinician Fitting System (CFS) or Fitting System (FS) shown in FIG. 3 should be set tip, and Argus II Clinician Fitting System application as previously described should be started. The user should log in to the Clinician Fitting System as described in FIG. 5.

2—The tab "Video", shown in FIGS. 7, 9, 11, 12, 13, 15, 22 and 27, should be clicked. The Video screen, shown in FIG. 42, comprises three sub-sections: A) Stimulation (760); B)

Video Display (770); C) Video Configuration (780). Within the "Stimulation" section (760) is a button (790) to start stimulation of the subject with the video configuration file downloaded to the VPU. The "Video Display" section (770) has two images. The image (800) on the left represents the camera output, which has 20×12 pixels. The image (810) on the right has 10×6 pixels and represents the filtered image sent to the electrode array. The "Video Configuration" section (780) has the button "Load Configuration to VPU" (520). Button (820) should be pressed to load the desired video configuration file to the VPU.

3—Verify that the indicator boxes (830), (840) to the right of "VPU" and "Implant" are illuminated green. If "VPU" indicator box (830) is yellow, verify that the VPU is properly connected. If the "Implant" indicator box (840) is yellow and/or the VPU is sounding an audible alert indicating that linkage with the implant is not established, the subject's RF/coil board assembly on the glasses should be adjusted to establish link.

4—Determine if the file described in "Video Configuration" (780) is the one desired for stimulating the subject. If so, proceed to step 9, if not, proceed to step 5.

5—To load a different video configuration file to the VPU, a USB thumb drive can be connected to an empty port on the USB hub.

6—Click on "Load configuration to the VPU" button (820). A "Load" screen, shown in FIG. 43, will appear with a listing of video configuration files (850) contained in this subject's folder within the "settings" folder (860) on the thumb drive. Clicking on a configuration file in the list (850) will display a description of that selected file in the description box (870) provided that the description was included as part of the video configuration file.

7—When the desired video configuration is located, click on "Load Selection" button (880) to download the selected VCF to the VPU. The file name, along with the load date and time will be displayed in the "Video configuration" section (780) on the Video Screen shown in FIG. 42. Preferably, the VPU will not download any file that does not meet the necessary safety requirements for stimulation. Moreover, in the embodiment shown in the figures, only a single video configuration file can reside at any one time on the VPU.

8—If the incorrect video configuration file is downloaded, repeat steps 5 through 7.

Figure 44:
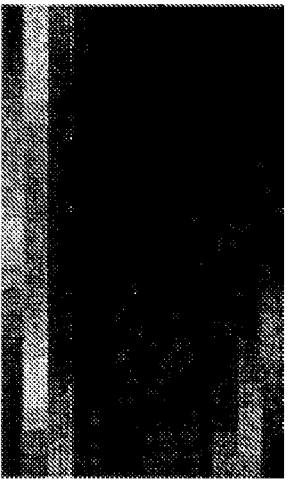
FIG. 44 shows a video screen after start of a video simulation.

9—Once the desired video configuration file is loaded, begin stimulation when the subject is ready by clicking the "Start Simulation" button (790) of FIG. 42. The background of the 10×6 image on the right will change from a first color to a second color (e.g., blue to green) when the stimulation is on, as shown in FIG. 44. It should be noted that if the subject looks at a very bright light (e.g. the sun or a light bulb) while operating in Video mode, stimulation may temporarily be turned off for the subject's protection.

10—To stop stimulation, click the "Stop Simulation" bar (890) shown in FIG. 44 or simply close out the window using the X in the upper right hand corner of the display, as typical with Windows® applications and windows.

11—When video configuration files are being downloaded to the VPU (20) of FIG. 3, the "Video Settings" thumb drive can be safely removed from the hub.

12—To proceed to a different module (Diagnostics, Waveform Viewer, Psychophysics, Options) within Subject Testing, the appropriate tab should be clicked.

The above text and figures have described in detail the purpose and functioning of the VCF editor in accordance with the present disclosure. According to an embodiment of the present disclosure, the VCF editor is a stand-alone program that can operate on any computer with Java Runtime Environment. Some of the features supported by the VCF editor include: up to 60 timing groups with the flexibility to assign any electrode to any timing groups; edit or modify brightness mapping for individual or groups of electrodes; define the stimulation frequency, charge density limit, pulse width, current range, number of timing groups and other global parameters; modify the spatial mapping between the camera output and the electrodes; and disabling electrodes.

In the next paragraphs, the software architecture of the VCF editor will be described in detail.

The VCF editor is designed to be part of the automatic fitting process. The assumption is that a subject has gone through some psychophysics tests, designed to characterize their perception to electrical stimulation. A collection of parameters are extracted from the psychophysics experiment results, serving as the input to the VCF editor.

The VCF Editor is a graphic user interface (GUI) application created using a "Model-View-Controller" (MVC) architectural pattern. The model class contains all the information necessary to specify a video configuration object, as well as a collection of rules to manipulate the information, such as algorithms and methods to create, load, change, and save the video configuration object.

Figure 45:
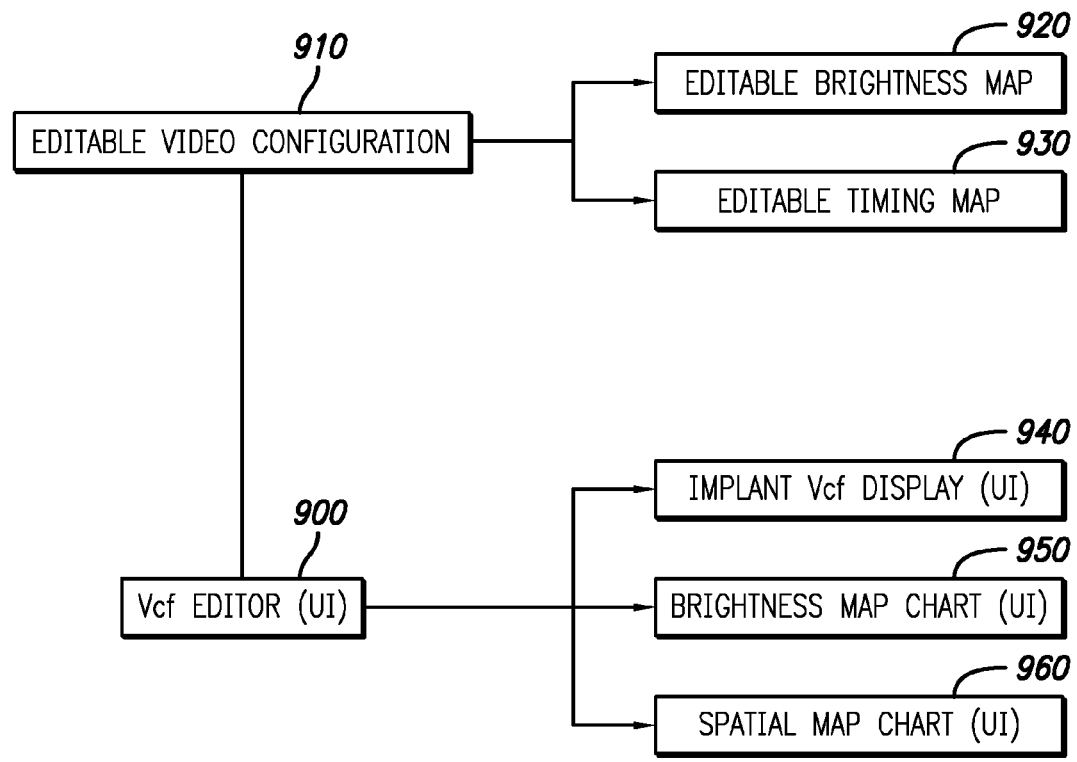
FIG. 45 shows a high level diagram of a possible software architecture of the VCF editor.

FIG. 45 shows a high level diagram showing the major classes. The diagram demonstrates that the main VcfEditor UI class (900) (where UI means user interface) has dependencies on the model (EditableVideoConfiguration (910)) and other display services. However, the model (910) does not have dependencies on the UI (900). This is to allow the UI (900) to be easily modified without affecting the rest of the system. EditableVideoConfiguration class (910) depends on two other classes: the EditableBrightnessMap (920) and the EditableTimingMap (930). The main UI class VcfEditor (900) uses three UI classes: the ImplantVcfDisplay class (940) is used to display the implant diagram; BrightnessMapChart (950) uses a JFreeChart object to display the brightness map plot; and SpatialMapChart (960) is used to display the spatial map. It should be noted that the timing group assignment is displayed on the implant diagram with an ImplantVcfDisplay class as well. The detailed stimulation waveforms of each timing group are not shown.

With reference to the EditableVideoConfiguration class (910), such class is the model of the VcfEditor application. It contains three major types of information: (1) Brightness map; (2) Spatial map; and (3) Timing information. The information is organized so that it can be easily generated, accessed, loaded from and saved to files.

In addition to the classes mentioned above, the VCF Editor shares some classes with the Argus II CFS application. The table shown in FIG. 46 is a short summary of these classes.

The brightness map information is stored in the EditableBrightnessMap object (920) already shown in FIG. 15. This object wraps around the BrightnessMap object and provides access to the raw map using higher level concept such as the "dynamic factor K" (970) and "minimum stimulation Imin" (980), as shown in FIG. 47. The spatial map (980) is stored in a hash map, mapping from the electrode label to its corresponding row-column position. Further, the timing information is stored in the EditableTimingMap object (930) previously discussed with reference to FIG. 45. Object (930) contains the stimulation pattern of each electrode. Electrodes are stimulated by timing groups. Object (930) contains information such as anodicProfiles (990), cathodicProfiles (1000), and dataFrames (1010) which map from the timing group number to the corresponding timing properties. The member variable groupNumbers (1020) corresponds each electrode to a timing group.

The ImplantVcfDisplay class (940) of FIG. 45 is the UI class which is responsible for displaying an implant diagram and accepting user selection inputs. It is derived from the CFS application class ImplantGeometryDisplay.

Class (940) uses the super class methods to draw the implant diagram. In addition, this class will assign a unique color to each of the timing groups by overwriting the method getElectrodeColor( ). The numerical timing group numbers are also displayed as annotations. The user can select electrodes by single clicking, clicking-and-dragging, or double clicking. ImplantVcfDisplay extends the super class by adding a listener VcfMouseEventListener to the mouse events. VcfMouseEventListener listens to mouseClicked, mouseDragged, mousePressed, and mouseReleased events. An instance of ImplantVcfDisplay object is included in the VcfEditor class.

FIGS. 48-51 represent sequence diagrams of auto-generation of video configuration, edit video configuration, save video configuration to file, and load video configuration from a file.

FIG. 48 shows auto-generation of a video configuration. After the application starts, the user (e.g., a field clinical engineer (1030)) can ask the VcfEditor (1040) to automatically generate a video configuration based on parameters such as stimulation frequency, pulse width, etc. In this operation, the UI class VcfEditor calls the model class and passes in the parameters. After the model class finishes updating itself based on the parameters, it informs the UI class to update the display.

FIG. 49 shows editing of the video configuration. The user can select (1050) one or multiple electrodes and change the brightness map (1060), spatial map (1070), or assign it/them to a different timing group (1080). It should be noted that in this embodiment the user is not allowed to modify stimulation frequency, pulse width and stimulation polarity. Instead, a new video configuration should be generated using the auto-generation process of FIG. 48.

FIG. 50 shows an operation of saving the video configuration to file. This is done by creating a VideoConfiguration object (1090) and passing it to a VideoSettingCsvReaderWriter object (1100), which converts and saves the information in .csv format.

FIG. 51 shows an operation of loading a video configuration from an existing file. This is done by creating a VideoSettingCsvReaderWriter object (1100) similarly to what done in the previous operation, and parsing the read VideoConfiguration object (1090) into an EditableVideoConfiguration object (910). During parsing, since the actual timing group numbers are not present in the VideoConfiguration object (1090), they should be referred from the corresponding profile timing and data frame information. When loading the VideoConfiguration (1090), EditableVideoConfiguration (910) will sort all timing group timing information based on (1) the cathodic profile number; and (2) the data frame count. The underlying assumptions are (a) profile numbers are sorted in time, i.e. profile 1 always comes before profile 3 within a data frame; and (b) profiles are always used in pairs, i.e. profile 1 and 2 always are used together.

The auto-generation of the VCF, already shown in FIG. 48, will now be discussed in more detail.

Based on the input from the psychophysics group, the goal of the automatic timing group assignment algorithm is to (1) maximize total number of timing groups used in the video session; and (2) separate the electrodes which are in the same timing group as far as possible in space, i.e. maximize the spatial distances within a timing group. This will help in minimizing the total amount of power used by the implant in any instance.

(1) Maximization of the Total Number of Timing Groups
The total number of timing groups is limited by (1) stimulation frequency; and (2) stimulation pulse width. The stimulation pulse width determines the number of pulses that can be fitted within a data frame (about 6 ms). The stimulation frequency, on the other hand, determines the number of data frames per stimulation frame. The stimulation frequency can only be 120/p Hz, where p is an integer, denoting the number of data frames per stimulation frame. Thus, given a stimulation frequency f, p can be calculated as a ceiling (120/f).

When generating the timing groups, the VcfEditor first maximizes the number of pulses per data frame. Afterwards, it generates a timing table based on the stimulation frequency. The timing table is a map from a timing group number to a pair of profile timings and a data frame number. Thus, each timing group is associated with a pair of pulse profiles and a data frame number.

(2) Maximization of the Spatial Distances within a Timing Group
Given the total number of timing groups N, the VcfEditor object (900) will automatically assign each electrode to a timing group, based on maximization of the spatial distances within a timing group.

According to one of the embodiments of the present disclosure, the VcfEditor can choose not to optimize the assignment through a rigorous mathematical optimization method. A first reason for following such approach is that the target function is not clear. For example, one can argue the goal is to maximize the mean distances between each pair of electrodes that are in the same timing group; or to maximize the minimal distance between any pair of electrodes in the same timing group; etc. A second reason for doing so is that the amount of calculation may be excessive to be carried out on-the-fly within VcfEditor.

VcfEditor aims to maximize the minimal distance between any electrodes that are in the same timing group. VcfEditor assumes that (1) all timing groups 1 ... N will be used equally; (2) the timing assignment on a row can be achieved by shifting assignments on the previous row by X columns; (3) all electrodes are enabled. Based on these constraints, the goal of optimization is to find X given N.

The diagram shown in FIG. 52 summarizes the arrangement of the pattern. Electrodes represented in grey are in the same timing group. Pitch distances are denoted by "p" (horizontal pitch) and "q" (vertical pitch). Thus, $$d1 = \sqrt{(p \cdot X)^2 + q^2}$$

$$d2 = Y \cdot q$$

To ensure that electrodes in the same timing group are distributed evenly in space, d1 and d2 should be (roughly) equal to each other. On the other hand, after shifting X columns per row, for a total of Y rows, since one expects to repeat the pattern in the first row, it can be concluded that:

$$X(\text{columnShifted/row}) * Y(\text{rows/repeat}) = N(\text{columnShifted/repeat})$$

Using the above two equations, X can be calculated as:

$$X = \sqrt{\frac{-q^2 + \sqrt{q^4 + 4p^2 N^2 q^2}}{2p^2}}$$

The above calculation also assumes the array is infinitely large on both row and column directions. In reality, however, if there are many timing groups, the algorithm needs to make sure all groups are used before it reaches the last row. Therefore:

$$X = \sqrt{\frac{-q^2 + \sqrt{q^4 + 4p^2 N^2 q^2}}{2p^2}} \; ; \text{if } N < M$$
$$= 10; \text{if } N >= M$$

The threshold M currently chosen through trial-and-error is 36. Assuming three pulses can be fit within one data frame, this essentially means X=10 when stimulation frequency is less than 10 Hz.

On the basis of the above, the algorithm used by the VCF Editor to assign the timing group can be described as follows:
(1) Calculate the column shifting value X according to the above equation
(2) Fill the first row with a pattern 1 ... N, 1 ... N (repeat if needed)
(3) Shift the above pattern X times to the left and fill the next row
(4) Repeat step (3) until all electrodes are assigned to a group FIG. 53 shows an exemplary result of the above algorithm. In this example, N=6, and the calculated X is 3. It should be noted that the pattern on the second row is simply the pattern on the first row shifted 3 electrodes to the left. In addition, the horizontal pitch is p=0.575 and the vertical pitch is q=0.725.

Generation of the brightness map will now be discussed. The brightness map of an electrode can be defined as:

Amplitude =

$$\begin{cases} \text{Im in} * \left(1 + (K-1) * \frac{\text{Brightness} - V\min}{V\max - V\min}\right), & \text{if Brightness} >= V\min \\ 0, & \text{if Brightness} < V\min \end{cases}$$

in which Vmin is the minimal brightness level (0-31), Imin is the minimal stimulation current for each of the electrodes, and K is the dynamic factor.

If the amplitude value is greater than the maximum safe limit Imax, such value is set to Imax. Imax represents the maximum stimulation amplitude for each electrode. This amplitude is determined by the charge density limit (CDL) and the stimulation current range specified. If the Imin is greater than Imax, Imin is set to 0, if the difference between Imin and Imax is less than 3 digital settings, the electrode is considered "disabled" and the brightness map shall be set to 0. The generated amplitude is compared to Imax, which is determined by the combination of both the maximum stimulation under the current range, and the charge density limit (CDL). Basically, Imax is used as the stimulation level if the above amplitude exceeds it.

When calculating the digital amplitude using the above formula, the following method can be used in order to minimize digitization errors:

(1) convert Imin from μA to the closest digital units Imin_digital. And then convert the Imin_digital to Imin_star with a flooring operation. This way, Imin_star will always be accurately represented using the discrete stimulation settings.
(2) calculate the stimulation amplitude "Amplitude" in μA;
(3) convert the above "amplitude" from μA to digital units (amplitude_digital) using a rounding method;
(4) compare "amplitude_digital" with Imax (in digital units) and pick the minimum.

When automatically generating a brightness map, the default dynamic factor K is calculated from the number of electrodes whose brightness map will saturate at Imax. It is known that for a non-disabled electrode, if the dynamic factor K increases, the slope of the brightness map will increase. Applicants enumerate through all possible dynamic factor K's and use the minimum one which leads to the number of saturated electrodes requested.

In general, this system gives the experimenter great flexibility to present spatio-temporal stimulation patterns to a subject. The subject then responds by drawing their phosphene on a touchscreen. Quantitative analysis of their percepts is then conducted by assigning image descriptors to the touchscreen data.

While the present disclosure describes a touchscreen, there are many methods for a patient to indicate a pattern perceived through a visual prosthesis by means of a drawing input device. Other possible drawing input devices include observed hand movements through a video processor, an optically or electrically scanning stylus, various known devices for movement sensing such as inertial or electrical field sensing controllers.

The VCF editor allows the experimenter to determine the electrical stimulation parameters for each electrode. The Pattern Stimulation software allows direct stimulation of chosen patterns of electrodes, scaled by the subject's VCF, through a Graphical User Interface. It also provides a mechanism for gathering subject input through a touch screen monitor, if desired. The subject draws their visual percept on a touchscreen monitor that is placed in from of them.

After the experiment, offline image analysis can be performed, to obtain a detailed quantitative description of the subject's percepts. These image descriptors can be used to make formalized comparisons between various experimental conditions. Various types of image descriptors can be used, including simple ellipse fitting, projections of the 2-D drawings onto one-dimensional axes, calculations of Hu moments, principal component analysis (PCA), independent component analysis (ICA), etc.

There are two modes of operation of the Pattern Stimulation program—single pattern experiments and repeated pattern experiments. Single pattern experiments are conducted in each trial, the user selects a single pattern and parameters (video level, duration, frequency, pulse width, etc.) and stimulates. Touch screen input can be recorded or not, as desired. The experimenter may run repeated patterns experiments in which several patterns are selected, parameters are set (including more than one video level, if desired) and the number of repeats is defined. The experiment loops through all trials (total trials=number of patterns×number of video levels×number of repeats) randomly, gathering touch screen input for each trial. You can choose whether to plot the subject's response and an ellipse fitted to the data for each trial.

Example Experiment 1

Figure 54:
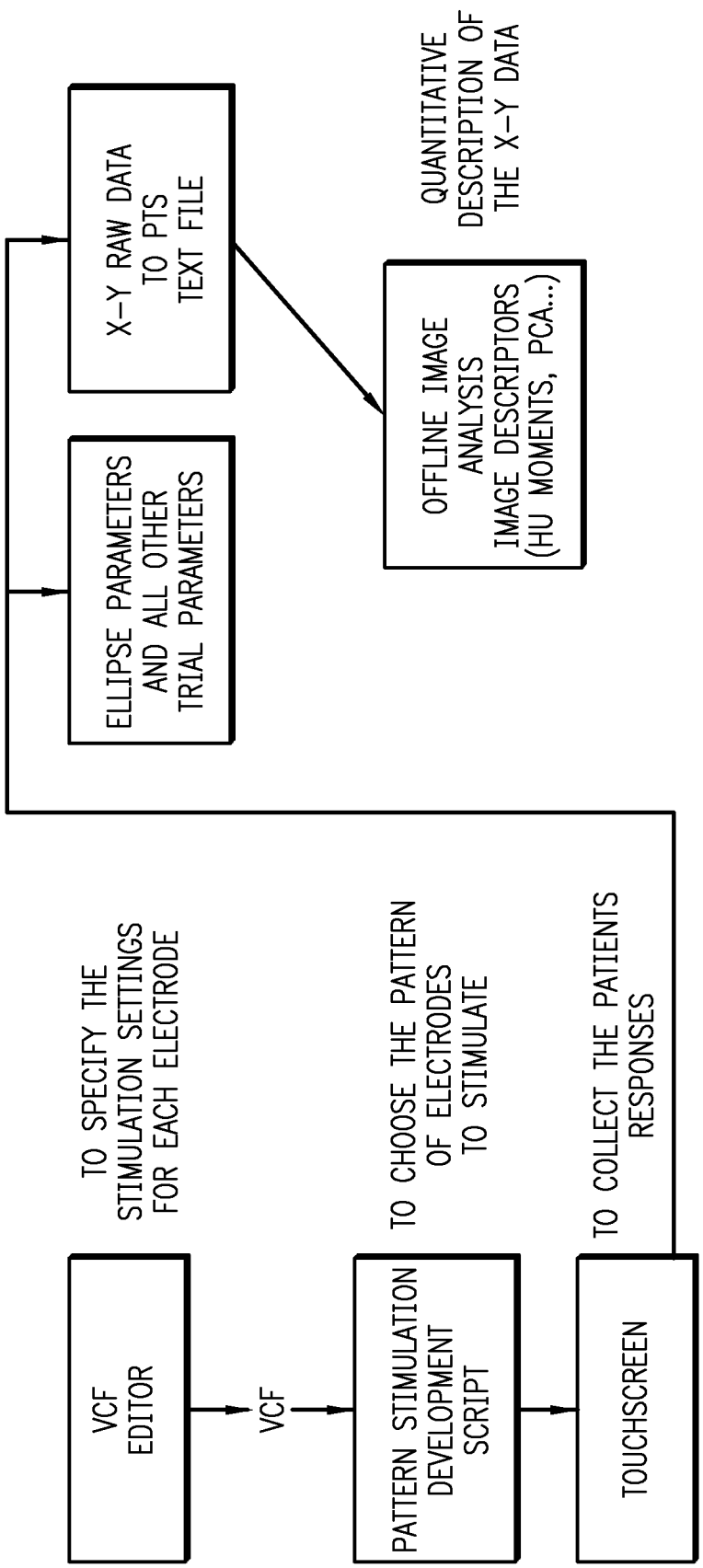
FIG. 54 is a flowchart showing the preferred method of measuring spatio-temporal vision

As Illustrated in FIG. 54

Is a "line" made clearer if it is formed by a row of simultaneously stimulated electrodes, or a row of staggered electrodes?

1) Use the VCF Editor to set up 2 VCF's
   a) Row A electrodes in the same timing group
   b) Row A electrodes all in different timing groups
2) Run Pattern Stimulation Development Script
   Load VCF a) above
   Select all electrodes, in row A for stimulation
   Record responses from subject
   Load VCF b) above
   Select all electrodes in row A for stimulation
   Record responses from subject
3) Compare the responses for the two VCF's
   Subjectively look at the x-y data or
   Look at ellipse parameters or
   Use analysis toolbox to look at more sophisticated Image Descriptors (hu moments, PCA, ICA, etc.)

Figure 55:
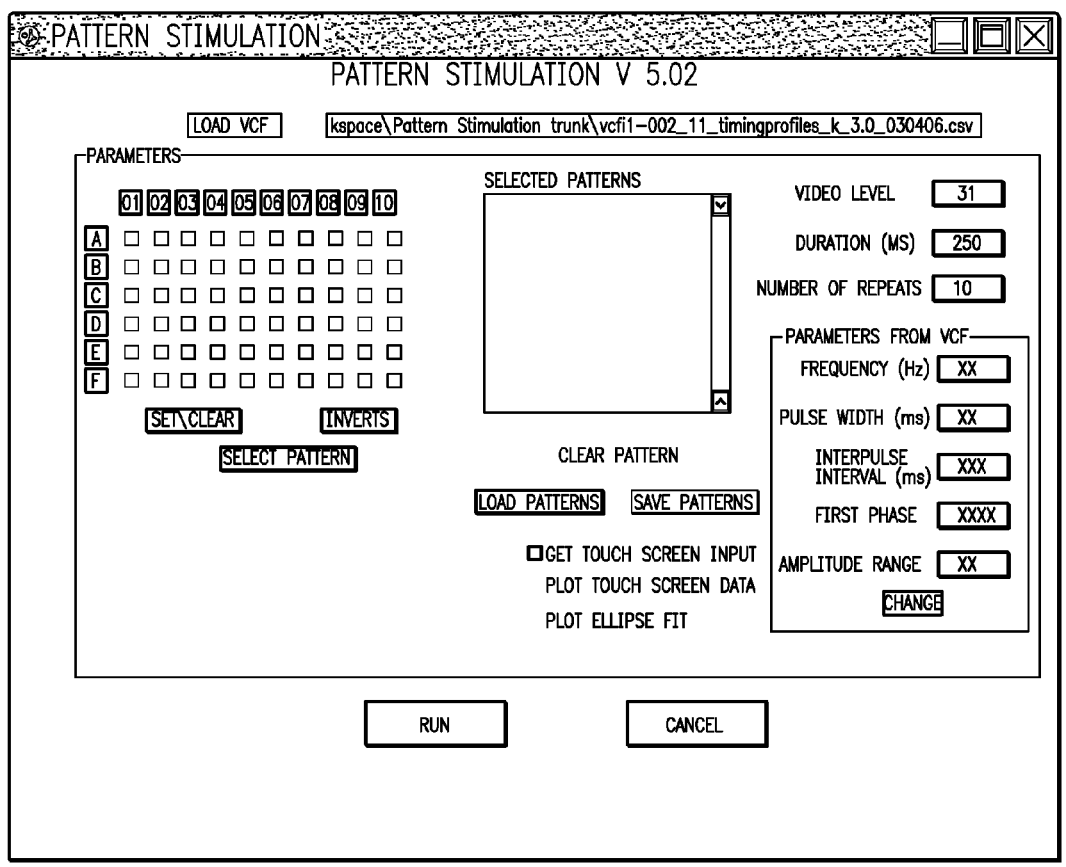
FIGS. 55-57 are screen shots of a computer terminal running software implementing the preferred method of measuring spatio-temporal vision.

FIG. 55 is a screen shot of the Pattern Stimulation GUI after a VCF has been loaded. The checkboxes representing electrodes disabled on the implant or unused (amplitude of 0 for all video levels) in the VCF are disabled. Whole rows or columns of electrodes can be selected by clicking the appropriate buttons (A, B, C, 01, 02, etc). Individual electrodes can be selected by clicking directly in the boxes.

The listbox in the middle ("Selected Patterns") is only used for Repeated Patterns experiments; it will remain empty for Single Patterns experiments. Video level, duration and number of repeats (relevant only for Repeated Patterns experiments) can be set directly using the edit boxes on the right.

The other parameters—frequency, pulse width, interpulse interval, first phase, and amplitude range—are calculated from the loaded VCF. Only VCF features that are supported by the VCF Editor are supported in Pattern Stimulation. For example, Pattern Stimulation will not allow you to load a VCF that contains different pulse widths in different timing profiles.

You can change the VCF parameters by clicking the "Change" button. NOTE: changing these parameters should be done with caution—setting invalid parameters will cause errors when you attempt to stimulate, and could crash the program. For example, frequencies above 20 Hz at a pulse width of 0.45 ms are not supported when 18 timing groups are defined in the VCF. In general, it is much better to change the VCF itself using the VCF Editor (which will not allow you to specify invalid parameters) than it is to change the parameters in Pattern Stimulation.

Repeated Patterns experiments always gather touch screen input for each trial, though you can choose whether you want to see the plot of the subject's response as well as results of the online analysis (an ellipse fit to the data with five free parameters). For Single Patterns experiments, you can decide whether to gather touch screen input or not.

When gathering touch screen input, the clinician instructs the subject to trace the size and shape of the percept they see slowly with their finger. If the subject sees multiple shapes, they should be instructed to draw them all, though they should not re-draw the same shape. When the subject is finished drawing, the clinician goes on to the next trial by pressing "yes" on the keypad. If the subject did not see anything or cannot draw a shape, the clinician presses "yes" to advance without touching the monitor.

Raw data text files are written to the current direction. For each experiment, there is a parameter file that lists all the parameters for each trial. In addition, the raw (x,y) data are written to a separate file for each trial. All trial parameters and ellipse fit parameters are written to the CFS log file.

Example Experiment 2

Figure 56:
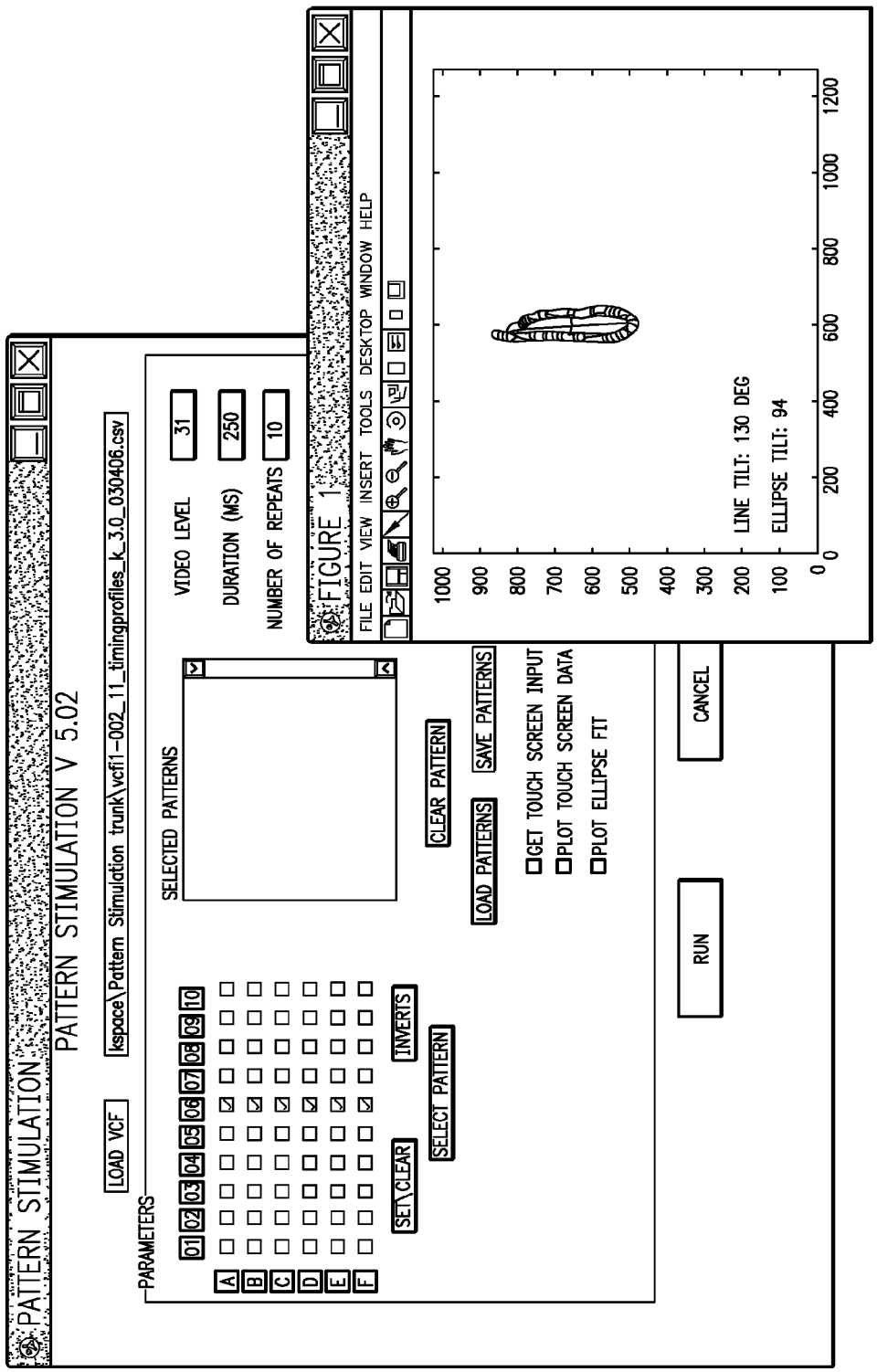

1. Running Pattern Stimulation—Single Patterns Experiment (as Illustrated in FIG. 56)
   Load a VCF by clicking the "Load VCF" button and selecting a VCF from the Windows explorer window.
   Choose the desired electrodes to stimulate using the checkboxes.
   Choose the desired video level and duration.
   If you do not wish to gather touch screen input, leave the "Get Touch Screen Input" box unchecked. Otherwise, check the box. You can also choose whether to plot the subject's response and to plot the results of the online ellipse analysis.
   To stimulate the electrodes, click "Run". The Cancel button can be clicked any time during the stimulation to abort it.
   After stimulation, if you are gathering input, a blank figure will appear on the touch screen; the subject should trace the percept with their finger and report when they are finished.
   Press "yes" on the key pad when the subject is finished drawing.
   Continue stimulating for the desired number of trials with different patterns, parameters, and VCFs if desired. All trials will be contained as a single experiment until either 1) you close the Pattern Stimulation GUI, or 2) you run a Repeated Patterns experiment.

Example Experiment 3

Figure 57:
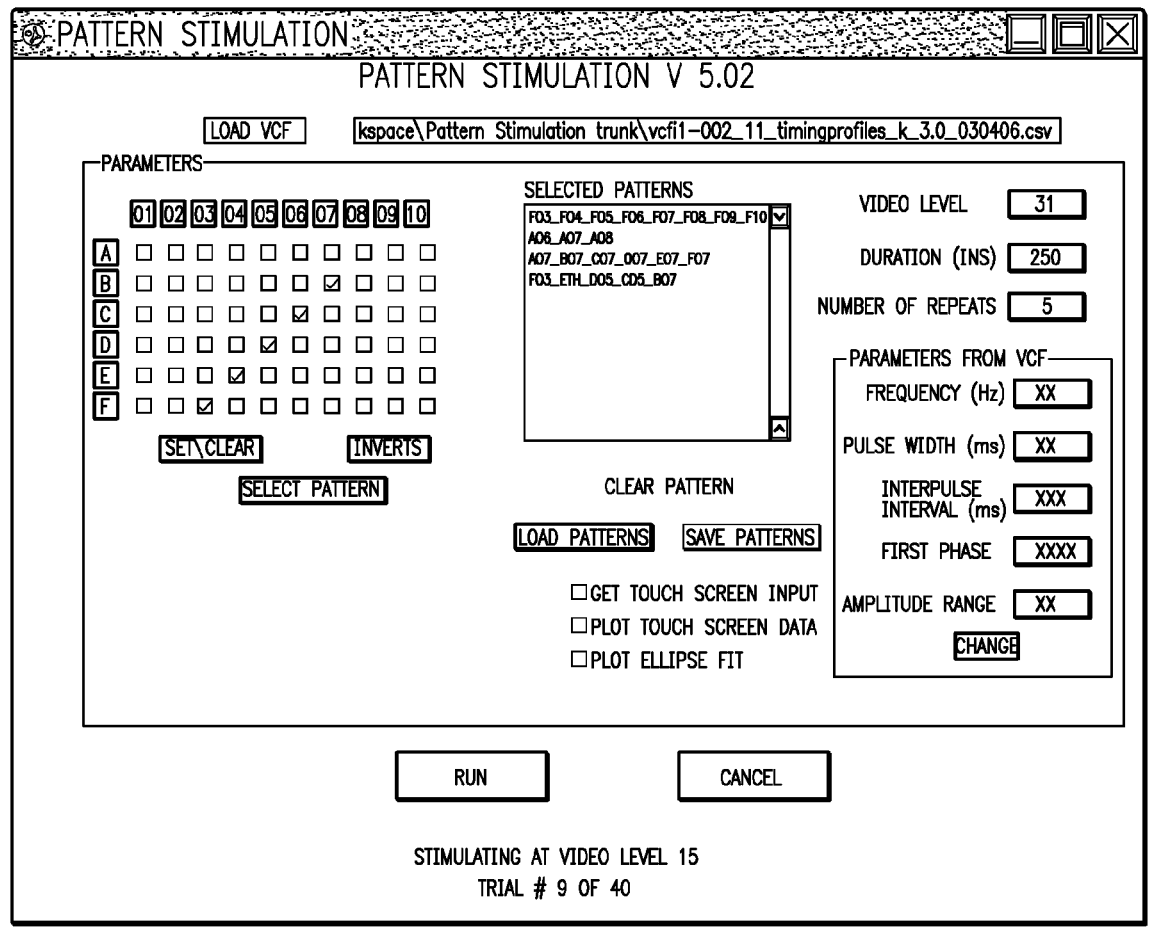

2. Running a Repeated Patterns Experiment (as Illustrated in FIG. 57)
   After loading a VCF, you must choose several patterns of electrodes. You can select patterns in two ways: using the GUI, or by loading a text file.
      To select patterns using the GUI: check the boxes representing whichever electrodes you want in the first pattern and click the Select Pattern button. The pattern is placed in the Selected Patterns list. Continue to select new patterns using the GUI, adding them to the list. To delete patterns, select it in the list and click the Clear Pattern button.
      To select patterns using a text file: click on the "Load patterns from file" button and select the file using the Explorer window that pops up. The text file should contain only a list of electrodes, separated by commas—one pattern on each line.
   Set the desired video levels; more than one level should be separated by commas (e.g., '25,31').
   Set the desired duration and frequency.
   Set the desired number of repeats. Each pattern will be stimulated at each video level the chosen number of repeats.
   If you wish to see the subject's response and the fitted ellipse, ensure that those boxes are checked.
   Click "Run."
   During the stimulation, the GUI will show which pattern is being stimulated (in the electrode checkboxes and in the list of patterns) as well as the video level and trial number.
   After each stimulation, the program will wait for touch screen input. When the subject is finished drawing, press the "yes" button on the keypad.
   You can cancel the stimulation/experiment at any time by clicking the "Cancel" button. If you click Cancel during a stimulation, it will immediately be aborted. You can then choose whether to end the experiment. You may need press "yes" on the key pad before the program terminates.
3. Results and Analysis
   Results are written out in several ways. The psychophysics log file in CFS contains a complete history of the experiment, including all experiment and trial parameters, as well as the fitted ellipse parameters. There will be a separate psychophysics log file for each experiment of either type (Single Patterns or Repeated Patterns). Parts of an example Repeated Patterns experiment log file are shown below.

```
[start_experiment]
  time=2008/08/20 14:10:14 390
  name=Pattern Stimulation v5.02
  PTS_parameterFilename=
  20080820_141014_xx-xxx_repeatedPatterns_5-02.txt
  PTS_generatorfunction=MISSING FIELD
  PTS_experimentType=repeatedPatterns
[start_trial]
  time=2008/08/20 14:10:21 734
  PTS_vcfName=vcf11-002_11_timingprofiles_k_3.0_030408.csv
  PTS_electrodes=A06_A07_A08
  PTS_firstPhase=Cathodic
  PTS_duration=250
  PTS_fileName=20080820_141014_trial2.txt
  PTS_pulseWidth=0.46
  PTS_trial=2
  PTS_frequency=20
  PTS_videoLevel=31
  PTS_interpulseInterval=0
  PTS_amplitudeRange=250
[stimulus]
  time=2008/08/20 14:10:21 796
  name=trial_2_videoLevel_31_pattern_A06_A07_A08
  stimulus=trial_2_videoLevel_31_pattern_A06_A07_A08-0
  ...
[end_trial]
  time=2008/08/20 14:10:25 109
  PTS_ellipseTiltAngle=0.073283
  PTS_ellipseXCenter=615.38
  PTS_ellipseXDim=39.468
  PTS_ellipseYCenter=597.47
  PTS_trial=2
  PTS_stimulationCompleted=true
  PTS_ellipseYDim=192.17
    cfs_status=ok
```

Several results files are also written out to the current directory (usually the thumb drive). For each experiment, there is a one tab-separated text file that contains the parameters for each trial. It is named: repeatedPatterns_5-02_[subjectID]_[date]_[experiment timestamp].txt. An example is shown below; column headers have been added for clarity, but are not contained in the actual file.

names of the Parameter and Results files are also written to the psychophysics log file (highlighted above) for later cross-checking. An example data file is shown below; again, headers are added for clarity but are not contained in the file.

20080820_141014_trial2.txt:

| X | Y | Segment ID |
|---|---|---|
| 772 | 797 | 1 |
| 770 | 797 | 1 |
| 769 | 797 | 1 |
| 768 | 796 | 1 |
| 766 | 795 | 1 |
| 763 | 793 | 1 |
| 761 | 793 | 1 |
| 759 | 792 | 1 |
| 755 | 790 | 1 |
| 750 | 787 | 1 |
| 746 | 784 | 1 |
| 743 | 782 | 1 |
| 739 | 779 | 1 |
| 735 | 776 | 1 |
| 734 | 775 | 1 |
| 732 | 774 | 1 |
| 730 | 772 | 1 |
| 729 | 771 | 1 |
| 725 | 769 | 1 |
| 723 | 768 | 1 |
| 722 | 766 | 1 |
| 712 | 765 | 1 |
| 710 | 763 | 1 |
| 709 | 761 | 1 |

Accordingly, what has been shown is a system of fitting for visual prosthesis fitting and related method. While the fitting system and method have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

20080820_141014_xx-xxx_repeatedPatterns_5-02.txt:

| Trial | VCF name | Electrodes | Video Level | Freq. | Duration | Pulse Width | Interpulse Interval | Current Range | First Phase |
|---|---|---|---|---|---|---|---|---|---|
| 1 | vcf11-002_030408.csv | F08_F09_F10 | 31 | 20 | 250 | 0.46 | 0 | 250 | Cathodic |
| 2 | vcf11-002_030408.csv | D05_C06_B07 | 31 | 20 | 250 | 0.46 | 0 | 250 | Cathodic |
| 3 | vcf11-002_030408.csv | E03_F03_E04_F04 | 31 | 20 | 250 | 0.46 | 0 | 250 | Cathodic |
| 4 | vcf11-002_030408.csv | F08_F09_F10 | 15 | 20 | 250 | 0.46 | 0 | 250 | Cathodic |
| 5 | vcf11-002_030408.csv | D05_C06_B07 | 15 | 20 | 250 | 0.46 | 0 | 250 | Cathodic |
| 6 | vcf11-002_030408.csv | E03_F03_E04_F04 | 15 | 20 | 250 | 0.46 | 0 | 250 | Cathodic |
| 7 | vcf11-002_030408.csv | F08_F09_F10 | 15 | 20 | 250 | 0.46 | 0 | 250 | Cathodic |
| 8 | vcf11-002_030408.csv | F08_F09_F10 | 31 | 20 | 250 | 0.46 | 0 | 250 | Cathodic |
| 9 | vcf11-002_030408.csv | D05_C06_B07 | 15 | 20 | 250 | 0.46 | 0 | 250 | Cathodic |
| 10 | vcf11-002_030408.csv | E03_F03_E04_F04 | 15 | 20 | 250 | 0.46 | 0 | 250 | Cathodic |
| 11 | vcf11-002_030408.csv | D05_C06_B07 | 31 | 20 | 250 | 0.46 | 0 | 250 | Cathodic |
| 12 | vcf11-002_030408.csv | E03_F03_E04_F04 | 31 | 20 | 250 | 0.46 | 0 | 250 | Cathodic |

In addition, the raw touch screen results for each trial are written out in a separate file named: [date]_[experiment timestamp]_trial[x].txt. Therefore, the trial and parameter files can be matched with the experiment timestamps in the name—the timestamp will be unique to each experiment. The

The invention claimed is:
1. A method of measuring electrically induced vision comprising:
   providing a visual prosthesis including:
      a neural stimulator having a plurality of electrodes suitable to stimulate visual neurons, a visual user interface including a drawing input device; and an operational control device controlling the neural stimulator and the visual user interface;

selecting and stimulating a stimulation pattern including a subset of said plurality of electrodes;

stimulating a patient, using the neural stimulator with the stimulation pattern creating a patent response;

collecting the patient responses in the operation control device via the patient drawing their perception of the stimulation pattern on the drawing input device;

analyzing a relationship of the stimulation pattern and the patient response in the operational control device; and adjusting the visual prosthesis according to the relationship.

2. The method according to claim 1, further comprising creating and storing a map of the relationship of the stimulation pattern and the patient response; and creating a perception of a visual image using the map.

3. The method according to claim 1, wherein the drawing input device is a touch sensitive surface.

4. The method according to claim 3, wherein the touch sensitive surface is also a display providing feed back of the patient response.

5. The method according to claim 1, wherein the step of analyzing a relationship of the stimulation pattern and the patient response in the operational control device includes ellipse fitting to fit the patient responses to stimulation patterns.

6. The method according to claim 1, wherein the step of analyzing a relationship of the stimulation pattern and the patient response in the operational control device includes Hu moments to fit the patient responses to stimulation patterns.

7. The method according to claim 1, wherein the step of analyzing a relationship of the stimulation pattern and the patient response in the operational control device includes projections of two dimensional drawings on one dimensional axes to fit the patient responses to stimulation patterns.

8. The method according to claim 1, wherein the steps selecting, stimulating and collecting are repeated multiple times and the step of analyzing involves averaging results of the multiple times.

9. The method according to claim 1, wherein the step of analyzing a relationship of the stimulation pattern and the patient response in the operational control device includes principle component analysis to fit the patient responses to stimulation patterns.

10. The method according to claim 9, wherein the step of analyzing a relationship of the stimulation pattern and the patient response in the operational control device includes independent component analysis to fit the patient responses to stimulation patterns.

* * * * *